United States Patent
Kaleko et al.

(10) Patent No.: US 11,517,614 B2
(45) Date of Patent: *Dec. 6, 2022

(54) MICROBIOME PROTECTION FROM ORAL ANTIBIOTICS

(71) Applicant: Synthetic Biologies, Inc., Rockville, MD (US)

(72) Inventors: Michael Kaleko, Rockville, MD (US); Sheila Connelly, Rockville, MD (US)

(73) Assignee: Synthetic Biologics, Inc., Rockville, MD (US)

( * ) Notice: Subject to any disclaimer, the term of this patent is extended or adjusted under 35 U.S.C. 154(b) by 934 days.

This patent is subject to a terminal disclaimer.

(21) Appl. No.: 16/313,488

(22) PCT Filed: Jun. 28, 2017

(86) PCT No.: PCT/US2017/039672
§ 371 (c)(1),
(2) Date: Dec. 27, 2018

(87) PCT Pub. No.: WO2018/005606
PCT Pub. Date: Jan. 4, 2018

(65) Prior Publication Data
US 2021/0220452 A1     Jul. 22, 2021

Related U.S. Application Data

(60) Provisional application No. 62/355,599, filed on Jun. 28, 2016.

(51) Int. Cl.
| | | |
|---|---|---|
| A61K 38/50 | (2006.01) | |
| A61K 9/00 | (2006.01) | |
| A61K 9/48 | (2006.01) | |
| A61K 9/50 | (2006.01) | |
| A61K 31/424 | (2006.01) | |
| A61K 38/14 | (2006.01) | |

(52) U.S. Cl.
CPC ............ *A61K 38/50* (2013.01); *A61K 9/0053* (2013.01); *A61K 9/4808* (2013.01); *A61K 9/4858* (2013.01); *A61K 9/4866* (2013.01); *A61K 9/4891* (2013.01); *A61K 9/5026* (2013.01); *A61K 9/5084* (2013.01); *A61K 31/424* (2013.01); *C12Y 305/02006* (2013.01); *A61K 38/14* (2013.01)

(58) Field of Classification Search
CPC .... A61K 38/50; A61K 9/0053; A61K 9/4808; A61K 9/4858; A61K 9/4866; A61K 9/4891; A61K 9/5026; A61K 9/5084; A61K 31/424; C12Y 305/02006; A61P 1/12; A61P 31/04
See application file for complete search history.

(56) References Cited

U.S. PATENT DOCUMENTS 8,273,376 B2    9/2012 Andremont et al.

FOREIGN PATENT DOCUMENTS

| WO | WO 2008065247 A1 | 6/2008 |
| WO | WO 2015161243 A2 | 10/2015 |
| WO | WO 2016057744 A1 | 4/2016 |
| WO | WO 2016137993 A1 | 9/2016 |

OTHER PUBLICATIONS

International Search Report & Written Opinion, PCT Appl. No. PCT/US17/39672, dated Sep. 28, 2017, 11 pages.
Kaleko, et al., "Development of SYN-004, an oral beta-lactamase treatment to protect the gut microbiome from antibiotic-mediated damage and prevent *Clostridium difficile* infection," Anaerobe, vol. 41, pp. 58-67, Jun. 2, 2016.

*Primary Examiner* — Kade Ariani
(74) *Attorney, Agent, or Firm* — Morgan, Lewis & Bockius LLP

(57) ABSTRACT

This invention provides, in part, various compositions and methods for protecting the gastrointestinal microbiome from antibiotic disruption from orally administered antibiotics.

20 Claims, 31 Drawing Sheets

Specification includes a Sequence Listing.

FIG. 31

| Code | Capsule | Capsule coating | Pellets coating | Coding |
|---|---|---|---|---|
| F1 | DRcap | | FS 30 D (20% dry polymer weight gain) | One line on white capsules |
| F2 | Gelatin | | FS 30 D (20% dry polymer weight gain) | Two lines on half-transparent capsules |
| F3 | DRcap | 5.5mg/cm² FS 30 D | S100 (40% dry polymer weight gain) | Three lines on white capsules |
| F4 | Gelatin | | S100 (40% dry polymer weight gain) | No line on half-transparent capsules |
| F5 | DRcap | | Duocoat FS 30 D (inner 5% and outer 20% dry polymer weight gain) | No line on white capsules |

SEQUENCE LISTING

```
<160> NUMBER OF SEQ ID NOS: 7

<210> SEQ ID NO 1
<211> LENGTH: 263
<212> TYPE: PRT
<213> ORGANISM: Bacillus licheniformis

<400> SEQUENCE: 1

Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Tyr Thr Arg Asp Asp Leu Val Asn Tyr Asn Pro Ile Thr Glu
65                  70                  75                  80

Lys His Val Asp Thr Gly Met Thr Leu Lys Glu Leu Ala Asp Ala Ser
                85                  90                  95

Leu Arg Tyr Ser Asp Asn Ala Ala Gln Asn Leu Ile Leu Lys Gln Ile
            100                 105                 110

Gly Gly Pro Glu Ser Leu Lys Lys Glu Leu Arg Lys Ile Gly Asp Glu
        115                 120                 125

Val Thr Asn Pro Glu Arg Phe Glu Pro Glu Leu Asn Glu Val Asn Pro
    130                 135                 140
```

```
Gly Glu Thr Gln Asp Thr Ser Thr Ala Arg Ala Leu Val Thr Ser Leu
145                 150                 155                 160

Arg Ala Phe Ala Leu Glu Asp Lys Leu Pro Ser Glu Lys Arg Glu Leu
            165                 170                 175

Leu Ile Asp Trp Met Lys Arg Asn Thr Thr Gly Asp Ala Leu Ile Arg
        180                 185                 190

Ala Gly Val Pro Asp Gly Trp Glu Val Ala Asp Lys Thr Gly Ala Ala
            195                 200                 205

Ser Tyr Gly Thr Arg Asn Asp Ile Ala Ile Ile Trp Pro Pro Lys Gly
        210                 215                 220

Asp Pro Val Val Leu Ala Val Leu Ser Ser Arg Asp Lys Lys Asp Ala
225                 230                 235                 240

Lys Tyr Asp Asp Lys Leu Ile Ala Glu Ala Thr Lys Val Val Met Lys
                245                 250                 255

Ala Leu Asn Met Asn Gly Lys
            260
```

<210> SEQ ID NO 2
<211> LENGTH: 792
<212> TYPE: DNA
<213> ORGANISM: Bacillus licheniformis

<400> SEQUENCE: 2

```
gagatgaaag atgattttgc aaaacttgag gaacaatttg atgcaaaact cgggatcttt      60
gcattggata caggtacaaa ccggacggta gcgtatcggc cggatgagcg ttttgctttt     120
gcttcgacga ttaaggcttt aactgtaggc gtgcttttgc aacagaaatc aatagaagat     180
ctgaaccaga gaataacata tacacgtgat gatcttgtaa actacaaccc gattacggaa     240
aagcacgttg atacgggaat gacgctcaaa gagcttgcgg atgcttcgct tcgatatagt     300
gacaatgcgg cacagaatct cattcttaaa caaattggcg gacctgaaag tttgaaaaag     360
gaactgagga gattggtga tgaggttaca aatcccgaac gattcgaacc agagttaaat     420
gaagtgaatc cgggtgaaac tcaggatacc agtacagcaa gagcacttgt cacaagcctt     480
cgagcctttg ctcttgaaga taaacttcca agtgaaaaac gcgagctttt aatcgattgg     540
atgaaacgaa ataccactgg agacgcctta atccgtgccg gtgtgccgga cggttgggaa     600
gtggctgata aactggagc ggcatcatat ggaacccgga tgacattgc catcatttgg     660
ccgccaaaag gagatcctgt cgttcttgca gtattatcca gcagggataa aaggacgcc     720
aagtatgatg ataaactat tgcagaggca acaaaggtgg taatgaaagc cttaaacatg     780
aacggcaaat aa                                                         792
```

<210> SEQ ID NO 3
<211> LENGTH: 299
<212> TYPE: PRT
<213> ORGANISM: Bacillus licheniformis

<400> SEQUENCE: 3

```
Met Ile Gln Lys Arg Lys Arg Thr Val Ser Phe Arg Leu Val Leu Met
1               5                   10                  15

Cys Thr Leu Leu Phe Val Ser Leu Pro Ile Thr Lys Ser Ala Gln
            20                  25                  30

Ala Ser Lys Thr Glu Met Lys Asp Asp Phe Ala Lys Leu Glu Glu Gln
            35                  40                  45

Phe Asp Ala Lys Leu Gly Ile Phe Ala Leu Asp Thr Gly Thr Asn Arg
        50                  55                  60
```

Thr Val Ala Tyr Arg Pro Asp Glu Arg Phe Ala Phe Ala Ser Thr Ile
65                  70                  75                  80

Lys Ala Leu Thr Val Gly Val Leu Leu Gln Gln Lys Ser Ile Glu Asp
                85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
        115                 120                 125

Ala Asp Ala Ser Leu Arg Tyr Ser Asp Asn Ala Ala Gln Asn Leu Ile
    130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Leu Asn
                165                 170                 175

Glu Val Asn Pro Gly Glu Thr Gln Asp Thr Ser Thr Ala Arg Ala Leu
            180                 185                 190

Val Thr Ser Leu Arg Ala Phe Ala Leu Glu Asp Lys Leu Pro Ser Glu
        195                 200                 205

Lys Arg Glu Leu Leu Ile Asp Trp Met Lys Arg Asn Thr Thr Gly Asp
210                 215                 220

Ala Leu Ile Arg Ala Gly Val Pro Asp Gly Trp Glu Val Ala Asp Lys
225                 230                 235                 240

Thr Gly Ala Ala Ser Tyr Gly Thr Arg Asn Asp Ile Ala Ile Ile Trp
                245                 250                 255

Pro Pro Lys Gly Asp Pro Val Val Leu Ala Val Leu Ser Ser Arg Asp
            260                 265                 270

Lys Lys Asp Ala Lys Tyr Asp Asp Lys Leu Ile Ala Glu Ala Thr Lys
        275                 280                 285

Val Val Met Lys Ala Leu Asn Met Asn Gly Lys
    290                 295

<210> SEQ ID NO 4
<211> LENGTH: 900
<212> TYPE: DNA
<213> ORGANISM: Bacillus licheniformis

<400> SEQUENCE: 4
atgattcaaa aacgaaagcg acagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg ggatctttgc attggataca     180
ggtacaaacc ggacggtagc gtatcggccg atgagcgtt ttgcttttgc ttcgacgatt      240
aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480
attggtgatg aggttacaaa tcccgaacga ttcgaaccag agttaaatga agtgaatccg     540
ggtgaaactc aggataccag tacagcaaga gcacttgtca caagccttcg agcctttgct     600
cttgaagata aacttccaag tgaaaaacgc gagcttttaa tcgattggat gaaacgaaat     660
accactggag acgccttaat ccgtgccggt gtgccggacg gttgggaagt ggctgataaa     720
actggagcgg catcatatgg aacccggaat gacattgcca tcatttggcc gccaaaagga     780

```
gatcctgtcg ttcttgcagt attatccagc agggataaaa aggacgccaa gtatgatgat    840
aaacttattg cagaggcaac aaaggtggta atgaaagcct taaacatgaa cggcaaataa    900
```

<210> SEQ ID NO 5
<211> LENGTH: 262
<212> TYPE: PRT
<213> ORGANISM: Artificial Sequence
<220> FEATURE:
<223> OTHER INFORMATION: Synthetic sequence

<400> SEQUENCE: 5

```
Glu Met Lys Asp Asp Phe Ala Lys Leu Glu Glu Gln Phe Asp Ala Lys
1               5                   10                  15

Leu Gly Ile Phe Ala Leu Asp Thr Gly Thr Asn Arg Thr Val Ala Tyr
            20                  25                  30

Arg Pro Asp Glu Arg Phe Ala Phe Ala Ser Thr Ile Lys Ala Leu Thr
        35                  40                  45

Val Gly Val Leu Leu Gln Gln Lys Ser Ile Glu Asp Leu Asn Gln Arg
    50                  55                  60

Ile Thr Thr Arg Asp Asp Leu Val Asn Tyr Asn Pro Ile Thr Glu Lys
65                  70                  75                  80

His Val Asp Thr Gly Met Thr Leu Lys Glu Leu Ala Asp Ala Ser Leu
                85                  90                  95

Arg Tyr Ser Asp Asn Ala Ala Gln Asn Leu Ile Leu Lys Gln Ile Gly
            100                 105                 110

Gly Pro Glu Ser Leu Lys Lys Glu Leu Arg Lys Ile Gly Asp Glu Val
        115                 120                 125

Thr Asn Pro Glu Arg Phe Glu Pro Glu Leu Asn Glu Val Asn Pro Gly
    130                 135                 140

Glu Thr Gln Asp Thr Ser Thr Ala Arg Ala Leu Val Thr Ser Leu Arg
145                 150                 155                 160

Ala Phe Ala Leu Glu Asp Lys Leu Pro Ser Glu Lys Arg Glu Leu Leu
                165                 170                 175

Ile Asp Trp Met Lys Arg Asn Thr Thr Gly Asp Ala Leu Ile Arg Ala
            180                 185                 190

Gly Val Pro Asp Gly Trp Glu Val Gly Asp Lys Thr Gly Ser Gly Asp
        195                 200                 205

Tyr Gly Thr Arg Asn Asp Ile Ala Ile Ile Trp Pro Pro Lys Gly Asp
    210                 215                 220

Pro Val Val Leu Ala Val Leu Ser Ser Arg Asp Lys Lys Asp Ala Lys
225                 230                 235                 240

Tyr Asp Asn Lys Leu Ile Ala Glu Ala Thr Lys Val Val Met Lys Ala
                245                 250                 255

Leu Asn Met Asn Gly Lys
            260
```

<210> SEQ ID NO 6
<211> LENGTH: 299
<212> TYPE: PRT
<213> ORGANISM: Artificial Sequence
<220> FEATURE:
<223> OTHER INFORMATION: Synthetic sequence

<400> SEQUENCE: 6

```
Met Ile Gln Lys Arg Lys Arg Thr Val Ser Phe Arg Leu Val Leu Met
1               5                   10                  15
```

Cys Thr Leu Leu Phe Val Ser Leu Pro Ile Thr Lys Thr Ser Ala Gln
            20                  25                  30

Ala Ser Lys Thr Glu Met Lys Asp Asp Phe Ala Lys Leu Glu Glu Gln
        35                  40                  45

Phe Asp Ala Lys Leu Gly Ile Phe Ala Leu Asp Thr Gly Thr Asn Arg
    50                  55                  60

Thr Val Ala Tyr Arg Pro Asp Glu Arg Phe Ala Phe Ala Ser Thr Ile
65                  70                  75                  80

Lys Ala Leu Thr Val Gly Val Leu Leu Gln Gln Lys Ser Ile Glu Asp
                85                  90                  95

Leu Asn Gln Arg Ile Thr Tyr Thr Arg Asp Asp Leu Val Asn Tyr Asn
            100                 105                 110

Pro Ile Thr Glu Lys His Val Asp Thr Gly Met Thr Leu Lys Glu Leu
        115                 120                 125

Ala Asp Ala Ser Leu Arg Tyr Ser Asp Asn Ala Ala Gln Asn Leu Ile
    130                 135                 140

Leu Lys Gln Ile Gly Gly Pro Glu Ser Leu Lys Lys Glu Leu Arg Lys
145                 150                 155                 160

Ile Gly Asp Glu Val Thr Asn Pro Glu Arg Phe Glu Pro Glu Leu Asn
                165                 170                 175

Glu Val Asn Pro Gly Glu Thr Gln Asp Thr Ser Thr Ala Arg Ala Leu
            180                 185                 190

Val Thr Ser Leu Arg Ala Phe Ala Leu Glu Asp Lys Leu Pro Ser Glu
        195                 200                 205

Lys Arg Glu Leu Leu Ile Asp Trp Met Lys Arg Asn Thr Thr Gly Asp
    210                 215                 220

Ala Leu Ile Arg Ala Gly Val Pro Asp Gly Trp Glu Val Gly Asp Lys
225                 230                 235                 240

Thr Gly Ser Gly Asp Tyr Gly Thr Arg Asn Asp Ile Ala Ile Ile Trp
                245                 250                 255

Pro Pro Lys Gly Asp Pro Val Val Leu Ala Val Leu Ser Ser Arg Asp
            260                 265                 270

Lys Lys Asp Ala Lys Tyr Asp Asn Lys Leu Ile Ala Glu Ala Thr Lys
        275                 280                 285

Val Val Met Lys Ala Leu Asn Met Asn Gly Lys
    290                 295

<210> SEQ ID NO 7
<211> LENGTH: 900
<212> TYPE: DNA
<213> ORGANISM: Artificial Sequence
<220> FEATURE:
<223> OTHER INFORMATION: Synthetic sequence

<400> SEQUENCE: 7
atgattcaaa aacgaaagcg gacagtttcg ttcagacttg tgcttatgtg cacgctgtta      60
tttgtcagtt tgccgattac aaaaacatca gcgcaagctt ccaagacgga gatgaaagat     120
gattttgcaa aacttgagga acaatttgat gcaaaactcg ggatctttgc attggataca     180
ggtacaaacc ggacggtagc gtatcggccg gatgagcgtt ttgcttttgc ttcgacgatt     240
aaggctttaa ctgtaggcgt gcttttgcaa cagaaatcaa tagaagatct gaaccagaga     300
ataacatata cacgtgatga tcttgtaaac tacaacccga ttacggaaaa gcacgttgat     360
acgggaatga cgctcaaaga gcttgcggat gcttcgcttc gatatagtga caatgcggca     420
cagaatctca ttcttaaaca aattggcgga cctgaaagtt tgaaaaagga actgaggaag     480

```
attggtgatg aggttacaaa tcccgaacga ttcgaaccag agttaaatga agtgaatccg    540
ggtgaaactc aggataccag tacagcaaga gcacttgtca caagccttcg agcctttgct    600
cttgaagata aacttccaag tgaaaaacgc gagcttttaa tcgattggat gaaacgaaat    660
accactggag acgccttaat ccgtgccggt gtgccggacg gttgggaagt gggtgataaa    720
actggaagcg gagattatgg aacccggaat gacattgcca tcatttggcc gccaaaagga    780
gatcctgtcg ttcttgcagt attatccagc agggataaaa aggacgccaa gtatgataat    840
aaacttattg cagaggcaac aaaggtggta atgaaagcct taaacatgaa cggcaaataa    900
```

MICROBIOME PROTECTION FROM ORAL ANTIBIOTICS

PRIORITY

This application claims the benefit of U.S. Provisional Application No. 62/355,599, filed Jun. 28, 2016, the contents of which are hereby incorporated by reference herein in their entirety.

FIELD OF THE INVENTION

This invention relates to, in part, various compositions and methods for protecting the gastrointestinal microbiome from antibiotic disruption.

DESCRIPTION OF THE TEXT FILE SUBMITTED ELECTRONICALLY

The contents of the text file submitted electronically herewith are incorporated herein by reference in their entirety: a computer readable format copy of the Sequence Listing (filename: SYN-025PC_Sequence_listing_ST25.txt; date recorded: Jun. 27, 2017; file size: 13.6 KB).

BACKGROUND

The human microbiome is proving to be a vital component in both human health and disease. This is particularly true of the gastrointestinal (GI) tract, which houses over one thousand distinct bacterial species and an estimated excess of $1\times10^{11}$ microorganisms, and appears to be central in defining human host health status. For example, the microbiome of the GI tract underlies central processes of nutrient capture and metabolism; however, disruption of this microbiome is also believed to be causative of a number of disorders.

Indeed, antibiotics, often a frontline therapy to prevent deleterious effects of microbes on human health, can induce disruption in the microbiome, including in the GI tract, and lead to further disease. For instance, it is often necessary to administer oral antibiotics for the treatment of infections. However, residual oral antibiotics beyond what is needed for eradication of an infection can alter the ecological balance of normal intestinal microbiota in the gut and lead to further disease.

The present inventors previously described a beta-lactamase-based strategy to protect the microbiome from intravenously administered antibiotics. This strategy involves beta-lactamase delivery to the GI tract where it stands guard against intravenous antibiotics that may be excreted into the GI tract through, for instance, hepatobilliary excretion. Importantly, as the beta-lactamase is confined to the GI tract, it does not have systemic effects and therefore does not interfere with the desired anti-microbial effects of the intravenously administered antibiotic. However, this approach is more complicated when a patient is receiving orally administered antibiotics as both the beta-lactamase and the antibiotic directly transit though the GI tract and therefore, there is risk that the beta-lactamase may degrade the antibiotic and, despite protecting the microbiome, eliminate the desired systemic anti-microbial effect.

Therefore, there is a need for agents that prevent microbiome disruption by oral antibiotics while not reducing or eradicating the beneficial anti-infective effects of these antibiotics in a subject.

SUMMARY OF THE INVENTION

Accordingly, the present invention provides compositions and methods for protecting the gastrointestinal microbiome of a subject. In one aspect, methods for protecting the microbiome of the GI tract are provided in which an effective amount of a pharmaceutical composition comprising a beta-lactamase is administered to a subject who is undergoing treatment of has recently undergone treatment with an oral antibiotic, wherein the beta-lactamase is capable of deactivating the oral antibiotic. In an embodiment, the beta-lactamase does not substantially interfere with the plasma levels of a systemically absorbed orally administered antibiotic. In another embodiment, the beta-lactamase deactivates excess oral antibiotic residue excreted into the GI tract. In some embodiments, the beta-lactamase deactivates residual active antibiotic that is not absorbed from the GI tract after an oral dose or is returned in active form to the intestinal tract from the systemic circulation.

In various embodiments, the present invention provides a formulation that allows for release of beta-lactamase distal enough in the GI tract to allow for the absorption of an oral antibiotic and therefore prevents or substantially reduces the enzymatic activity of the beta-lactamase on the oral antibiotic before absorption (and therefore allows for or promotes the desired systemic antimicrobial effect). In various embodiments, the present formulations prevent or substantially reduce leakage of beta-lactamase proximal in the GI tract and thus prevent or substantially reduce interference with oral antibiotic absorption while still allowing beta-lactamase-based protection of the gut microbiome. In various embodiments, the present invention provides a formulation comprising a pellet comprising a beta-lactamase and various buffers and excipients described herein, where the pellet is coated with for example, FS EUDRAGIT® FS 30 D or EUDRAGIT® S100, and where the pellets are contained within a capsule which is itself is coated with for example, FS EUDRAGIT® FS 30 D or EUDRAGIT® S100. Accordingly, the present approach of coating pellets with the active beta-lactamase agent inside a coated capsule, sometimes referred to as "nesting," provides a secure manner to prevent beta-lactamase leakage too early in the GI tract during transit that the present inventors have found to be crucial to microbiome protection without antibiotic disruption.

Further, in various embodiments, the present invention provides a formulation comprising a pellet comprising a beta-lactamase and various buffers and excipients described herein, where the pellet is coated with for example, FS EUDRAGIT® FS 30 D or EUDRAGIT® S100, and where the pellets are contained within a small capsule (e.g. a capsule having a capsule body capacity of about 15 µL or less, e.g. a size 9 h capsule) which is itself is coated with for example, FS EUDRAGIT® FS 30 D and such loaded small capsules are in turn loaded in a larger capsule (e.g. a gelatin capsule), see, by way of non-limiting illustration, FIG. 26 and FIG. 28.

Further still, in various embodiments, the present invention provides the present formulations in combination with, or co-formulated with a beta-lactamase inhibitor, e.g. clavulanic acid, which helps overcome beta-lactamase catalytic effects too proximal in the GI tract to allow oral antibiotic anti-infective activity.

In various embodiments, the beta-lactamase is formulated for GI tract delivery. For example, the beta-lactamase may be enteric coated. In an embodiment, the beta-lactamase is formulated for release in a location in the GI tract in which it deactivates residual or excess oral antibiotic (e.g. residual active antibiotic that is not absorbed from the GI tract after an oral dose or is returned in active form to the intestinal tract from the systemic circulation). In another embodiment, the beta-lactamase is formulated for release in a location in which it prevents a microbicidal activity of the residual or excess oral antibiotic. In a further embodiment, the beta-lactamase is formulated for release in a location in the GI tract in which it does not substantially interfere with the systemic activity of the orally administered antibiotic. In another embodiment, the beta-lactamase is formulated for release in a location in the GI tract that is distal to the release and absorption of the orally administered antibiotic. In various embodiments, the beta-lactamase is formulated for substantially uniform dissolution in the area of release in the GI tract. In still further embodiments, the beta-lactamase is formulated for microorganism-based release in the GI tract.

In various embodiments, the present compositions and methods allow for oral antibiotic activity proximal in the GI tract (e.g. duodenum through the jejunum, inclusively). In various embodiments, the present compositions and methods allow for beta-lactamase-mediated protection of the microbiome of the GI tract via beta-lactamase catalytic activity in the ileum and below.

In various embodiments, the methods of the invention treat or prevent a microbiome-mediated disorder, such as an antibiotic-induced adverse effect, Clostridium difficile (C. difficile) infection, C. difficile-associated disease, ulcerative colitis, Crohn's disease, and irritable bowel syndrome. In an embodiment, the methods of the invention maintain the normal intestinal microbiota of a subject. For instance, in some embodiments, the methods of the invention maintain a healthy balance (e.g. a healthy ratio and/or healthy distribution) of intestinal microbiota of a subject. In another embodiment, the methods of the invention treat or prevent the overgrowth of one or more pathogenic microorganisms in the GI tract. In a further embodiment, the methods of the inventions find use in treating or preventing a nosocomial infection and/or a secondary emergent infection.

BRIEF DESCRIPTION OF THE FIGURES

FIG. 31 shows a list of formulations subjected to further testing in Examples 5-8.

DETAILED DESCRIPTION

Figure 1:
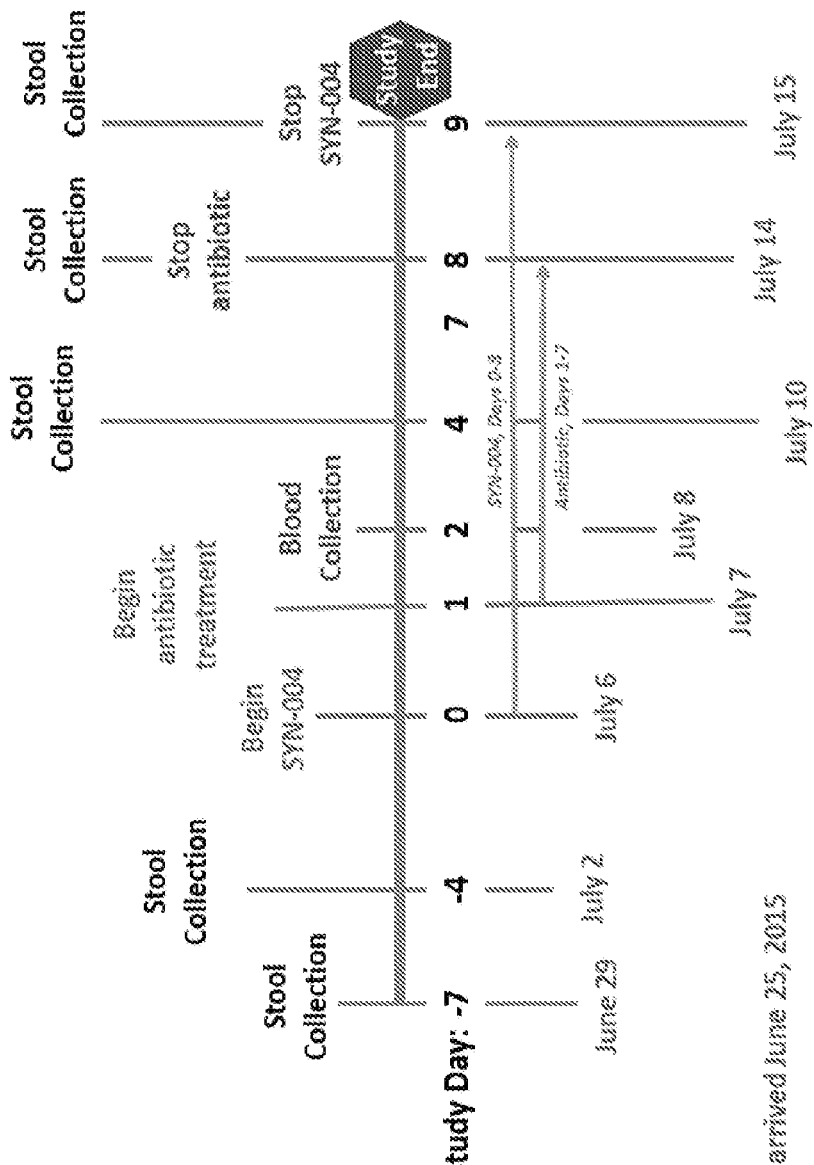
FIG. 1 shows a timeline of piglet dosing for the study of Example 1.

The present invention is based, in part, on the discovery that beta-lactamases can protect the gastrointestinal microbiome of a subject who is undergoing treatment or has undergone treatment with an oral antibiotic. Administration of oral antibiotics often disrupts the ecological balance of normal intestinal microbiota due to residual unabsorbed antibiotics being excreted into the intestines (e.g., the distal small intestine and/or the large intestine). Beta-lactamases inactivate the unabsorbed antibiotics in the GI tract thereby restoring and/or maintaining the normal intestinal microbiota and preventing any overgrowth of potentially pathogenic microorganisms. More specifically, the present inventors have discovered that small leakage of the protective beta-lactamases proximal in the GI tract (e.g. duodenum through the jejunum, inclusively) can degrade oral antibiotics and prevent anti-infective activity systemically.

Accordingly, in various embodiments, the present compositions and methods allow for beta-lactamase-mediated protection of the microbiome of the GI tract via beta-lactamase catalytic activity in the ileum and below through, for example, "nested" formulations of the beta-lactamases, optionally in the presence of a beta-lactamase inhibitor.

In some aspects, the present invention is based, in part, on the discovery that one or more beta-lactamases can be formulated to release in one or more locations within the GI tract at which the beta-lactamase inactivates (e.g. hydrolyzes) an orally delivered beta-lactam antibiotic and, in doing so, protects the microbiome, but the beta-lactamase does not interfere with intestinal absorption of the oral antibiotic and, accordingly, does not interfere with systemic blood or plasma levels of the oral antibiotic. The invention further identifies the location of such beta-lactamase release or activation. In various embodiments, the present formulations, which have an enterically coated beta-lactamase-containing pellet inside an enterically coated capsule, provide for minimal leakage of beta-lactamase-proximal in the GI tract and therefore preservation of oral antibiotic therapeutic effect while also providing maximal release distal in the GI tract to degrade residual oral antibiotic that could damage the microbiome.

Further, in some embodiments, the following two approaches may be employed separately or in combination: utilization of formulations designed to release beta-lactamase at the desired location in the GI tract and combining the antibiotic with an oral beta-lactamase inhibitor. In the latter, in some embodiments, the beta-lactamase inhibitor tracks with the beta-lactam antibiotic such that both are available for absorption in the proximal small intestine. The beta-lactamase inhibitor serves to protect the beta-lactam antibiotic from the beta-lactamase in the proximal small intestine. The antibiotic and the inhibitor are then both absorbed into the bloodstream and thereby removed from the proximal small intestine. As the concentration of inhibitor decreases in the small intestine, the beta-lactamase becomes active. Any residual or excess antibiotic that remains in the intestine or reenters with the bile will is inactivated prior to encountering the colonic microbiome.

In one aspect, the present invention relates to a method of protecting a subject's gastrointestinal (GI) microbiome from an oral antibiotic, comprising administering an effective amount of a formulation comprising a beta-lactamase capable of deactivating the oral antibiotic to a subject who is undergoing treatment or has recently undergone treatment with the oral antibiotic, wherein: the formulation comprises an enterically coated capsule comprising an enterically coated pellet, the pellet comprising, relative to a pellet's weight: about 20% to 25% sucrose sphere; about 30% to 40% binder excipient; about 12% to 18% beta-lactamase; about 1% to 2% buffer salts; about 0.5% to 3% plasticizer; about 15% to 30% EUDRAGIT® coating, and optionally about 0.5% to about 1.5% KH2PO4 and about 2.5% to 5% HPMC 603; and the capsule is coated with FS EUDRAGIT® FS 30 D.

In some embodiments, the EUDRAGIT® coating is selected from EUDRAGIT® FS 30 D or EUDRAGIT® S100.

In some embodiments, the capsule is coated with FS EUDRAGIT® FS 30 D at about 10% of the total capsule weight.

In some embodiments, the capsule has a body capacity of less than about 15 μL and is coated with FS EUDRAGIT® FS 30 D.

In some embodiments, the one or more capsules having body capacities of less than about 15 μL are loaded into a larger capsule.

In some embodiments, the capsule further comprises a beta-lactamase inhibitor, such as clavulanic acid.

In some embodiments, the binder excipient is hydroxypropylcellulose (HPC); and/or the beta-lactamase is selected from P1A, P2A, P3A, or P4A; and/or the plasticizer is triethyl citrate.

In some embodiments, the beta-lactamase is formulated for release in a location in the GI tract in which it does not substantially interfere with the systemic activity of the orally administered antibiotic.

In some embodiments, the beta-lactamase does not substantially interfere with plasma levels of a systemically absorbed orally administered antibiotic.

In some embodiments, the beta-lactamase deactivates residual oral antibiotic residue excreted into the GI tract, wherein the residual oral antibiotic is not absorbed from the GI tract after an oral dose or is returned in active form to the intestinal tract from the systemic circulation.

In some embodiments, the beta-lactamase is formulated for release in a location in the GI tract that is distal to the release of the orally administered antibiotic.

In some embodiments, the protection of the subject's microbiome comprises treatment or prevention of a microbiome-mediated disorder, e.g. ulcerative colitis, Crohn's disease, and irritable bowel syndrome, an antibiotic-induced adverse effect, *C. difficile* infection (CDI), *C. difficile*-associated disease (e.g. antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon).

In some embodiments, the protection of the subject's microbiome comprises maintenance of a normal intestinal microbiota.

In some embodiments, the method treats and/or prevents the overgrowth of one or more pathogenic microorganisms in the GI tract of a subject.

In some embodiments, the method treats or prevents a nosocomial infection and/or a secondary emergent infection.

Beta-Lactamases and Pharmaceutical Compositions

The present invention is directed, in part, to pharmaceutical compositions, formulations, and uses of one or more beta-lactamases. As used herein, a beta-lactamase refers to an enzyme, which deactivates beta-lactams. For example, the beta-lactamase may deactivate a beta-lactam by hydrolysis (e.g. hydrolysis of residual or excess antibiotic). Hydrolysis of the amide bond of the beta-lactam ring by the beta-lactamase makes an antimicrobial agent such as an antibiotic biologically inactive.

In various embodiments, the present invention is directed to compositions including one or more beta-lactamase enzyme of class EC 3.5.2.6. In some embodiments, the beta-lactamase is a group 1, 2, 3, or 4 beta-lactamase, in accordance with the functional classification scheme proposed by Bush et al. (1995, Antimicrob. Agents Chemother. 39: 1211-1233; the entire contents of which are incorporated herein by reference). Without wishing to be bound by theory, Group 1 beta-lactamases include cephalosporinases that are not well inhibited by clavulanic acid; Group 2 includes penicillinases, cephalosporinases and broad-spectrum beta-lactamases that are generally inhibited by active site-directed beta-lactamase inhibitors; Group 3 includes metallo-beta-lactamases that hydrolyze penicillins, cephalosporins and carbapenems, and that are poorly inhibited by almost all beta-lactam-containing molecules; and Group 4 includes penicillinases that are not well inhibited by clavulanic acid.

In some embodiments, the beta-lactamase is a class A, B, C, or D beta-lactamase, in accordance with the Ambler classification which divides beta-lactamases based on their amino acid sequences (Ambler 1980, Philos Trans R Soc Lond B Biol Sci. 289: 321-331; the entire contents of which are incorporated herein by reference). Without wishing to be bound by theory, classes A, C, and D beta-lactamases include evolutionarily distinct groups of serine beta-lactamases, and class B include the zinc-dependent ("EDTA-inhibited") beta-lactamases (see Ambler R. P. et al., 1991, Biochem J. 276: 269-270, the entire contents of which are incorporated herein by reference).

For example, in one embodiment, the beta-lactamase may be a class A enzyme which includes, but is not limited to, for example, KPC-1, KPC-2, KPC-3 and KPC-4. In another embodiment, the beta-lactamase may be a class B enzyme which includes, but is not limited to, for example, the IMP family, VIM family, GIM-1 and SPM-1 as well as others. In another embodiment, the beta-lactamase may be a class C enzyme such as an AmpC beta-lactamase. AmpC beta-lactamases hydrolyze broad and extended-spectrum cephalosporins (i.e., cephamycins and oxyimino-beta-lactams). In a further embodiment, the beta-lactamase may be a class D enzyme that includes, but is not limited to, for example, OXA-23, OXA-24, OXA-25, OXA-26, OXA-27, OXA-40 and OXA-40 as well as others. In some embodiments, the beta-lactamase may be an extended-spectrum beta-lactamase (ESBL), which hydrolyzes cephalosporins with an oxyimino chain. ESBLs include, but are not limited to, TEM, SHV, CTX-M, OXA, PER, VEB, GES, and IBC beta-lactamases. In other embodiments, the beta-lactamase may be an inhibitor-resistant β-lactamase, optionally selected from an AmpC-type β-lactamases, Carbapenemase, IMP-type carbapenemases (metallo-β-lactamases), VIMs (Verona integron-encoded metallo-β-lactamases), OXA (oxacillinase) group of β-lactamases, KPCs (*K. pneumonia* carbapenemases), CMY (Class C), SME, IMI, NMC, CcrA, and NDM (New Delhi metallo-β-lactamases, e.g. NDM-1) beta-lactamases.

In certain embodiments, the beta-lactamase is P1A, P2A, P3A or SYN-004 (synonyms for the same enzyme), or P4A. In an embodiment, the beta-lactamase is P1A or a derivative thereof. The P1A enzyme is a recombinant form of *Bacillus licheniformis* 749/C small exo beta-lactamase (see WO 2008/065247) which belongs to class A and is grouped to subgroup 2a in functional classification. *B. licheniformis* beta-lactamase and its P1A derivative are considered as penicillinases which have high hydrolytic capacity to degrade e.g. penicillin, ampicillin, amoxicillin or piperacillin and they are generally inhibited by active site-directed beta-lactamase inhibitors such as clavulanic acid, sulbactam or tazobactam. In another embodiment, the beta-lactamase is P2A or a derivative thereof as described, for example, in WO 2007/147945, the entire contents of which are incorporated herein by reference. The P2A enzyme belongs to class B and is a metallo-enzyme that requires one or two zinc ions as a cofactor for enzyme activity. In another embodiment, the beta-lactamase is P3A or a derivative thereof as described, for example, in WO 2011/148041 and U.S. Pat. No. 9,290,754, the entire contents of all of which are incorporated herein by reference. In a further embodiment, the beta-lactamase is P4A or a derivative thereof as described, for example, in U.S. Pat. No. 9,290,754, the entire contents of all of which are incorporated herein by reference.

For example, the beta-lactamase may have the sequence of *Bacillus licheniformis* PenP, i.e., P1A (SEQ ID NO: 1) or is derived by one or more mutations of SEQ ID NO: 1. Provided herein is the 263 amino acid sequence of P1A (after removal of a 31 amino acid signal sequence and the QASKT (Gln-Ala-Ser-Lys-Thr) pentapeptide at the N-terminus, see SEQ ID NO: 3). As described herein, mutations may be made to this sequence to generate beta-lactamase derivatives.

```
                                                SEQ ID NO: 1
Glu Met Lys Asp Asp Phe Ala Lys Leu Glu Glu Gln

Phe Asp Ala Lys Leu Gly Ile Phe Ala Leu Asp Thr

Gly Thr Asn Arg Thr Val Ala Tyr Arg Pro Asp Glu

Arg Phe Ala Phe Ala Ser Thr Ile Lys Ala Leu Thr

Val Gly Val Leu Leu Gln Gln Lys Ser Ile Glu Asp

Leu Asn Gln Arg Ile Thr Tyr Thr Arg Asp Asp Leu

Val Asn Tyr Asn Pro Ile Thr Glu Lys His Val Asp

Thr Gly Met Thr Leu Lys Glu Leu Ala Asp Ala Ser

Leu Arg Tyr Ser Asp Asn Ala Ala Gln Asn Leu Ile

Leu Lys Gln Ile Gly Gly Pro Glu Ser Leu Lys Lys

Glu Leu Arg Lys Ile Gly Asp Glu Val Thr Asn Pro

Glu Arg Phe Glu Pro Glu Leu Asn Glu Val Asn Pro

Gly Glu Thr Gln Asp Thr Ser Thr Ala Arg Ala Leu

Val Thr Ser Leu Arg Ala Phe Ala Leu Glu Asp Lys

Leu Pro Ser Glu Lys Arg Glu Leu Leu Ile Asp Trp

Met Lys Arg Asn Thr Thr Gly Asp Ala Leu Ile Arg

Ala Gly Val Pro Asp Gly Trp Glu Val Ala Asp Lys

Thr Gly Ala Ala Ser Tyr Gly Thr Arg Asn Asp Ile

Ala Ile Ile Trp Pro Pro Lys Gly Asp Pro Val Val

Leu Ala Val Leu Ser Ser Arg Asp Lys Lys Asp Ala

Lys Tyr Asp Asp Lys Leu Ile Ala Glu Ala Thr Lys

Val Val Met Lys Ala Leu Asn Met Asn Gly Lys.
```

In some embodiments, SEQ ID NO: 1 may have a Met and/or Thr preceding the first residue of the sequence. In various embodiments, the Met may be cleaved. As described herein, mutations may be made to the sequence comprising the Met and/or Thr preceding the first residue to generate beta-lactamase derivatives.

Also provided herein is the 299 amino acid sequence of P1A before removal of a 31 amino acid signal sequence and the QASKT (Gln-Ala-Ser-Lys-Thr) pentapeptide at the N-terminus as SEQ ID NO: 3:

```
                                                SEQ ID NO: 3
Met Ile Gln Lys Arg Lys Arg Thr Val Ser Phe Arg

Leu Val Leu Met Cys Thr Leu Leu Phe Val Ser Leu

Pro Ile Thr Lys Thr Ser Ala Gln Ala Ser Lys Thr

Glu Met Lys Asp Asp Phe Ala Lys Leu Glu Glu Gln
```

-continued

```
Phe Asp Ala Lys Leu Gly Ile Phe Ala Leu Asp Thr

Gly Thr Asn Arg Thr Val Ala Tyr Arg Pro Asp Glu

Arg Phe Ala Phe Ala Ser Thr Ile Lys Ala Leu Thr

Val Gly Val Leu Leu Gln Gln Lys Ser Ile Glu Asp

Leu Asn Gln Arg Ile Thr Tyr Thr Arg Asp Asp Leu

Val Asn Tyr Asn Pro Ile Thr Glu Lys His Val Asp

Thr Gly Met Thr Leu Lys Glu Leu Ala Asp Ala Ser

Leu Arg Tyr Ser Asp Asn Ala Ala Gln Asn Leu Ile

Leu Lys Gln Ile Gly Gly Pro Glu Ser Leu Lys Lys

Glu Leu Arg Lys Ile Gly Asp Glu Val Thr Asn Pro

Glu Arg Phe Glu Pro Glu Leu Asn Glu Val Asn Pro

Gly Glu Thr Gln Asp Thr Ser Thr Ala Arg Ala Leu

Val Thr Ser Leu Arg Ala Phe Ala Leu Glu Asp Lys

Leu Pro Ser Glu Lys Arg Glu Leu Leu Ile Asp Trp

Met Lys Arg Asn Thr Thr Gly Asp Ala Leu Ile Arg

Ala Gly Val Pro Asp Gly Trp Glu Val Ala Asp Lys

Thr Gly Ala Ala Ser Tyr Gly Thr Arg Asn Asp Ile

Ala Ile Ile Trp Pro Pro Lys Gly Asp Pro Val Val

Leu Ala Val Leu Ser Ser Arg Asp Lys Lys Asp Ala

Lys Tyr Asp Asp Lys Leu Ile Ala Glu Ala Thr Lys

Val Val Met Lys Ala Leu Asn Met Asn Gly Lys
```

Further, the beta-lactamase polypeptide may include additional upstream residues from the first residue of SEQ ID NO: 1 (see, e.g., JBC 258 (18): 11211, 1983, the contents of which are hereby incorporated by reference—including the exo-large and exo-small versions of penP and penP1). Further, the beta-lactamase polypeptide may also include additional downstream residues from the last residue of SEQ ID NO: 1.

The polynucleotide sequence of P1A (after removal of a 31 amino acid signal sequence and the QAKST pentapeptide at the N-terminus) is provided as SEQ ID NO: 2. As described herein, mutations may be made to this sequence to generate the beta-lactamase derivatives (including, taking into account degeneracy of the genetic code).

SEQ ID NO: 2
```
gagatgaaagatgattttgcaaaacttgaggaacaatttgatgcaaaa
ctcgggatctttgcattggatacaggtacaaaccggacggtagcgtat
cggccggatgagcgttttgcttttgcttcgacgattaaggctttaact
gtaggcgtgcttttgcaacagaaatcaatagaagatctgaaccagaga
ataacatatacacgtgatgatcttgtaaactacaacccgattacggaa
aagcacgttgatacgggaatgacgctcaaagagcttgcggatgcttcg
cttcgatatagtgacaatgcggcacagaatctcattcttaaacaaatt
ggcggacctgaaagtttgaaaaaggaactgaggaagattggtgatgag
gttacaaatcccgaacgattcgaaccagagttaaatgaagtgaatccg
ggtgaaactcaggataccagtacagcaagagcacttgtcacaagcctt
cgagcctttgctcttgaagataaacttccaagtgaaaaacgcgagctt
ttaatcgattggatgaaacgaaataccactggagacgccttaatccgt
gccggtgtgccggacggttgggaagtggctgataaaactggagcggca
tcatatggaacccggaatgacattgccatcatttggccgccaaaagga
gatcctgtcgttcttgcagtattatccagcagggataaaaaggacgcc
aagtatgatgataaacttattgcagaggcaacaaaggtggtaatgaaa
gccttaaacatgaacggcaaataa
```

Also provided is the polynucleotide sequence of P1A before the removal of a 31 amino acid signal sequence and the QASKT pentapeptide at the N-terminus as SEQ ID NO: 4. As described herein, mutations may be made to this sequence to generate beta-lactamase derivatives (including, taking into account degeneracy of the genetic code).

SEQ ID NO: 4
```
atgattcaaaaacgaaagcggacagtttcgttcagacttgtgcttatg
tgcacgctgttatttgtcagtttgccgattacaaaaacatcagcgcaa
gcttccaagacggagatgaaagatgattttgcaaaacttgaggaacaa
tttgatgcaaaactcgggatctttgcattggatacaggtacaaaccgg
acggtagcgtatcggccggatgagcgttttgcttttgcttcgacgatt
aaggctttaactgtaggcgtgcttttgcaacagaaatcaatagaagat
ctgaaccagagaataacatatacacgtgatgatcttgtaaactacaac
ccgattacggaaaagcacgttgatacgggaatgacgctcaaagagctt
gcggatgcttcgcttcgatatagtgacaatgcggcacagaatctcatt
cttaaacaaattggcggacctgaaagtttgaaaaaggaactgaggaag
attggtgatgaggttacaaatcccgaacgattcgaaccagagttaaat
gaagtgaatccgggtgaaactcaggataccagtacagcaagagcactt
gtcacaagccttcgagcctttgctcttgaagataaacttccaagtgaa
aaacgcgagcttttaatcgattggatgaaacgaaataccactggagac
gccttaatccgtgccggtgtgccggacggttgggaagtggctgataaa
actggagcggcatcatatggaacccggaatgacattgccatcatttgg
ccgccaaaaggagatcctgtcgttcttgcagtattatccagcagggat
aaaaaggacgccaagtatgatgataaacttattgcagaggcaacaaag
gtggtaatgaaagccttaaacatgaacggcaaataa
```

In some embodiments, mutagenesis of a beta-lactamase is performed to derive advantageous enzymes to be utilized by methods of the present invention (e.g. those that can target broad spectra of antibiotics). In some embodiments, beta-lactamase derivatives are obtained by site-directed mutagenesis, random mutagenesis, and/or directed evolution approaches. In some embodiments, mutation design is based on, inter alia, structural data (e.g. crystal structure data, homolog models, etc.) of the following: P1A crystal structure (Knox and Moews, J. Mol Biol., 220, 435-455 (1991)), CTX-M-44 (1BZA (Ibuka et al. *Journal of Molecular Biology* Volume 285, Issue 5 2079-2087 (1999), 1IYS (Ibuka et al. Biochemistry, 2003, 42 (36): 10634-43), 1IYO, 1IYP and 1IYQ (Shimamura et al. 2002 *J. Biol. Chem.* 277:46601-08),

*Proteus vulgaris* K1 (1HZO, Nugaka et al. *J Mol Biol.* 2002 Mar. 15; 317(1):109-17) and *Proteus penneri* HugA (Liassine et al. *Antimicrob Agents Chemother.* 2002 January; 46(1):216-9. 2002), and reviewed in Bonnet, *Antimicrob. Agents Chemother* 48(1): 1-14 (2004) (for CTM-X), the contents of all of which are herein incorporated by reference in their entirety). In some embodiments, the present mutations are informed by analysis of structural data (e.g. crystal structure data, homolog models, etc.) of any one of the following beta-lactamases: P1A (see, e.g. U.S. Pat. No. 5,607,671, the contents of which are hereby incorporated by reference), P2A (see, e.g., WO 2007/147945, the contents of which are hereby incorporated by reference), P3A (see, e.g., WO 2011/148041, the contents of which are hereby incorporated by reference), CTX-M-3, CTX-M-4, CTX-M-5, CTX-M-9, CTX-M-10, CTX-M-14, CTX-M-15, CTX-M-16, CTX-M-18, CTX-M-19, CTX-M-25, CTX-M-26, CTX-M-27, CTX-M-32, CTX-M-44, CTX-M-45, and CTX-M-54. Such information is available to one skilled in the art of known databases, for example, Swiss-Prot Protein Sequence Data Bank, NCBI, and PDB.

In some embodiments, the beta-lactamase includes one or more (e.g. about 1, or about 2, or about 3, or about 4, or about 5, or about 6, or about 7, or about 8, or about 9, or about 10, or about 15, or about 20, or about 30, or about 40, or about 50, or about 60, or about 70, or about 80, or about 90, or about 100, or about 110, or about 120, or about 130, or about 140, or about 150) mutations to SEQ ID NO: 1 or SEQ ID NO: 3 or a sequence with at least 30%, 35%, 40%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.8%, or 99.9% identity to SEQ ID NO: 1 or SEQ ID NO: 3 (or about 60%, about 65%, about 70%, about 75%, about 80%, about 85%, about 90%, about 95%, about 96%, about 97%, about 98%, or about 99% identity to SEQ ID NO: 1 or SEQ ID NO: 3).

In various embodiments, one or more amino acid of SEQ ID NO: 1 or SEQ ID NO: 3 is substituted with a naturally occurring amino acid, such as a hydrophilic amino acid (e.g. a polar and positively charged hydrophilic amino acid, such as arginine (R) or lysine (K); a polar and neutral of charge hydrophilic amino acid, such as asparagine (N), glutamine (Q), serine (S), threonine (T), proline (P), and cysteine (C), a polar and negatively charged hydrophilic amino acid, such as aspartate (D) or glutamate (E), or an aromatic, polar and positively charged hydrophilic amino acid, such as histidine (H)) or a hydrophobic amino acid (e.g. a hydrophobic, aliphatic amino acid such as glycine (G), alanine (A), leucine (L), isoleucine (I), methionine (M), or valine (V), a hydrophobic, aromatic amino acid, such as phenylalanine (F), tryptophan (W), or tyrosine (Y) or a non-classical amino acid (e.g. selenocysteine, pyrrolysine, N-formylmethionine β-alanine, GABA and 6-Aminolevulinic acid. 4-Aminobenzoic acid (PABA), D-isomers of the common amino acids, 2,4-diaminobutyric acid, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosme, citrulline, homocitrulline, cysteic acid, t-butylglycine, t-butylalanine, phenylglycine, cyclohexylalanine, β-alanine, fluoro-amino acids, designer amino acids such as p methyl amino acids, C α-methyl amino acids, N α-methyl amino acids, and amino acid analogs in general). In some embodiments, SEQ ID NO: 1 may have a Met and/or Thr preceding the first residue of the sequence. These residues may be similarly mutated as above.

Illustrative mutations are described in U.S. Pat. No. 9,290,754, the entire contents of all of which are incorporated herein by reference.

In all of the Class A beta-lactamase mutants, the numbering of residues corresponds to SEQ ID NO: 1. These residue numbers may be converted to Ambler numbers (Ambler et al., 1991, A standard numbering scheme for the Class A β-lactamases, *Biochem. J.* 276:269-272, the contents of which are hereby incorporated by reference) through use of any conventional bioinformatic method, for example by using BLAST (Basic Local Alignment Search Tools) or FASTA (FAST-All). For example, residue 244 corresponds to Ambler 276. For example, the following conversions may be used:

| Ambler Classification No. | SEQ ID NO: 1 Residue |
|---|---|
| F33 | F6 |
| I72 | I44 |
| Q135 | Q105 |
| G156 | G126 |
| T160 | T130 |
| A232 | A202 |
| A237 | A207 |
| A238 | A208 |
| S240 | S209 |
| T243 | T212 |
| R244 | R213 |
| S266 | S234 |
| D276 | D244 |

Furthermore, percent identity may also be assessed with these conventional bioinformatic methods.

In one embodiment, the beta-lactamase utilized by methods of the invention comprises an amino acid sequence having at least 60% (e.g. about 60%, or about 61%, or about 62%, or about 63%, or about 64%, or about 65%, or about 66%, or about 67%, or about 68%, or about 69%, or about 70%, or about 71%, or about 72%, or about 73%, or about 74%, or about 75%, or about 76%, or about 77%, or about 78%, or about 79%, or about 80%, or about 81%, or about 82%, or about 83%, or about 84%, or about 85%, or about 86%, or about 87%, or about 88%, or about 89%, or about 90%, or about 91%, or about 92%, or about 93%, or about 94%, or about 95%, or about 96%, or about 97%, or about 98%, or about 99%) sequence identity with SEQ ID NO: 1 or SEQ ID NO: 3 and one or more of the following mutations of Ambler classification: F33X, Q135X, G156X, A232X, A237X, A238X, S240X, T243X, R244X, S266X, and D276X, wherein X is any naturally-occurring amino acid and with the proviso that D276X is not present in the context of a single mutant. In some embodiments, X is a naturally occurring hydrophilic or hydrophobic amino acid residue or a non-classical amino acid.

In another embodiment, the beta-lactamase utilized by methods of the invention comprises an amino acid sequence having at least 60% sequence identity with SEQ ID NO: 1 or SEQ ID NO: 3 and one or more of the following mutations of Ambler classification: a hydrophobic residue other than phenylalanine (F) at position 33; a hydrophobic residue other than glutamine (Q) at position 135; a hydrophilic residue other than glycine (G) at position 156; a hydrophobic residue other than alanine (A) at position 232; a hydrophilic residue other than alanine (A) at position 237; a hydrophobic or hydrophilic residue other than alanine (A) at position 238; a hydrophilic residue other than serine (S)

at position 240; a hydrophobic residue other than threonine (T) at position 243; a hydrophobic residue other than arginine (R) at position 244; a hydrophilic residue other than serine (S) at position 266; and a hydrophilic residue other than aspartate (D) at position 276, with the proviso that hydrophilic amino acid residue other than aspartic acid (D) at a position corresponding to position 276 is not present in the context of a single mutant.

As used throughout, a hydrophilic amino acid residue may include a polar and positively charged hydrophilic residue selected from arginine (R) and lysine (K), a polar and neutral of charge hydrophilic residue selected from asparagine (N), glutamine (O), serine (S), threonine (T), proline (P), and cysteine (C), a polar and negatively charged hydrophilic residue selected from aspartate (D) and glutamate (E), or an aromatic, polar and positively charged hydrophilic including histidine (H). As used throughout, a hydrophobic amino acid residue may include a hydrophobic, aliphatic amino acid selected from glycine (G), alanine (A), leucine (L), isoleucine (1), methionine (M), or valine (V) or a hydrophobic, aromatic amino acid selected from phenylalanine (F), tryptophan (W), or tyrosine (Y).

Mutations may be made to the gene sequence of a beta-lactamase (e.g. SEQ ID NOs: 3 and 4) by reference to the genetic code, including taking into account codon degeneracy.

In some embodiments, the beta-lactamase utilized by methods of the invention comprises one or more of the following mutations at positions of Ambler classification: F33Y, Q135M, G156R, A232G, A237S, A238G or T, S240P or D, T2431, R244T, S266N, D276N or R or K, provided that D276N or R or K is not in the context of a single mutant. In one embodiment, the beta-lactamases comprise Q135M. In another embodiment, the beta-lactamases comprise G156R and A238T. In another embodiment, the beta-lactamases comprise F33Y and D276N. In still another embodiment, the beta-lactamases comprise F33Y, S240P, and D276N. In one embodiment, the beta-lactamases comprise F33Y, A238T, and D276N. In another embodiment, the beta-lactamases comprise A232G, A237S, A238G, and S240D. In a further embodiment, the beta-lactamases comprise A232G, A237S, A238G, S240D, and R244T. In another embodiment, the beta-lactamases comprise A232G, A237S, A238G, S240D, and D276R. In one embodiment, the beta-lactamases comprise A232G, A237S, A238G, S240D, and D276K. In one embodiment, the beta-lactamases comprise A232G, A237S, A238G, S240D, and Q135M. In one embodiment, the beta-lactamases comprise A238T. In one embodiment, the beta-lactamases comprise T2431, S266N, and D276N. In one embodiment, the beta-lactamases comprise A232G, A237S, A238G, S240D, and D276N.

In other embodiments, the beta-lactamases comprise an amino acid sequence having at least 60% sequence identity with SEQ ID NO: 1 or SEQ ID NO: 3 and the following of Ambler classification: a hydrophobic residue other than alanine (A) at position 232; a hydrophilic residue other than alanine (A) at position 237; a hydrophobic residue other than alanine (A) at position 238; a hydrophilic residue other than serine (S) at position 240; and a hydrophilic residue other than aspartate (D) at position 276. In some embodiments, the hydrophobic residue other than alanine (A) at position 232 is glycine (G). In some embodiments, the hydrophilic residue other than alanine (A) at position 237 is serine (S). In some embodiments, the hydrophobic residue other than alanine (A) at position 238 is glycine (G). In some embodiments, the hydrophilic residue other than serine (S) at position 240 is aspartate (D). In some embodiments, the other than aspartate (D) at position 276 is asparagine (N). In some embodiments, the beta-lactamase and/or pharmaceutical composition comprises one or more of A232G, A237S, A238G, S240D, and D276N. In some embodiments, the beta-lactamase comprises all of A232G, A237S, A238G, S240D, and D276N, the sequence of which is SEQ ID NO: 5:

```
                                              SEQ ID NO: 5
EMKDDFAKLEEQFDAKLGIFALDTGTNRTVAYRPDERFAFASTIKALT

VGVLLQQKSIEDLNQRITTRDDLVNYNPITEKHVDTGMTLKELADASL

RYSDNAAQNLILKQIGGPESLKKELRKIGDEVTNPERFEPELNEVNPG

ETQDTSTARALVTSLRAFALEDKLPSEKRELLIDWMKRNTTGDALIRA

GVPDGWEVGDKTGSGDYGTRNDIAIIWPPKGDPVVLAVLSSRDKKDAK

YDNKLIAEATKVVMKALNMNGK or
```

SEQ ID NO: 6 is derived from SEQ ID NO: 5, and further includes the signal and the addition of the QASKT amino acids:

```
                                              SEQ ID NO: 6
MIQKRKRTVSFRLVLMCTLLFVSLPITKTSAQASKTEMKDDFAKLEEQ

FDAKLGIFALDTGTNRTVAYRPDERFAFASTIKALTVGVLLQQKSIED

LNQRITYTRDDLVNYNPITEKHVDTGMTLKELADASLRYSDNAAQNLI

LKQIGGPESLKKELRKIGDEVTNPERFEPELNEVNPGETQDTSTARAL

VTSLRAFALEDKLPSEKRELLIDVVMKRNTTGDALIRAGVPDGVVEVG

DKTGSGDYGTRNDIAIIWPPKGDPVVLAVLSSRDKKDAKYDNKLIAEA

TKVVMKALNMNGK
```

An illustrative polynucleotide of the invention is SEQ ID NO: 7:

```
                                              SEQ ID NO: 7
Atgattcaaaaacgaaagcggacagtttcgttcagacttgtgcttatg tgcacgctgttatttgtcagtttgccgattacaaaaacatcagcgcaa gcttccaagacggagatgaaagatgattttgcaaaacttgaggaacaa tttgatgcaaaactcgggatctttgcattggatacaggtacaaaccgg acggtagcgtatcggccggatgagcgttttgcttttgcttcgacgatt aaggctttaactgtaggcgtgcttttgcaacagaaatcaatagaagat ctgaaccagagaataacatatacacgtgatgatcttgtaaactacaac ccgattacggaaaagcacgttgatacgggaatgacgctcaaagagctt gcggatgcttcgcttcgatatagtgacaatgcggcacagaatctcatt cttaaacaaattggcggacctgaaagtttgaaaaaggaactgaggaag attggtgatgaggttacaaatcccgaacgattcgaaccagagttaaat gaagtgaatccgggtgaaactcaggataccagtacagcaagagcactt gtcacaagccttcgagcctttgctcttgaagataaacttccaagtgaa aaacgcgagcttttaatcgattggatgaaacgaaataccactggagac gccttaatccgtgccggtgtgccggacggttgggaagtgggtgataaa actggaagcggagattatggaacccggaatgacattgccatcatttgg
```

-continued ccgccaaaaggagatcctgtcgttcttgcagtattatccagcagggat aaaaaggacgccaagtatgataataaacttattgcagaggcaacaaag gtggtaatgaaagccttaaacatgaacggcaaataa Full nucleotide sequence of A232G, A237S, A238G, S240D, and D276N mutant, Hind III site (AAGCTT—in bold) and additional K and T amino acids. The leader and additional nucleotides (Hind III site and K and T amino acids—for the addition of the amino acid sequence QASKT) are underlined.

Additional sequences of beta-lactamases including P1A, P2A, P3A, and P4A and derivatives thereof are described for example, in WO2011/148041 and U.S. Pat. No. 9,290,754, the entire contents of all of which are incorporated herein by reference. The following table lists representative beta-lactamases and their derivatives which can be utilized in methods of the present invention:

| Mutations relative to P1A (based on the Ambler classification) | Name |
| --- | --- |
| Wild type | RS310 (or P1A) |
| D276N | IS118 (or P3A) |
| I72S | IS222 |
| T160F | IS203 |
| R244T | IS217 |
| R244T D276K | IS215 |
| Q135M | IS197 |
| G156R A238T | IS235 |
| F33Y D276N | IS158 |
| F33Y S240P D276N | IS230 (or IS181) |
| F33Y A238T D276N | IS232 (or IS180) |
| I72S Q135M T160F (Block 1 mutants) | IS227 |
| A232G A237S A238G S240D (Block 2 mutants) | IS191 |
| A232G A237S A238G S240D R244T | IS229 |
| A232G A237S A238G S240D D276R | IS219 |
| A232G A237S A238G S240D D276K | IS221 |
| A232G A237S A238G S240D Q135M | IS224 |
| A238T | IS233 |
| T243I S266N D276N | IS234 (or IS176) |
| A232G A237S A238G S240D D276N | IS288 (or P4A) |

In various embodiments, the beta-lactamases possess desirable characteristics, including, for example, having an ability to efficiently target a broad spectra of antibiotics including oral antibiotics. In various embodiments, the beta-lactamases possess desirable enzyme kinetic characteristics. For example, in some embodiments, the beta-lactamases possess a low $K_M$ for at least one oral antibiotic, including, for example, a $K_M$ of less than about 500 µM, or about 100 µM, or about 10 µM, or about 1 µM, or about 0.1 µM (100 nM), or about 0.01 µM (10 nM), or about 1 nM. In various embodiments, the beta-lactamases possess a high $V_{max}$ for at least one oral antibiotic, including, for example, $V_{max}$ which is greater than about 100 s−1, or about 1000 s−1, or about 10000 s−1, or about 100000 s−1, or about 1000000 s−1. In various embodiments, the beta-lactamases possess catalytic efficiency that is greater than about $10^6$ $M^{-1}s^{-1}$ for at least one oral antibiotic.

In various embodiments, the beta-lactamases are stable and/or active in the GI tract, e.g. in one or more of the mouth, esophagus, stomach, duodenum, small intestine, duodenum, jejunum, ileum, large intestine, colon transversum, colon descendens, colon ascendens, colon sigmoidenum, cecum, and rectum. In a specific embodiment, the beta-lactamase is stable in the large intestine, optionally selected from one or more of colon transversum, colon descendens, colon ascendens, colon sigmoidenum and cecum. In a specific embodiment, the beta-lactamase is stable in the small intestine, optionally selected from one or more of duodenum, jejunum, and ileum. In some embodiments, the beta-lactamase is resistant to proteases in the GI tract, including for example, the small intestine. In some embodiments, the beta-lactamase is substantially active at a pH of about 6.0 to about 7.5, e.g. about 6.0, or about 6.1, or about 6.2, or about 6.3, or about 6.4, or about 6.5, or about 6.6, or about 6.7, or about 6.8, or about 6.9, or about 7.0, or about 7.1, or about 7.2, or about 7.3, or about 7.4, or about 7.5 (including, for example, via formulation, as described herein). In various embodiments, the beta-lactamases of the present invention are resistant to one or more beta-lactamase inhibitors, optionally selected from avibactam, tazobactam, sulbactam, and clavulanic acid. In other embodiments, as described herein the beta-lactamases of the present invention are susceptible to one or more beta-lactamase inhibitors and this property is exploited to ensure antibiotic hydrolysis does not interfere with the therapeutic benefit of the oral antibiotic. In some embodiments, stable refers to an enzyme that has a long enough half-life and maintains sufficient activity for therapeutic effectiveness.

In some embodiments, the beta-lactamases described herein, include derivatives that are modified, i.e., by the covalent attachment of any type of molecule to the beta-lactamase such that covalent attachment does not prevent the activity of the enzyme. For example, but not by way of limitation, derivatives include beta-lactamases that have been modified by, inter alia, glycosylation, lipidation, acetylation, pegylation, phosphorylation, amidation, derivatization by known protecting/blocking groups, proteolytic cleavage, linkage to a cellular ligand or other protein, etc. Any of numerous chemical modifications can be carried out, including, but not limited to specific chemical cleavage, acetylation, formylation, metabolic synthesis of tunicamycin, etc. Additionally, the derivative can contain one or more non-classical amino acids.

In still other embodiments, the beta-lactamases described herein may be modified to add effector moieties such as chemical linkers, detectable moieties such as for example fluorescent dyes, enzymes, substrates, bioluminescent materials, radioactive materials, and chemiluminescent moieties, or functional moieties such as for example streptavidin, avidin, biotin, a cytotoxin, a cytotoxic agent, and radioactive materials.

The beta-lactamases described herein can possess a sufficiently basic functional group, which can react with an inorganic or organic acid, or a carboxyl group, which can react with an inorganic or organic base, to form a pharmaceutically acceptable salt. A pharmaceutically acceptable acid addition salt is formed from a pharmaceutically acceptable acid, as is well known in the art. Such salts include the pharmaceutically acceptable salts listed in, for example, *Journal of Pharmaceutical Science*, 66, 2-19 (1977) and *The Handbook of Pharmaceutical Salts*; Properties, Selection, and Use. P. H. Stahl and C. G. Wermuth (eds.), Verlag, Zurich (Switzerland) 2002, which are hereby incorporated by reference in their entirety.

Pharmaceutically acceptable salts include, by way of non-limiting example, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, camphorsulfonate, pamoate, phenylacetate, trifluoroacetate, acrylate, chlorobenzoate, dinitrobenzoate, hydroxybenzoate, methoxybenzoate, methylbenzoate, o-acetoxybenzoate, naphthalene-2-benzoate, isobutyrate, phenylbutyrate, α-hydroxybutyrate, butyne-1,4-dicarboxylate, hexyne-1,4-dicarboxylate, caprate, caprylate, cinnamate, glycollate, heptanoate, hippurate, malate, hydroxymaleate, malonate, mandelate, mesylate, nicotinate, phthalate, teraphthalate, propiolate, propionate, phenylpropionate, sebacate, suberate, p-bromobenzenesulfonate, chlorobenzenesulfonate, ethylsulfonate, 2-hydroxyethylsulfonate, methylsulfonate, naphthalene-1-sulfonate, naphthalene-2-sulfonate, naphthalene-1,5-sulfonate, xylenesulfonate, and tartarate salts.

The term "pharmaceutically acceptable salt" also refers to a salt of the beta-lactamases having an acidic functional group, such as a carboxylic acid functional group, and a base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or tri-alkylamines, dicyclohexylamine; tributyl amine; pyridine; N-methyl, N-ethylamine; diethylamine; triethylamine; mono-, bis-, or tris-(2-OH-lower alkylamines), such as mono-; bis-, or tris-(2-hydroxyethyl)amine, 2-hydroxy-tert-butylamine, or tris-(hydroxymethyl)methylamine, N,N-di-lower alkyl-N-(hydroxyl-lower alkyl)-amines, such as N,N-dimethyl-N-(2-hydroxyethyl)amine or tri-(2-hydroxyethyl)amine; N-methyl-D-glucamine; and amino acids such as arginine, lysine, and the like.

In some embodiments, the compositions described herein are in the form of a pharmaceutically acceptable salt.

Further, any beta-lactamases described herein can be administered to a subject as a component of a composition that comprises a pharmaceutically acceptable carrier or vehicle. Such compositions can optionally comprise a suitable amount of a pharmaceutically acceptable excipient so as to provide the form for proper administration.

Pharmaceutical excipients can be liquids, such as water and oils, including those of petroleum, animal, vegetable, or synthetic origin, such as peanut oil, soybean oil, mineral oil, sesame oil and the like. The pharmaceutical excipients can be, for example, saline, gum acacia, gelatin, starch paste, talc, keratin, colloidal silica, urea and the like. In addition, auxiliary, stabilizing, thickening, lubricating, and coloring agents can be used. In one embodiment, the pharmaceutically acceptable excipients are sterile when administered to a subject. Water is a useful excipient when any agent described herein is administered intravenously. Saline solutions and aqueous dextrose and glycerol solutions can also be employed as liquid excipients, specifically for injectable solutions. Suitable pharmaceutical excipients also include starch, glucose, cellulose, hypromellose, lactose, sucrose, malt, rice, flour, chalk, silica gel, sodium stearate, glycerol monostearate, talc, sodium chloride, dried skim milk, glycerol, propylene, glycol, povidone, crosspovidone, water, ethanol and the like. Any agent described herein, if desired, can also comprise minor amounts of wetting or emulsifying agents, or pH buffering agents. Other examples of suitable pharmaceutical excipients are described in *Remington's Pharmaceutical Sciences* 1447-1676 (Alfonso R. Gennaro eds., 19th ed. 1995), incorporated herein by reference.

Where necessary, the beta-lactamases and/or pharmaceutical compositions (and/or additional therapeutic agents) can include a solubilizing agent. Also, the agents can be delivered with a suitable vehicle or delivery device. Compositions for administration can optionally include a local anesthetic such as, for example, lignocaine to lessen pain at the site of the injection. Combination therapies outlined herein can be co-delivered in a single delivery vehicle or delivery device.

Oral Antibiotics

In various embodiments, the beta-lactamases deactivate one or more oral antibiotics. In various embodiments, the beta-lactamases hydrolyze one or more oral antibiotics. In various embodiments, the described beta-lactamases and/or pharmaceutical compositions (and/or additional therapeutic agents) are formulated in a manner that preserves the therapeutic (e.g. systemic) action of one or more oral antibiotics while preventing the action of excess amounts these oral antibiotics lower in the GI tract, where they may disrupt the GI microbiota. For example, the described beta-lactamases and/or pharmaceutical compositions (and/or additional therapeutic agents) are formulated in a manner that active antibiotic that is not absorbed from the GI tract after an oral dose or is returned in active form to the intestinal tract from the systemic circulation is deactivated. In certain embodiments, the orally administered antibiotics are selected from penicillins, cephalosporins, monobactams, and carbapenems.

Penicillins include, for example, Amdinocillin, Amoxicillin (e.g. NOVAMOX, AMOXIL); Ampicillin (e.g. PRINCIPEN); Azlocillin; Carbenicillin (e.g. GEOCILLIN); Cloxacillin (e.g. TEGOPEN); Cyclacillin, Dicloxacillin (e.g. DYNAPEN); Flucloxacillin (e.g. FLOXAPEN); Mezlocillin (e.g. MEZLIN); Methicillin (e.g. STAPHCILLIN); Nafcillin (e.g. UNIPEN); Oxacillin (e.g. PROSTAPHLIN); Penicillanic Acid, Penicillin G (e.g. PENTIDS or PFIZERPEN); Penicillin V (e.g. VEETIDS (PEN-VEE-K)); Piperacillin (e.g. PIPRACIL); Sulbactam, Temocillin (e.g. NEGABAN); and Ticarcillin (e.g. TICAR).

Illustrative penicillins include:

| Generic | Brand Name |
|---|---|
| Amoxicillin | AMOXIL, POLYMOX, TRIMOX, WYMOX |
| Ampicillin | OMNIPEN, POLYCILLIN, POLYCILLIN-N, PRINCIPEN, TOTACILLIN |
| Bacampicillin | SPECTROBID |
| Carbenicillin | GEOCILLIN, GEOPEN |
| Cloxacillin | CLOXAPEN |
| Dicloxacillin | DYNAPEN, DYCILL, PATHOCIL |
| Flucloxacillin | FLOPEN, FLOXAPEN, STAPHCILLIN |
| Mezlocillin | MEZLIN |
| Nafcillin | NAFCIL, NALLPEN, UNIPEN |
| Oxacillin | BACTOCILL, PROSTAPHLIN |
| Penicillin G | BICILLIN L-A, CRYSTICILLIN 300 A.S., PENTIDS, PERMAPEN, PFIZERPEN, PFIZERPEN-AS, WYCILLIN |
| Penicillin V | BEEPEN-VK, BETAPEN-VK, LEDERCILLIN VK, V-CILLIN K |
| Piperacillin | PIPRACIL |
| Pivampicillin | |
| Pivmecillinam | |
| Ticarcillin | TICAR |

Cephalosporins include, for example, a first generation cephalosporin (e.g. Cefadroxil (e.g. DURICEF); Cefazolin (e.g. ANCEF); Ceftolozane, Cefalotin/Cefalothin (e.g. KEFLIN); Cefalexin (e.g. KEFLEX); a second generation cephalosporin (e.g. Cefaclor (e.g. DISTACLOR); Cefamandole (e.g. MANDOL); Cefoxitin (e.g. MEFOXIN); Cefprozil (e.g. CEFZIL); Cefuroxime (e.g. CEFTIN, ZINNAT)); a third generation cephalosporin (e.g. Cefixime (e.g. SUPRAX); Cefdinir (e.g. OMNICEF, CEFDIEL); Cefditoren (e.g. SPECTRACEF); Cefoperazone (e.g. CEFOBID); Cefotaxime (e.g. CLAFORAN); Cefpodoxime (e.g. VANTIN); Ceftazidime (e.g. FORTAZ); Ceftibuten (e.g. CEDAX) Ceftizoxime (e.g. CEFIZOX); and Ceftriaxone (e.g. ROCEPHIN)); a fourth generation cephalosporin (e.g. Cefepime (e.g. MAXIPIME)); or a fifth generation cephalosporin (e.g. Ceftaroline fosamil (e.g. TEFLARO); Ceftobiprole (e.g. ZEFTERA)). Also included is Latamoxef (or moxalactam). In a specific embodiment, cephalosporins include, for example, cefoperazone, ceftriaxone or cefazolin.

Illustrative cephalosporins include

| Generic | Brand Name |
| --- | --- |
| First Generation | |
| Cefacetrile (cephacetrile) | CELOSPOR, CELTOL, CRISTACEF |
| Cefadroxil (cefadroxyl) | DURICEF, ULTRACEF |
| Cefalexin (cephalexin) | KEFLEX, KEFTAB |
| Cefaloglycin (cephaloglycin) | KEFGLYCIN |
| Cefalonium (cephalonium) | |
| Cefaloridine (cephaloradine) | |
| Cefalotin (cephalothin) | KEFLIN |
| Cefapirin (cephapirin) | CEFADYL |
| Cefatrizine | |
| Cefazaflur | |
| Cefazedone | |
| Cefazolin (cephazolin) | ANCEF, KEFZOL |
| Cefradine (cephradine) | VELOSEF |
| Cefroxadine | |
| Ceftezole | |
| Second Generation | |
| Cefaclor | CECLOR, CECLOR CD, DISTACLOR, KEFLOR, RANICOR |
| Cefamandole | MANDOL |
| Cefmetazole | |
| Cefonicid | MONOCID |
| Cefotetan | CEFOTAN |
| Cefoxitin | MEFOXIN |
| Cefprozil (cefproxil) | CEFZIL |
| Cefuroxime | CEFTIN, KEFUROX, ZINACEF, ZINNAT |
| Cefuzonam | |
| Third Generation | |
| Cefcapene | |
| Cefdaloxime | |
| Cefdinir | OMNICEF, CEFDIEL |
| Cefditoren | SPECTRACEF |
| Cefetamet | |
| Cefixime | SUPRAX |
| Cefmenoxime | CEFMAX |
| Cefodizime | |
| Cefotaxime | CLAFORAN |
| Cefpimizole | |
| Cefpodoxime | VANTIN |
| Cefteram | |
| Ceftibuten | CEDAX |
| Ceftiofur | EXCEDE |
| Ceftiolene | |
| Ceftizoxime | CEFIZOX |
| Ceftriaxone | ROCEPHIN |
| Cefoperazone | CEFOBID |
| Ceftazidime | CEPTAZ, FORTUM, FORTAZ, TAZICEF, TAZIDIME |

| Generic | Brand Name |
| --- | --- |
| Fourth Generation | |
| Cefclidine | |
| Cefepime | MAXIPIME |
| Cefluprenam | |
| Cefoselis | |
| Cefozopran | |
| Cefpirome | CEFROM |
| Cefquinome | |
| Fifth Generation | |
| Ceftobiprole | ZEFTERA |
| Ceftaroline | TEFLARO |
| Not Classified | |
| Cefaclomezine | |
| Cefaloram | |
| Cefaparole | |
| Cefcanel | |
| Cefedrolor | |
| Cefempidone | |
| Cefetrizole | |
| Cefivitril | |
| Cefmatilen | |
| Cefmepidium | |
| Cefovecin | |
| Cefoxazole | |
| Cefrotil | |
| Cefsumide | |
| Cefuracetime | |
| Ceftioxide | |

Monobactams include, for example, aztreonam (e.g. AZACTAM, CAYSTON), tigemonam, nocardicin A, and tabtoxin.

Carbapenems include, for example, meropenem, imipenem (by way of non-limiting example, imipenem/cilastatin), ertapenem, doripenem, panipenem/betamipron, biapenem, razupenem (PZ-601), tebipenem, lenapenem, and tomopenem. Carbapenems also include thienamycins.

Illustrative carbapenems include

| Generic | Brand Name |
| --- | --- |
| Imipenem, Imipenem/cilastatin | PRIMAXIN |
| Doripenem | DORIBAX |
| Meropenem | MERREM |
| Ertapenem | INVANZ |

Beta-Lactamase Inhibitors

In various embodiments, the described beta-lactamases and/or pharmaceutical compositions (and/or additional therapeutic agents) are formulated in a manner that preserves the therapeutic (e.g. systemic) action of one or more oral antibiotics while preventing the action of residual or excess amounts these oral antibiotics (e.g. active antibiotic that is not absorbed from the GI tract after an oral dose or is returned in active form to the intestinal tract from the systemic circulation) lower in the GI tract, where they may disrupt the GI microbiota and this dual purpose is effected, in part, by use of one or more beta-lactamase inhibitor.

For example, the described beta-lactamases may be administered in a patient that receives one or more beta-lactamase inhibitors (e.g. sequential or simultaneous co-administration, or co-formulation) such that the one or more beta-lactamase inhibitors act to protect the oral antibiotics higher in the GI tract (e.g. ileum and above, or the proximal small intestine) by reducing or eliminating beta-lactamase activity. However, the one or more beta-lactamase inhibitors do not have such inhibitory effects on beta-lactamase activity lower in the GI tract (e.g. distal small intestine and/or the colon) and therefore allow the described beta-lactamase to deactivate (e.g. hydrolyze) residual or excess oral antibiotic lower in the GI tract and thus prevent or mitigate damage to the GI microbiota.

In some embodiments, the beta-lactamase inhibitor tracks with the beta-lactam antibiotic such that both are available for absorption in the proximal small intestine. The beta-lactamase inhibitor serves to protect the beta-lactam antibiotic from the beta-lactamase in the proximal small intestine. The antibiotic and the inhibitor are then both absorbed into the bloodstream and thereby removed from the proximal small intestine. As the concentration of inhibitor decreases in the small intestine, the beta-lactamase becomes active. Any residual or excess antibiotic that remains in the intestine or re-enters with the bile will is inactivated prior to encountering the colonic microbiome.

In some embodiments, the beta-lactamase inhibitor includes, for example, tazobactam, sulbactam, clavulanic acid, avibactam, monobactam derivatives, ATMO derivatives, penems (e.g., BRL42715 and derivatives thereof, Syn1012, oxapenems, trinems, 1-β-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phophonates, NXL104, hydroxmates) and metallo-β-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates. Co-formulations of an oral antibiotic with one or more beta-lactamase inhibitors are also provided in some embodiments (e.g. Augmentin is a mixture of amoxicillin and clavulanic acid; Sultamicillin is a mixture of ampicillin and sulbactam).

Further, any of the beta-lactamase inhibitors described in Drawz, Clin Microbiol Rev. January 2010; 23(1): 160-201, the contents of which are hereby incorporated by reference in their entirety, are encompassed by the present invention.

Formulations and Administration

In various embodiments, the present invention provides a formulation that allows for release of beta-lactamase distal enough in the GI tract to allow for the absorption of an oral antibiotic and therefore prevents or substantially reduces the enzymatic activity of the beta-lactamase on the oral antibiotic before absorption (and therefore allows for or promotes the desired systemic antimicrobial effect). In various embodiments, the present formulations prevent or substantially reduce leakage of beta-lactamase proximal in the GI tract and thus prevent or substantially reduce interference with oral antibiotic absorption. In various embodiments, the present invention provides a formulation comprising a pellet comprising a beta-lactamase and various buffers and excipients described herein, where the pellet is coated with for example, FS EUDRAGIT® FS 30 D or EUDRAGIT® S100, and where the pellets are contained within a capsule which is itself coated in for example, FS EUDRAGIT® FS D. Accordingly, the present approach of coating pellets with the active beta-lactamase agent inside a coated capsule provides a secure manner to prevent beta-lactamase leakage too early in the GI tract during transit that the present inventors have found to be crucial to microbiome protection without antibiotic disruption.

The present invention includes the described beta-lactamases and/or pharmaceutical compositions (and/or additional therapeutic agents) in various formulations. Any beta-lactamase and/or pharmaceutical composition (and/or additional therapeutic agents) described herein can take the form of solutions, suspensions, emulsion, drops, tablets, pills, pellets, capsules, capsules containing liquids, capsules containing multiparticulates, powders, suppositories, emulsions, aerosols, sprays, suspensions, delayed-release formulations, sustained-release formulations, controlled-release formulations, or any other form suitable for use. In one embodiment, the composition is in the form of a capsule or a tablet (see, e.g., U.S. Pat. No. 5,698,155).

The formulations comprising the beta-lactamases and/or pharmaceutical compositions (and/or additional therapeutic agents) may conveniently be presented in unit dosage forms. For example, the dosage forms may be prepared by methods which include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by press tableting)

In one embodiment, the beta-lactamases (and/or additional therapeutic agents) described herein is formulated as a composition adapted for a mode of administration described herein.

In some embodiments, the administration the beta-lactamases and/or pharmaceutical compositions (and/or additional therapeutic agents) is any one of oral, intravenous, and parenteral. In some embodiments, the administration of the beta-lactamases and/or pharmaceutical compositions (and/or additional therapeutic agents) is not intravenous in order to, for example, prevent interference with an antibiotic administered systemically. In other embodiments, routes of administration include, for example: oral, intradermal, intramuscular, intraperitoneal, intravenous, subcutaneous, intranasal, epidural, sublingual, intranasal, intracerebral, intravaginal, transdermal, rectally, by inhalation, or topically, particularly to the ears, nose, eyes, or skin. In some embodiments, the administering is effected orally or by parenteral injection.

In various embodiments, the administration the beta-lactamases and/or pharmaceutical compositions (and/or additional therapeutic agents) is into the GI tract via, for example, oral delivery, nasogastral tube, intestinal intubation (e.g. an enteral tube or feeding tube such as, for example, a jejunal tube or gastro-jejunal tube, etc.), endoscopy, colonoscopy, or enema.

In an embodiment, the beta-lactamases and/or pharmaceutical compositions (and/or additional therapeutic agents) described herein can be administered orally. In other embodiments, the beta-lactamases and/or pharmaceutical compositions (and/or additional therapeutic agents) can also be administered by any other convenient route, for example, by intravenous infusion or bolus injection, by absorption through epithelial or mucocutaneous linings (e.g., oral mucosa, rectal and intestinal mucosa, etc.) and can be administered together with an additional therapeutic agent. Administration can be systemic or local. In some embodiments, administration is not at the site of infection to avoid, for example, hydrolysis of an antibiotic at the site of infection. Various delivery systems are known, e.g., encapsulation in liposomes, microparticles, microcapsules, capsules, etc., and can be used for administration.

In specific embodiments, it may be desirable to administer locally to the area in need of treatment.

In one embodiment, the beta-lactamases and/or pharmaceutical compositions (and/or additional therapeutic agents) described herein is formulated as a composition adapted for oral administration to humans. Compositions for oral delivery can be in the form of tablets, lozenges, aqueous or oily suspensions, granules, powders, sprinkles, emulsions, capsules, syrups, or elixirs, for example. Orally administered compositions can comprise one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration to provide a sustained action over an extended period of time. Selectively permeable membranes surrounding an osmotically active agent driving any beta-lactamases (and/or additional therapeutic agents) described herein are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be useful. Oral compositions can include standard excipients such as mannitol, lactose, starch, magnesium stearate, sodium saccharin, cellulose, ethacrylic acid and derivative polymers thereof, and magnesium carbonate. In one embodiment, the excipients are of pharmaceutical grade. Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

In various embodiments, the beta-lactamases and/or pharmaceutical compositions (and/or additional therapeutic agent) are formulated as solid dosage forms such as tablets, dispersible powders, granules, and capsules. In one embodiment, the beta-lactamases and/or pharmaceutical compositions (and/or additional therapeutic agent) are formulated as a capsule. In another embodiment, the beta-lactamases and/or pharmaceutical compositions (and/or additional therapeutic agent) are formulated as a tablet. In yet another embodiment, the beta-lactamases and/or pharmaceutical compositions (and/or additional therapeutic agent) are formulated as a soft-gel capsule. In a further embodiment, the beta-lactamases and/or pharmaceutical compositions (and/or additional therapeutic agent) are formulated as a gelatin capsule.

Dosage forms suitable for parenteral administration (e.g. intravenous, intramuscular, intraperitoneal, subcutaneous and intra-articular injection and infusion) include, for example, solutions, suspensions, dispersions, emulsions, and the like. They may also be manufactured in the form of sterile solid compositions (e.g. lyophilized composition), which can be dissolved or suspended in sterile injectable medium immediately before use. They may contain, for example, suspending or dispersing agents.

Various methods may be used to formulate and/or deliver the agents described herein to a location of interest. For example, the beta-lactamases and/or pharmaceutical compositions (and/or additional therapeutic agents) described herein may be formulated for delivery to the gastrointestinal tract. The gastrointestinal tract includes organs of the digestive system such as mouth, esophagus, stomach, duodenum, small intestine, large intestine and rectum and includes all subsections thereof (e.g. the small intestine may include the duodenum, jejunum and ileum; the large intestine may include the colon transversum, colon descendens, colon ascendens, colon sigmoidenum and cecum). For example, the beta-lactamases and/or pharmaceutical compositions (and/or additional therapeutic agents) described herein may be formulated for delivery to one or more of the stomach, small intestine, large intestine and rectum and includes all subsections thereof (e.g. duodenum, jejunum and ileum, colon transversum, colon descendens, colon ascendens, colon sigmoidenum and cecum). In some embodiments, the compositions described herein may be formulated to deliver to the upper or lower GI tract. In an embodiment, the beta-lactamases and/or pharmaceutical compositions (and/or additional therapeutic agents) may be administered to a subject, by, for example, directly or indirectly contacting the mucosal tissues of the gastrointestinal tract.

For example, in various embodiments, the present invention provides modified release formulations comprising at least one beta-lactamase (and/or additional therapeutic agents), wherein the formulation releases a substantial amount of the beta-lactamase (and/or additional therapeutic agents) into one or more regions of the GI tract. For example, the formulation may release at least about 60% of the beta-lactamase after the stomach and into one or more regions of the GI tract. In various embodiments, the modified release formulations comprising at least one beta-lactamase (and/or additional therapeutic agents) are released in a manner that allows for the therapeutic (e.g. systemic) activity of one or more oral antibiotic (and/or a beta-lactamase inhibitor) but prevents or mitigates the deleterious effects of residual or excess oral antibiotics on the microbiota of the GI tract (e.g. active antibiotic that is not absorbed from the GI tract after an oral dose or is returned in active form to the intestinal tract from the systemic circulation). In various embodiments, the modified release formulations comprising at least one beta-lactamase (and/or additional therapeutic agents) are released distal to the release of one or more oral antibiotic (and/or a beta-lactamase inhibitor). For example, in various embodiments, the modified release formulations comprising at least one beta-lactamase (and/or additional therapeutic agents) are released distal to the ileum and below. For example, in various embodiments, the modified release formulations comprising at least one beta-lactamase (and/or additional therapeutic agents) are released is released in the distal small intestine and/or the colon.

In various embodiments, the modified-release formulation of the present invention releases at least 60% of the beta-lactamase (or additional therapeutic agents) after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the intestine.

In various embodiments, the modified-release formulation of the present invention releases at least 60% of the beta-lactamase (or additional therapeutic agents) in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the small intestine.

In one embodiment, the modified-release formulation of the present invention releases at least 60% of the beta-lactamase (or additional therapeutic agents) in the duodenum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the duodenum.

In one embodiment, the modified-release formulation of the present invention releases at least 60% of the beta-lactamase (or additional therapeutic agents) in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the jejunum.

In one embodiment, the modified-release formulation of the present invention releases at least 60% of the beta-lactamase (or additional therapeutic agents) in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the ileum and/or the ileocecal junction.

In various embodiments, the modified-release formulation of the present invention releases at least 60% of the beta-lactamase (or additional therapeutic agents) in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the large intestine.

In one embodiment, the modified-release formulation of the present invention releases at least 60% of the beta-lactamase (or additional therapeutic agents) in the cecum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the cecum.

In one embodiment, the modified-release formulation of the present invention releases at least 60% of the beta-lactamase (or additional therapeutic agents) in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the ascending colon.

In one embodiment, the modified-release formulation of the present invention releases at least 60% of the beta-lactamase (or additional therapeutic agents) in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the transverse colon.

In one embodiment, the modified-release formulation of the present invention releases at least 60% of the beta-lactamase (or additional therapeutic agents) in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the descending colon.

In one embodiment, the modified-release formulation of the present invention releases at least 60% of the beta-lactamase (or additional therapeutic agents) in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the beta-lactamase (or additional therapeutic agents) in the sigmoid colon.

In various embodiments, the modified-release formulation does not substantially release the beta-lactamase (or additional therapeutic agents) in the stomach.

In certain embodiments, the modified-release formulation releases the beta-lactamase (or additional therapeutic agents) at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.7 or less, or about 6.5 or less, or about 6.2 or less or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In an embodiment, the modified-release formulation is substantially unstable at a pH of greater than about 6.2. In another embodiment, the modified-release formulation is substantially unstable at a pH of greater than about 6.7. In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the beta-lactamase and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the beta-lactamase and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total beta-lactamase and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the beta-lactamase and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the beta-lactamase and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of beta-lactamase and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

In various embodiments, the modified-release formulations comprising a beta-lactamase are substantially stable in chyme. For example, there is, in some embodiments, a loss of less than about 50% or about 40%, or about 30%, or about 20%, or about 10% of beta-lactamase activity in about 10, or 9, or 8, or 7, or 6, or 5, or 4, or 3, or 2, or 1 hour from administration.

In various embodiments, the modified-release formulation of the present invention may utilize one or more modified-release coatings such as delayed-release coatings to provide for effective, delayed yet substantial delivery of the beta-lactamase to the GI tract together with, optionally, additional therapeutic agents. In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly(methacrylic acid, methylmethacrylate), hydroxypropyl methylcellulose acetate succinate, cellulose acetate trimellitate, shellac or other suitable enteric coating polymers. The EUDRAGIT®-type polymer include, for example, EUDRAGIT® FS 30D, L 30 D-55, L 100-55, L 100, L 12.5, L 12.5 P, RL 30 D, RL PO, RL 100, RL 12.5, RS 30 D, RS PO, RS 100, RS 12.5, NE 30 D, NE 40 D, NM 30 D, S 100, S 12.5, and S 12.5 P. In some embodiments, one or more of EUDRAGIT® FS 30D, L 30 D-55, L 100-55, L 100, L 12.5, L 12.5 P RL 30 D, RL PO, RL 100, RL 12.5, RS 30 D, RS PO, RS 100, RS 12.5, NE 30 D, NE 40 D, NM 30 D, S 100, S 12.5 and S 12.5 P is used. The enteric agent may be a combination of the foregoing solutions or dispersions.

In one embodiment, the modified-release formulation may include one or more delayed-release coating(s) which remain essentially intact, or may be essentially insoluble, in gastric fluid. The stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

By way of non-limiting example, there are various EUDRAGIT® formulations that dissolve at rising pH, with formulations that dissolve at pH >5.5 (EUDRAGIT® L30 D-550), pH >6.0 (EUDRAGIT® L12, 5), and pH >7.0 (EUDRAGIT® FS 30D). Since the ileum has the highest pH in the small intestine, ranging from 7.3 to 7.8, the use of EUDRAGIT® FS 30D to coat the pellet containing the antibiotic-degrading enzyme, may delay the dissolution of the pellet until it reaches the ileum thereby localizing the release of the antibiotic-degrading enzyme to the ileum. However, the jejunum has a pH ranging from 6.6 to 7.4, therefore, the release may initiate in some patients in the jejunum, if the pH is at 7.0 or above. In such embodiments, the antibiotic-degrading enzyme may be delivered with an antibiotic/inhibitor combination as described. The different types of EUDRAGIT® can be combined with each other, or multiple different types of EUDRAGIT® coatings can be combined to fine tune the dissolution profile to achieve targeted delivery to achieve excellent function. For example, EUDRAGIT® L100, EUDRAGIT® S100, and triethyl citrate may be mixed together at a ratio of, for example, about 72.7/18.2/9.1, to form a coating that substantially releases at a pH of greater than about 6.2. In another example, EUDRAGIT® L100, EUDRAGIT® S100, and triethyl citrate may be mixed together at a ratio of, for example, about 30/60.9/9, to form a coating that substantially releases at a pH of greater than about 6.7. In a further example, DUO-COAT (KUECEPT) that uses two coatings of enteric polymers (like EUDRAGIT®), an outer layer, and an inner layer of partially neutralized enteric polymer and a buffer agent. The DUOCOAT technology allows more rapid release of the therapeutic agent initiated at the targeted pH compared to a single coating of the enteric polymer (Liu et al., 2010, European J. Pharmaceutics and Biopharmaceuticals 47:311, the entire contents of all of which are incorporated herein by reference). Release was demonstrated to be targeted to the ileum and/or ileoceacal junction in 10 healthy volunteers (Varum et al., 2013, European J. Pharmaceutics and Biopharmaceuticals 84:573, the entire contents of all of which are incorporated herein by reference).

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT® RS, EUDRAGIT® RL, and EUDRAGIT® NE. Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000) or pectin. In an embodiment, the present invention contemplates the use of a delayed-release coating that degrade as a function of time which comprises a swell layer comprising croscarmellos sodium and hydroxyproplycellulose. In such embodiment, the formulation may further include an osmotic rupture coating that comprises ethylcellulose such as ethylcellulose dispersions.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora. For example, in various embodiments, the delayed-release coating may be degraded by a microbial enzyme present in the gut flora. In an embodiment, the delayed-release coating may be degraded by a bacteria present in the small intestine. In another embodiment, the delayed-release coating may be degraded by a bacteria present in the large intestine.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified release formulation is designed for release in the colon. Various colon-specific delivery approaches may be utilized. For example, the modified release formulation may be formulated using a colon-specific drug delivery system (CODES) as described for example, in Li et al., AAPS PharmSciTech (2002), 3(4): 1-9, the entire contents of which are incorporated herein by reference. Drug release in such a system is triggered by colonic microflora coupled with pH-sensitive polymer coatings. For example, the formulation may be designed as a core tablet with three layers of polymer. The first coating is an acid-soluble polymer (e.g., EUDRAGIT® E), the outer coating is enteric, along with an hydroxypropyl methylcellulose barrier layer interposed in between. In another embodiment, colon delivery may be achieved by formulating the beta-lactamase (and/or additional therapeutic agent) with specific polymers that degrade in the colon such as, for example, pectin. The pectin may be further gelled or cross-linked with a cation such as a zinc cation. In an embodiment, the formulation is in the form of ionically crosslinked pectin beads which are further coated with a polymer (e.g., EUDRAGIT® polymer). Additional colon specific formulations include, but are not limited to, pressure-controlled drug delivery systems (prepared with, for example, ethylcellulose) and osmotic controlled drug delivery systems (i.e., ORDS-CT).

Formulations for colon specific delivery of beta-lactamases (and/or additional therapeutic agents), as described herein, may be evaluated using, for example, in vitro dissolution tests. For example, parallel dissolution studies in different buffers may be undertaken to characterize the behavior of the formulations at different pH levels. Alternatively, in vitro enzymatic tests may be carried out. For example, the formulations may be incubated in fermenters containing suitable medium for bacteria, and the amount of drug released at different time intervals is determined. Drug release studies can also be done in buffer medium containing enzymes or rat or guinea pig or rabbit cecal contents and the amount of drug released in a particular time is determined. In a further embodiment, in vivo evaluations may be carried out using animal models such as dogs, guinea pigs, rats, and pigs. Further, clinical evaluation of colon specific drug delivery formulations may be evaluated by calculating drug delivery index (DDI) which considers the relative ratio of RCE (relative colonic tissue exposure to the drug) to RSC (relative amount of drug in blood i.e. that is relative systemic exposure to the drug). Higher drug DDI indicates better colon drug delivery. Absorption of drugs from the colon may be monitored by colonoscopy and intubation.

In various embodiments, the present formulation provide for substantial uniform dissolution of the beta-lactamase (and/or additional therapeutic agent) in the area of release in the GI tract. In an embodiment, the present formulation minimizes patchy or heterogeneous release of the beta-lactamase. For example, when releasing in the distal small intestine or, especially the colon, the distribution of beta-lactamase (and/or additional therapeutic agent) may be heterogeneous and therefore require formulation to minimize local effects.

In some embodiments, a dual pulse formulation is provided. In various embodiments, the present invention provides for modified-release formulations that release multiple doses of the beta-lactamase, at different locations along the intestines, at different times, and/or at different pH. In an illustrative embodiment, the modified-release formulation comprises a first dose of the beta-lactamase and a second dose of the beta-lactamase, wherein the first dose and the second dose are released at different locations along the intestines, at different times, and/or at different pH. For example, the first dose is released at the duodenum, and the second dose is released at the ileum. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the beta-lactamase at different locations along the intestines, at different times, and/or at different pH. Further the dual pulse description herein applies to modified-release formulations that release a beta-lactamase and an additional therapeutic agent.

In some embodiments, a dual pulse formulation is provided in which a dose of the beta-lactamase and a dose of an oral antibiotic (and/or a beta-lactamase inhibitor) are released at different locations along the intestines, at different times, and/or at different pH. For example, the dose of an oral antibiotic (and/or a beta-lactamase inhibitor) is released proximal to the dose of the beta-lactamase. For example, the dose of an oral antibiotic (and/or a beta-lactamase inhibitor) is released in the ileum and upstream and the dose of the beta-lactamase is released in the distal small intestine and/or the colon.

In various embodiments, the invention provides a formulation comprising: a core particle having a base coat comprising one or more beta-lactamases, and a delayed-release coating disposed over the coated core particle. The delayed-release coating may be substantially stable in acidic environments and/or gastric fluid, and/or substantially unstable in near neutral to alkaline environments or intestinal fluid thereby exposing the coated core particle to intestinal fluid. The base coat comprising one or more beta-lactamases may further comprise one or more additional therapeutic agents. Optionally a plurality of base coats may be applied to the core particle each of which may contain a beta-lactamase and/or an additional therapeutic agent. In an embodiment, the core particle includes sucrose.

In an embodiment, a beta-lactamases can be sprayed onto an inert core (e.g., a sucrose core or a cellulose core such as a microcrystalline sucrose or cellulose core) and spray-dried with an enteric layer to form beta-lactamase containing pellets or beads. In various embodiments, the enteric layer may comprise one or more enteric agents as described herein. For example, the enteric layer may comprise an EUDRAGIT®-type polymer such as EUDRAGIT® L30 D-55, as described for example, in PCT/US2015/054606, the entire disclosure of which is hereby incorporated by reference. In such an embodiment, the formulation comprising the beta-lactamase containing pellets or beads may release the beta-lactamase at a pH of about 5.5.

In various embodiments, the present formulations provide a beta-lactamase-containing particle, which is coated for release in the distal GI tract, and which is inside a capsule which is also coated for release in the distal GI tract.

Optionally, the core particle may comprise one or more beta-lactamases and/or one or more additional therapeutic agents. In one embodiment, one or more doses of the beta-lactamase may be encapsulated in a core particle, for example, in the form of a microsphere or a mini-sphere. For example, the beta-lactamase may be combined with a polymer (e.g., latex), and then formed into a particulate, micro-encapsulated enzyme preparation, without using a sucrose core. The microspheres or mini-spheres thus formed may be optionally covered with a delayed-release coating.

A variety of approaches for generating particulates (such as microspheres, mini-spheres, aggregates, other) may be utilized for the inclusion of enzymatic proteins. They typically involve at least two phases, one containing the protein, and one containing a polymer that forms the backbone of the particulate. Most common are coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form, for example, microspheres or mini-spheres. Alternatively, the beta-lactamase and stabilizing excipients (for example, trehalose, mannitol, Tween 80, polyvinyl alcohol) are combined and sprayed from aqueous solution and collected. The particles are then suspended in a dry, water immiscible organic solvent containing polymer and release modifying compounds, and the suspension sonicated to disperse the particles. An additional approach uses aqueous phases but no organic solvent. Specifically, the enzymatic protein, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. When the release modifiers are insoluble at acidic conditions but soluble at higher pHs (such as carboxylic acid) then release from the matrix is inhibited in the gastric environment. In an embodiment, the beta-lactamase may be initially solubilized as an emulsion, microemulsion, or suspension and then formulated into solid mini-spheres or microspheres. The formulation may then be coated with, for example, a delayed-release, sustained-release, or controlled-release coating to achieve delivery at a specific location such as, for example, the intestines.

In various embodiments, the formulation may comprise a plurality of modified-release particles or beads or pellets or microspheres. In an embodiment, the formulation is in the form of capsules comprising multiple beads.

In another embodiment, the formulation is in the form of capsules comprising multiple pellets. In another embodiment, the formulation is in the form of capsules comprising multiple microspheres or mini-spheres. In some embodiments, before applying the delayed-release coating to the coated core particle, the particle can optionally be covered with one or more separating layers comprising pharmaceutical excipients including alkaline compounds such as for instance pH-buffering compounds. The separating layer essentially separates the coated core particle from the delayed-release coating.

The separating layer can be applied to the coated core particle by coating or layering procedures typically used with coating equipment such as a coating pan, coating granulator or in a fluidized bed apparatus using water and/or organic solvents for the coating process. As an alternative the separating layer can be applied to the core material by using a powder coating technique. The materials for separating layers are pharmaceutically acceptable compounds such as, for instance, sugar, polyethylene glycol, polyvinylpyrrolidone, polyvinyl alcohol, polyvinyl acetate, hydroxypropyl cellulose, methyl-cellulose, ethylcellulose, hydroxypropyl methylcellulose, carboxymethylcellulose sodium and others, used alone or in mixtures. Additives such as plasticizers, colorants, pigments, fillers, anti-tacking and anti-static agents, such as for instance magnesium stearate, sodium stearyl fumarate, titanium dioxide, talc and other additives can also be included in the separating layer.

In some embodiments, the coated particles with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

In various embodiments, the formulation may comprise a plurality of modified-release particles or pellets or microspheres. In one embodiment, the formulation is in the form of capsules comprising multiple pellets. In one embodiment, the formulation is in the form of capsules comprising multiple microspheres.

In some embodiments, the modified-release formulation is a capsule filled with a plurality of beta-lactamase-containing pellets (e.g., P3A (or the other beta-lactamase agents described herein, and variants thereof)-containing pellets) from which the beta-lactamase is released. In an embodiment, the capsule is a gelatin capsule, such as a hard gelatin capsule. In another embodiment, the capsule is a hydroxypropyl methylcellulose (HPMC) capsule. For example, the formulation may be in the form of capsules comprising multiple pellets. For example, the formulation may be in the form of capsules such as, for example, gelatin or hydroxypropyl methylcellulose (HPMC) capsules comprising multiple enteric-coated pellets containing beta-lactamase (e.g. P3A, or the other beta-lactamase agents described herein, and variants thereof). In another example, the formulation may be in the form of capsules such as, for example, gelatin or hydroxypropyl methylcellulose (HPMC) capsules comprising multiple pellets containing beta-lactamase (e.g. P3A, or the other beta-lactamase agents described herein, and variants thereof) coated with an osmotic-rupture coating. In such embodiments, a combination of pellets may be utilized in which each pellet is designed to release at a specific time point or location. In various embodiments, the pellets (e.g., enteric-coated pellets) are designed to pass through the stomach unchanged and then release the beta-lactamase (e.g. P3A, or the other beta-lactamase agents described herein, and variants thereof) into one or more regions of the intestines. In some embodiments, the beta-lactamase-containing pellets may be enteric-coated to release the beta-lactamase (e.g. P3A, or the other beta-lactamase agents described herein, and variants thereof) at different intestinal pH values. In some embodiments, the beta-lactamase-containing pellets may be coated with an osmotic-rupture coating to release the beta-lactamase (e.g. P3A, or the other beta-lactamase agents described herein, and variants thereof) within specific time frames.

In various embodiments, the formulation of the present invention is in the form of a capsule (e.g., a hard gelatin or HPMC capsule), which is enteric coated (e.g. with (e.g., EUDRAGIT® FS 30 D), and comprises a plurality of enteric-coated beta-lactamase-containing pellets. In such embodiments, the pellets (or each individual pellet) comprise a beta-lactamase (e.g. P3A, or the other beta-lactamase agents described herein, and variants thereof) and a sucrose sphere, which the beta-lactamase, for example, P3A or a variant, is sprayed onto, a coating comprising for example one or more enteric polymers, and/or additional excipients and/or buffer salts. In such embodiments, the pellets (or each individual pellet) comprise a beta-lactamase (e.g. P3A, or the other beta-lactamase agents described herein, and variants thereof), a sucrose sphere, which the beta-lactamase, for example, P3A or a variant, is sprayed onto, a binder excipient (e.g., hydroxypropylcellulose (HPC)), an enteric coating (e.g., EUDRAGIT® FS 30 D or EUDRAGIT® S100), and, optionally: a plasticizer (e.g., triethyl citrate), a glidant (e.g., glyceryl monostearate), an emulsifier, and a buffer salt. In various embodiments, the enteric coating comprises one or more of EUDRAGIT® FS 30 D, EUDRAGIT® S100, Duocoat FS 30 D (inner 5% ($K_2HPO_4$ and HPMC 603 buffer layer) and outer FS 30 D 20% dry polymer weight gain) and Duocoat S100.

In some embodiments, the present pellets are loaded into one or more small capsules, which are enteric coated (e.g. with (e.g., EUDRAGIT® FS 30 D), and such small capsules are loaded into a larger capsule. In some embodiments, the small capsule has a capsule body capacity of about 15 µL or less, e.g. about 15 µL, or about 14.5 µL, or about 14 µL, or about 13.5 µL, or about 13 µL, or about 12.5 µL, or about 12 µL, or about 10 µL. In some embodiments, the small capsule is a size 9H capsule.

In some embodiments, the present invention employs ENTRINSIC drug delivery technology (CAPSUGEL) to provide oral delivery with full enteric protection and rapid release in the upper gastrointestinal (GI) tract without the use of coatings.

As used herein, the term "EUDRAGIT®" refers to polymethacrylate-based copolymers as are known in the art (see, e.g., Expert Opin Drug Deliv. 2013 January; 10(1): 131-49, the entire contents of which are hereby incorporated by reference). The term includes anionic, cationic, and neutral copolymers based on methacrylic acid and methacrylic/acrylic esters or their derivatives.

EUDRAGIT® FS 30D refers to an aqueous dispersion with 30% dry substance. The dispersion contains 0.3% Sodium Laurilsulfate Ph. Eur./NF and 1.2% Polysorbate 80 Ph. Eur./NF on solid substance, as emulsifiers. EUDRAGIT® FS 30 D is the aqueous dispersion of an anionic copolymer based on methyl acrylate, methyl methacrylate and methacrylic acid. The ratio of the free carboxyl groups to the ester groups is approx. 1:10.

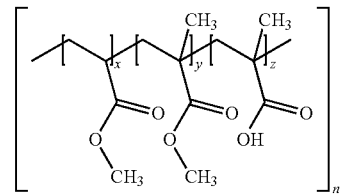

The monomers are randomly distributed along the copolymer chain. Based on SEC method the weight average molar mass (Mw) of EUDRAGIT® FS 30 D is approx. 280,000 g/mol.

EUDRAGIT® S 100 is an anionic copolymer based on methacrylic acid and methyl methacrylate. The ratio of the free carboxyl groups to the ester groups is approx. 1:2.

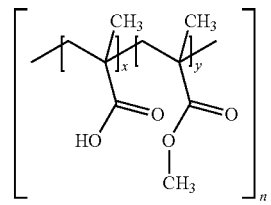

The monomers are randomly distributed along the copolymer chain. Based on SEC method the weight average molar mass (Mw) of EUDRAGIT® L 100 and EUDRAGIT® S 100 is approximately 125,000 g/mol.

In some embodiments, the present formulations comprise a layered pellet, the layered pellet comprising a sucrose sphere, hydroxypropylcellulose, P3A, and buffer salts, and the layered pellet is covered with a pellet coating.

In some embodiments, the present formulations comprise capsule which is covered with a capsule coating and a layered pellet, the layered pellet comprising a sucrose sphere, hydroxypropylcellulose, P3A, and buffer salts, and the layered pellet is covered with a pellet coating.

In some embodiments, the present formulations comprise a layered pellet, the layered pellet comprising a sucrose sphere, hydroxypropylcellulose, P3A, and buffer salts, and the layered pellet is covered with a pellet coating.

In some embodiments, the pellet is within an enterically-coated capsule (e.g., with FS EUDRAGIT® FS 30 D, e.g. at about 7%, or about 8%, or about 9%, or about 10%, or about 11% or about 12%, or about 15% of the total capsule, including pellet(s), weight) and comprises, relative to weight of a pellet: about 20% to 30% sucrose sphere (e.g. about 20%, or about 21%, or about 22%, or about 23%, or about 24%, or about 25%, or about 26%, or about 27%, or about 28%, or about 29%, or about 30%); about 30% to 40% binder excipient (e.g., hydroxypropylcellulose (HPC), e.g., about 30%, or about 31%, or about 32%, or about 33%, or about 34%, or about 35%, or about 36%, or about 37%, or about 38%, or about 39%, or about 40%); about 13% to 18% beta-lactamase (e.g. P3A, e.g., about 13%, or about 14%, or about 15%, or about 16%, or about 17%, or about 18%), about 1% to 2% buffer salts (e.g., about 1%, or about 1.1%, or about 1.2%, or about 1.3%, or about 1.4%, or about 1.5%, or about 1.6%, or about 1.7%, or about 1.8%, or about 1.9%, or about 2%); and about 15% to 35% pellets coating (e.g. FS EUDRAGIT® FS 30 D and/or EUDRAGIT® S100, e.g., about 15%, or about 16%, or about 17%, or about 18%, or about 19%, or about 20%, or about 21%, or about 22%, or about 23%, or about 24%, or about 25%, or about 26%, or about 27%, or about 28%, or about 29%, or about 30%, or about 31%, or about 32%, or about 33%, or about 34%, or about 35%.

In some embodiments, the pellet is within an enterically-coated capsule (e.g. with FS EUDRAGIT® FS 30 D) and comprises:

or about 22%, or about 23%, or about 24%, or about 25%) sucrose sphere; about 30% to 40% (e.g. about 30% or about 31%, or about 32%, or about 33%, or about 34%, or about 35%, or about 36%, or about 37%, or about 38%, or about 39%, or about 40%) binder excipient (e.g., hydroxypropylcellulose (HPC)); about 12% to 18% (e.g. about 12% or about 13%, or about 14%, or about 15%, or about 16%, or about 17%, or about 18%) beta-lactamase (e.g. P3A); about 1% to 2% (e.g., about 1%, or about 1.1%, or about 1.2%, or about 1.3%, or about 1.4%, or about 1.5%, or about 1.6%, or about 1.7%, or about 1.8%, or about 1.9%, or about 2%) buffer salts; about 0.5% to 3% (e.g. about 0.5%, or about 1%, or about 1.5%, or about 2%, or about 2.5%, or about 3%) plasticizer (e.g., triethyl citrate); about 15% to 30% (e.g. about 15%, or about 17.5%, or about 20%, or about 22.5%, or about 25%, or about 27.5%, or about 30%) EUDRAGIT® coating, e.g. EUDRAGIT® FS 30 D or EUDRAGIT® S100, and, optionally about 0.5% to about 1.5% (e.g. about 0.5%, or about 7.5%, or about 1%, or about 1.25%, or about 1.5%) KH$_2$PO$_4$; and about 2.5% to 5% (e.g. about 2.5%, or about 3%, or about 3.5%, or about 4%, or about 4.5%, or about 5%) HPMC 603.

| Component | F1 | % | F2 | % | F3 | % | F4 | % | F5 | % |
|---|---|---|---|---|---|---|---|---|---|---|
| Layered pellets | | | | | | | | | | |
| Sucrose sphere | 19.5 | 25.5% | 19.5 | 25.5% | 19.5 | 21.4% | 19.5 | 21.4% | 19.5 | 23.8% |
| Hydroxypropylcellulose | 29.3 | 38.3% | 29.3 | 38.3% | 29.3 | 32.1% | 29.3 | 32.1% | 29.3 | 35.8% |
| P3A | 13.2 | 17.2% | 13.2 | 17.2% | 13.2 | 14.5% | 13.2 | 14.5% | 13.2 | 16.1% |
| Buffer Salts | 1.3 | 1.7% | 1.3 | 1.7% | 1.3 | 1.4% | 1.3 | 1.4% | 1.3 | 1.6% |
| Subtotal | 63.3 | 82.6% | 63.3 | 82.6% | 63.3 | 69.4% | 63.3 | 69.4% | 63.3 | 77.3% |
| Pellets coating | 13.3 | 17.4% | 13.3 | 17.4% | 27.9 | 30.6% | 27.9 | 30.6% | 18.6 | 22.7% |
| Total | 76.6 | 100.0% | 76.6 | 100.0% | 91.2 | 100.0% | 91.2 | 100.0% | 81.9 | 100.0% |

In some embodiments, the present formulation is one of those presented in the following TABLE A and/or as described in the Examples herein (including, without limitation FIG. 31 and TABLE 18):

TABLE A

| Component | F1 | F2 | F3 | F4 | F5 |
|---|---|---|---|---|---|
| Layered pellets | | | | | |
| Sucrose sphere | | | 19.50 mg | | |
| Hydroxypropylcellulose | | | 29.30 mg | | |
| P3A | | | 13.20 mg | | |
| Buffer Salts | | | 1.3 mg | | |
| Subtotal | | | 63.3 mg | | |
| Pellets coating | 13.3 mg | 13.3 mg | 27.9 mg | 27.9 mg | 18.6 mg |
| Subtotal | 76.6 mg | 76.6 mg | 91.2 mg | 91.2 mg | 81.9 mg |
| Size 4 Gelatin capsule | — | 42.0 mg | — | 42.0 mg | — |
| Size 4 DRcap | 43.1 mg | — | 43.1 mg | — | 43.1 mg |
| Capsule coating | | | 13.6 mg | | |
| Subtotal | 56.7 mg | 55.6 mg | 56.7 mg | 55.6 mg | 56.7 mg |
| Total | 133.3 mg | 132.2 mg | 147.9 mg | 146.8 mg | 138.6 mg |

In some embodiments, the pellet is within an enterically-coated capsule (e.g., with FS EUDRAGIT® FS 30 D, e.g. at about 7%, or about 8%, or about 9%, or about 10%, or about 11% or about 12%, or about 15% of the total capsule, including pellet(s), weight) and comprises, relative to weight of a pellet: about 20% to 25% (e.g. about 20% or about 21%, In some embodiments, the pellet is within an enterically-coated capsule (e.g., with FS EUDRAGIT® FS 30 D, e.g. at about 7%, or about 8%, or about 9%, or about 10%, or about 11% or about 12%, or about 15% of the total capsule, including pellet(s), weight) and comprises, relative to weight of a pellet: about 25% sucrose sphere; about 40% hydroxypropylcellulose; about 20% beta-lactamase (e.g. P3A); about 2% buffer salts; about 15% EUDRAGIT® FS 30 D (dry polymer); and about 1% triethyl citrate.

In some embodiments, the pellet is within an enterically-coated capsule (e.g., with FS EUDRAGIT® FS 30 D, e.g. at about 7%, or about 8%, or about 9%, or about 10%, or about 11% or about 12%, or about 15% of the total capsule, including pellet(s), weight) and comprises, relative to weight of a pellet: about 20% sucrose sphere; about 30% hydroxypropylcellulose; about 15% beta-lactamase (e.g. P3A); about 1% buffer salts; about 30% EUDRAGIT® S100; and about 2.5% triethyl citrate.

In some embodiments, the pellet is within an enterically-coated capsule (e.g., with FS EUDRAGIT® ES 30 D, e.g. at about 7%, or about 8%, or about 9%, or about 10%, or about 11% or about 12%, or about 15% of the total capsule, including pellet(s), weight) and comprises, relative to weight of a pellet: about 25% sucrose sphere; about 35% hydroxypropylcellulose; about 15% beta-lactamase (e.g. P3A); about 2% buffer salts; about 15% EUDRAGIT® FS 30 D (dry polymer); about 1% triethyl citrate; about 1% Duocoat inner layer: $KH_2PO_4$; and about 5% Duocoat inner layer: HPMC 603.

In some embodiments, the present formulation is one of those presented in the following Table B and/or as described in the Examples herein (including, without limitation FIG. 31 and TABLE 18

TABLE B

| Component | F1 | % | F2 | % | F3 | % | F4 | % | F5 | % |
|---|---|---|---|---|---|---|---|---|---|---|
| (all units in mg unless noted) | | | | | | | | | | |
| Layered pellets | | | | | | | | | | |
| Sucrose sphere | 19.50 | 25.5% | 19.50 | 25.5% | 19.50 | 21.4% | 19.50 | 21.4% | 19.50 | 23.8% |
| Hydroxypropylcellulose | 29.30 | 38.3% | 29.30 | 38.3% | 29.30 | 32.1% | 29.30 | 32.1% | 29.30 | 35.8% |
| P3A | 13.20 | 17.2% | 13.20 | 17.2% | 13.20 | 14.5% | 13.20 | 14.5% | 13.20 | 16.1% |
| Buffer Salts | 1.3 | 1.7% | 1.3 | 1.7% | 1.3 | 1.4% | 1.3 | 1.4% | 1.3 | 1.6% |
| Subtotal | 63.3 | 82.6% | 63.3 | 82.6% | 63.3 | 69.4% | 63.3 | 69.4% | 63.3 | 77.3% |
| Pellets coating | | | | | | | | | | |
| EUDRAGIT FS 30 D (dry polymer) | 12.7 | 16.6% | 12.7 | 16.6% | 0 | 0.0% | 0 | 0.0% | 13.8 | 16.8% |
| EUDRAGIT S100 | 0 | 0.0% | 0 | 0.0% | 25.4 | 27.9% | 25.4 | 27.9% | 0 | 0.0% |
| Triethyl citrate | 0.6 | 0.8% | 0.6 | 0.8% | 2.5 | 2.7% | 2.5 | 2.7% | 0.7 | 0.9% |
| Duocoat inner layer: $KH_2PO_4$ | 0 | 0.0% | 0 | 0.0% | 0 | 0.0% | 0 | 0.0% | 0.9 | 1.1% |
| Duocoat inner layer: HPMC 603 | 0 | 0.0% | 0 | 0.0% | 0 | 0.0% | 0 | 0.0% | 3.2 | 3.9% |
| Subtotal | 13.3 | 17.4% | 13.3 | 17.4% | 27.9 | 30.6% | 27.9 | 30.6% | 18.6 | 22.7% |
| Total Pellets Weight | 76.6 | 100.0% | 76.6 | 100.0% | 91.2 | 100.0% | 91.2 | 100.0% | 81.9 | 100.0% |

In some embodiments, the present formulation is one of those presented in the following Table C and/or as described in the Examples herein (including, without limitation FIG. 31 and TABLE 18):

TABLE C

| Component | F1 | % | F2 | % | F3 | % | F4 | % | F5 | % |
|---|---|---|---|---|---|---|---|---|---|---|
| (all units in mg unless noted) | | | | | | | | | | |
| Layered pellets | | | | | | | | | | |
| Sucrose sphere | 19.50 | | 19.50 | | 19.50 | | 19.50 | | 19.50 | |
| Hydroxypropylcellulose | 29.30 | | 29.30 | | 29.30 | | 29.30 | | 29.30 | |
| P3A | 13.20 | | 13.20 | | 13.20 | | 13.20 | | 13.20 | |
| Buffer Salts | 1.3 | | 1.3 | | 1.3 | | 1.3 | | 1.3 | |
| Subtotal | 63.3 | | 63.3 | | 63.3 | | 63.3 | | 63.3 | |
| Pellets coating | | | | | | | | | | |
| EUDRAGIT FS 30 D (dry polymer) | 12.7 | | 12.7 | | 0 | | 0 | | 13.8 | |
| EUDRAGIT S100 | 0 | | 0 | | 25.4 | | 25.4 | | 0 | |
| Triethyl citrate | 0.6 | | 0.6 | | 2.5 | | 2.5 | | 0.7 | |
| Duocoat inner layer: $KH_2PO_4$ | 0 | | 0 | | 0 | | 0 | | 0.9 | |
| Duocoat inner layer: HPMC 603 | 0 | | 0 | | 0 | | 0 | | 3.2 | |
| Subtotal | 13.3 | | 13.3 | | 27.9 | | 27.9 | | 18.6 | |
| Total Pellets Weight | 76.6 | | 76.6 | | 91.2 | | 91.2 | | 81.9 | |

TABLE C-continued (all units in mg unless noted)

| Component | F1 | % | F2 | % | F3 | % | F4 | % | F5 | % |
|---|---|---|---|---|---|---|---|---|---|---|
| Capsule Shell | | | | | | | | | | |
| Size 4 Gelatin capsule | 0 | | 42.0 | | 0 | | 42.0 | | 0 | |
| Size 4 DRcap | 43.1 | | 0 | | 43.1 | | 0 | | 43.1 | |
| Capsule coating | | | | | | | | | | |
| EUDRAGIT FS 30 D (dry polymer) | 13.0 | | 13.0 | | 13.0 | | 13.0 | | 13.0 | |
| Triethyl citrate | 0.6 | | 0.6 | | 0.6 | | 0.6 | | 0.6 | |
| Subtotal | 13.6 | | 13.6 | | 13.6 | | 13.6 | | 13.6 | |
| Total Capsule Shell Weight | 56.7 | | 55.6 | | 56.7 | | 55.6 | | 56.7 | |
| Total | 133.3 | | 132.2 | | 147.9 | | 146.8 | | 138.6 | |

In various embodiments, the formulations may combine a beta-lactamase with a latex, or other polymer, and a particulate, micro-encapsulated enzyme preparation will be formed. The microspheres then may be covered with a pH-dependent enteric coating. In some embodiments, no sucrose core is required and this allows for higher drug loading per pellet and therefore a smaller capsule size for therapy. There are a variety of approaches for generating particulates (such as microspheres, aggregates, other) that are amenable to the inclusion of proteins. In some embodiments, the approaches involve at least two phases, one containing the protein, and one containing a polymer that forms the backbone of the particulate. For example, one or more of the following may be used: coacervation, where the polymer is made to separate from its solvent phase by addition of a third component, or multiple phase emulsions, such as water in oil in water (w/o/w) emulsion where the inner water phase contains the protein, the intermediate organic phase contains the polymer, and the external water phase stabilizers that support the w/o/w double emulsion until the solvents can be removed to form the microspheres.

In some embodiments, the protein and stabilizing excipients (e.g., trehalose, mannitol, Tween 80, polyvinyl alcohol) are combined and then the mixture is sprayed from aqueous solution and particles that are formed are collected. The particles are then suspended in a dry, water immiscible organic solvent containing polymer and release modifying compounds, and the suspension sonicated to disperse the particles. It is anticipated that the enzyme will retain its activity following this process. Another approach uses aqueous phases but no organic solvent. Here, the enzyme, buffer components, a polymer latex, and stabilizing and release-modifying excipients are dissolved/dispersed in water. The aqueous dispersion is spray-dried, leading to coalescence of the latex, and incorporation of the protein and excipients in particles of the coalesced latex. If the release modifiers are insoluble at acidic conditions but soluble at higher pHs (such as carboxylic acidic) then release from the matrix should be inhibited in the gastric environment.

In various embodiments, the formulations of the present invention take the form of those as described in one or more of U.S. Pat. Nos. 8,535,713 and 8,9117,77 and US Patent Publication Nos. 20120141585, 20120141531, 2006/001896, 2007/0292523, 2008/0020018, 2008/0113031, 2010/0203120, 2010/0255087, 2010/0297221, 2011/0052645, 2013/0243873, 2013/0330411, 2014/0017313, and 2014/0234418, the contents of which are hereby incorporated by reference in their entirety.

In various embodiments, the formulations of the present invention take the form of those as described in International Patent Publication No. WO 2008/135090, the contents of which are hereby incorporated by reference in their entirety.

In various embodiments, the formulations of the present invention take the form of those described in one or more of U.S. Pat. Nos. 4,196,564; 4,196,565; 4,247,006; 4,250,997; 4,268,265; 5,317,849; 6,572,892; 7,712,634; 8,074,835; 8,398,912; 8,440,224; 8,557,294; 8,646,591; 8,739,812; 8,810,259; 8,852,631; and 8,911,788 and US Patent Publication Nos. 2014/0302132; 2014/0227357; 20140088202; 20130287842; 2013/0295188; 2013/0307962; and 20130184290 the contents of which are hereby incorporated by reference in their entirety.

In various embodiments, the beta-lactamase described herein is formulated for microorganism-based release. In some embodiments, the beta-lactamase is formulated for release by a genetically-modified microorganism, optionally selected from fungi, bacteria, and algae. In some embodiments, the genetically-modified microorganism is resistant to one or more oral antibiotic. For example, the invention may pertain to a genetically-modified microorganism comprising one or more beta-lactamases that is formulated for GI tract delivery as described herein and that releases the beta-lactamases, e.g. by secretion. For example, a genetically-modified microorganism comprising one or more beta-lactamases may be formulated for release in the distal small intestine and/or colon and, when released, in turn, secretes or otherwise releases (e.g. via genetically-modified microorganism death or digestion) the beta-lactamase so it may eliminate residual or excess oral antibiotic (e.g. active antibiotic that is not absorbed from the GI tract after an oral dose or is returned in active form to the intestinal tract from the systemic circulation) and prevent GI tract microbiota disruption.

In various embodiments, the genetically-modified microorganism comprising one or more beta-lactamases is formulated so as to deliver viable recombinant yeast cells to the intestines where active beta-lactamases are secreted by the genetically-modified microorganisms. In one embodiment, the genetically-modified microorganism comprising one or more beta-lactamases is formulated as an enteric-coated capsule which directly releases the recombinant genetically-modified microorganism in the intestines. In other embodiments, the genetically-modified microorganism comprising one or more beta-lactamases can be formulated as a gelatin capsule, or the genetically-modified microorganism comprising one or more beta-lactamases can be dissolved in a liquid and ingested. In such embodiments, the genetically-modified microorganism comprising one or more beta-lactamases is delivered anywhere along the GI tract. As described herein, the genetically-modified microorganism comprising one or more beta-lactamases can be released in the distal small intestine and/or the colon; however, delivery anywhere in the GI tract is also imagined, for example, where the genetically-modified microorganism comprising one or more beta-lactamases is able to transit to the area of interest without loss of activity or disruption of the systemic activity of the oral antibiotics. By way of illustration, in some embodiments, a recombinant yeast cell, for example, *Saccharomyces boulardii*, is resistant to stomach acid and remains viable during transit to the intestine, where it secretes active beta-lactamases for neutralizing residual or excess oral antibiotic (e.g. active antibiotic that is not absorbed from the GI tract after an oral dose or is returned in active form to the intestinal tract from the systemic circulation) in the lower GI tract.

In some embodiments, genetically-modified microorganism comprising one or more beta-lactamases quickly transits through the small intestine but transits slowly in the colon and therefore remains in the colon longer and any beta-lactamase it secretes or releases concentrates in the colon.

In some embodiments, the genetically-modified microorganism is a yeast cell. In various embodiments, the yeast cell is selected from *Saccharomyces* spp., *Hansenula* spp., *Kluyveromyces* spp. *Schizzosaccharomyces* spp. *Zygosaccharoinyces* spp., *Pichia* spp., *Monascus* spp., *Geotrichum* spp. and *Yarrowia* spp. In various embodiments, the present invention contemplates expression of a beta-lactamase in a recombinant yeast cell. The recombinant yeast cell may be generated by stable integration into yeast chromosomal DNA of expression cassette(s) that encode and can express the one or more beta-lactamases. Alternatively, recombinant yeast cell may be generated using a process in which the yeast maintains an expression cassette(s) that encode and can express the one or more beta-lactamases on a stable episome. The recombinant yeast cell may be any yeast cell that is capable of surviving in the mammalian intestine. In various embodiments, the yeast cell has a known probiotic capacity, such as yeast strains selected from kefir, kombucha or dairy products. I In one embodiment, the recombinant yeast cell is *Saccharomyces cerevisiae*. In another embodiment, the recombinant yeast cell is the *Saccharomyces cerevisiae* subspecies *Saccharomyces boulardii* (by way of non-limiting example, ATCC 74352 and/or any cells in U.S. Pat. Nos. 6,010,695 and 7,799,328 the contents of which are hereby incorporated by reference in their entirety). *S. cerevasiae* has been marketed for over 40 years as a probiotic. It has been used for the prevention and the treatment of diarrheal diseases, including antibiotic-associated diarrhea and *C. difficile* infection (reviewed by Kelesidis and Pothoulakis, 2012; Hatoum et al., 2012). *S. boulardii* differs from other *S. cerevasiae* strains as the optimal growth temperature of *S. boulardii* is 37° C. while other strains prefer lower temperatures (between 30 and 33° C.), *S. boulardii* is resistant to low pH and is highly tolerant to bile acids (Edwards-Ingram et al., 2007; Graff et al., 2008). *S. boulardii* was demonstrated to survive the intestinal tract in humans (Klein et al., 1993) where 0.1% viable yeast was recovered in feces after a single administration of $10^{10}$ cells. Concurrent antibiotic treatment increased recovery two-fold (Klein et al., 1993).

In some embodiments, the genetically-modified microorganism is a bacterial cell. In some embodiments, the bacterial cell is a *Bacillus* spp. In some embodiments, the genetically-modified microorganism is an algal cell (e.g. *Chlamydomonas* spp., e.g. *Chlamydomonas reinhardtii*) or the chloroplasts thereof.

In some embodiments, the genetically-modified microorganism is one or more of *Saccharomyces boulardii*; *Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei*, *Lactobacillus acidophilus* (Bio-K+CL1285); combination of *Lactobacillus casei*, *Lactobacillus bulgaricus*, *Streptococcus thermophilus* (Actimel); combination of *Lactobacillus acidophilus*, *Bifidobacterium bifidum* (Florajen3); combination of *Lactobacillus acidophilus*, *Lactobacillus bulgaricus delbrueckii* subsp. *bulgaricus*, *Lactobacillus bulgaricus casei*, *Lactobacillus bulgaricus plantarum*, *Bifidobacterium longum*, *Bifidobacterium infantis*, *Bifidobacterium breve*, and *Streptococcus salivarius* subsp. *thermophilus* (VSL #3)).

Such genetically-modified microorganisms may be administered as described herein, including by way of example, enterally, such as orally.

Administration and Dosage

It will be appreciated that the actual dose of the beta-lactamase (and/or additional therapeutic agents) to be administered according to the present invention will vary according to, for example, the particular dosage form and the mode of administration. Many factors that may modify the action of the beta-lactamase (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the beta-lactamase (and/or additional therapeutic agents) can be administered in unit dosage forms (e.g., tablets or capsules) containing, for example, from about 0.01 mg to about 5,000 mg, from about 0.01 mg to about 4,000 mg, from about 0.01 mg to about 3,000 mg, from about 0.01 mg to about 2,000 mg, from about 0.01 mg to about 1,000 mg, from about 0.01 mg to about 950 mg, from about 0.01 mg to about 900 mg, from about 0.01 mg to about 850 mg, from about 0.01 mg to about 800 mg, from about 0.01 mg to about 750 mg, from about 0.01 mg to about 700 mg, from about 0.01 mg to about 650 mg, from about 0.01 mg to about 600 mg, from about 0.01 mg to about 550 mg, from about 0.01 mg to about 500 mg, from about 0.01 mg to about 450 mg, from about 0.01 mg to about 400 mg, from about 0.01 mg to about 350 mg, from about 0.01 mg to about 300 mg, from about 0.01 mg to about 250 mg, from about 0.01 mg to about 200 mg, from about 0.01 mg to about 150 mg, from about 0.01 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg of the active ingredient per unit dosage form, or from about 5 mg to about 80 mg per unit dosage form. For example, a unit dosage form can include about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg of the active ingredient, inclusive of all values and ranges therebetween.

In one embodiment, the beta-lactamase (and/or additional therapeutic agents) is administered at an amount of from about 0.01 mg to about 100 mg daily, an amount of from about 0.01 mg to about 5,000 mg daily, about 0.01 mg to about 4,000 mg daily, about 0.01 mg to about 3,000 mg daily, about 0.01 mg to about 2,000 mg daily, about 0.01 mg to about 1,000 mg daily, from about 0.01 mg to about 950 mg daily, from about 0.01 mg to about 900 mg daily, from about 0.01 mg to about 850 mg daily, from about 0.01 mg to about 800 mg daily, from about 0.01 mg to about 750 mg daily, from about 0.01 mg to about 700 mg daily, from about 0.01 mg to about 650 mg daily, from about 0.01 mg to about 600 mg daily, from about 0.01 mg to about 550 mg daily, from about 0.01 mg to about 500 mg daily, from about 0.01 mg to about 450 mg daily, from about 0.01 mg to about 400 mg daily, from about 0.01 mg to about 350 mg daily, from about 0.01 mg to about 300 mg daily, from about 0.01 mg to about 250 mg daily, from about 0.01 mg to about 200 mg daily, from about 0.01 mg to about 150 mg daily, from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the beta-lactamase (and/or additional therapeutic agents) is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1,000 mg, about 2,000 mg, about 3,000 mg, about 4,000 mg, or about 5,000 mg inclusive of all values and ranges therebetween.

In some embodiments, a suitable dosage of the beta-lactamase (and/or additional therapeutic agents) is in a range of about 0.01 mg/kg to about 100 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, about 20 mg/kg body weight, about 30 mg/kg body weight, about 40 mg/kg body weight, about 50 mg/kg body weight, about 60 mg/kg body weight, about 70 mg/kg body weight, about 80 mg/kg body weight, about 90 mg/kg body weight, or about 100 mg/kg body weight, inclusive of all values and ranges therebetween. In other embodiments, a suitable dosage of the beta-lactamases (and/or additional therapeutic agents) in a range of about 0.01 mg/kg to about 100 mg/kg of body weight, in a range of about 0.01 mg/kg to about 90 mg/kg of body weight, in a range of about 0.01 mg/kg to about 80 mg/kg of body weight, in a range of about 0.01 mg/kg to about 70 mg/kg of body weight, in a range of about 0.01 mg/kg to about 60 mg/kg of body weight, in a range of about 0.01 mg/kg to about 50 mg/kg of body weight, in a range of about 0.01 mg/kg to about 40 mg/kg of body weight, in a range of about 0.01 mg/kg to about 30 mg/kg of body weight, in a range of about 0.01 mg/kg to about 20 mg/kg of body weight, in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of about 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the beta-lactamase may be administered, for example, more than once daily, about once per day, about every other day, about every third day, about once a week, about once every two weeks, about once every month, about once every two months, about once every three months, about once every six months, or about once every year.

Additional Therapeutic Agents and Combination Therapy or Co-Formulation

Administration of the present formulations may be combined with additional therapeutic agents. Co-administration of the additional therapeutic agent and the present formulations may be simultaneous or sequential. Further; the present formulations may comprise an additional therapeutic agent (e.g. via co-formulation). For example, the additional therapeutic agent and the beta-lactamase may be combined into a single formulation.

In one embodiment, the additional therapeutic agent and the beta-lactamase are administered to a subject simultaneously. The term "simultaneously" as used herein, means that the additional therapeutic agent and the beta-lactamase are administered with a time separation of no more than about 60 minutes, such as no more than about 30 minutes, no more than about 20 minutes, no more than about 10 minutes, no more than about 5 minutes, or no more than about 1 minute. Administration of the additional therapeutic agent and the beta-lactamase can be by simultaneous administration of a single formulation (e.g., a formulation comprising the additional therapeutic agent and the beta-lactamase) or of separate formulations (e.g., a first formulation including the additional therapeutic agent and a second formulation including the beta-lactamase).

Co-administration does not require the additional therapeutic agents to be administered simultaneously, if the timing of their administration is such that the pharmacological activities of the additional therapeutic agent and the beta-lactamase overlap in time. For example, the additional therapeutic agent and the beta-lactamase can be administered sequentially. The term "sequentially" as used herein means that the additional therapeutic agent and the beta-lactamase are administered with a time separation of more than about 60 minutes. For example, the time between the sequential administration of the additional therapeutic agent and the beta-lactamase can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional therapeutic agent and the beta-lactamase being administered. Either the additional therapeutic agent or the beta-lactamase may be administered first.

In a further embodiment, the additional therapeutic agent and the beta-lactamase are administered to a subject simultaneously but the release of additional therapeutic agent and the beta-lactamase from their respective dosage forms (or single unit dosage form if co-formulated) in the GI tract occurs sequentially.

Co-administration also does not require the additional therapeutic agents to be administered to the subject by the same route of administration. Rather, each additional therapeutic agent can be administered by any appropriate route, for example, parenterally or non-parenterally.

In some embodiments, the additional therapeutic agent is an anti-bacterial agent, which includes, but is not limited to, cephalosporin antibiotics (cephalexin, cefuroxime, cefadroxil, cefazolin, cephalothin, cefaclor, cefamandole, cefoxitin, cefprozil, and ceftobiprole); fluoroquinolone antibiotics (cipro, Levaquin, floxin, tequin, avelox, and norflox); tetracycline antibiotics (tetracycline, minocycline, oxytetracycline, and doxycycline); penicillin antibiotics (amoxicillin, ampicillin, penicillin V, dicloxacillin, carbenicillin, vancomycin, and methicillin); monobactam antibiotics (aztreonam); and carbapenem antibiotics (ertapenem, doripenem, imipenem/cilastatin, and meropenem). In some embodiments, any of the penicillins and cephalosporins described herein may be the additional therapeutic agent.

In some embodiments, the additional therapeutic agent is a beta-lactamase inhibitor. Exemplary beta-lactamase inhibitors include, for example, tazobactam, sulbactam, clavulanic acid, avibactam, monobactam derivatives, ATMO derivatives, penems (e.g., BRL42715 and derivatives thereof, Syn1012, oxapenems, trinems, 1-s-methylcarbapenems), penicillin and cephalosporin sulfone derivatives (e.g., C-2/C-3-substituted penicillin and cephalosporin sulfones, C-6-substituted penicillin sulfones), non-β-lactam inhibitors (e.g., boronic acid transition state analogs, phophonates, NXL104, hydroxmates) and metallo-R-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. Vancocin), rifaximin, charcoal-based binders/adsorbents (e.g. DAV132), fecal bacteriotherapy, probiotic therapy (see, e.g., *Intnat'l J Inf Dis*, 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+ CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med.* 2010; 362(3):197, the contents of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin.

In some embodiments, the additional therapeutic agent is an antidiarrheal agent. Antidiarrheal agents suitable for use in the present invention include, but are not limited to, DPP-IV inhibitors, natural opioids, such as tincture of opium, paregoric, and codeine, synthetic opioids, such as diphenoxylate, difenoxin and loperamide, bismuth subsalicylate, lanreotide, vapreotide and octreotide, motiln antagonists, COX2 inhibitors like celecoxib, glutamine, thalidomide and traditional antidiarrheal remedies, such as kaolin, pectin, berberine and muscarinic agents.

In some embodiments, the additional therapeutic agent is an anti-inflammatory agent such as steroidal anti-inflammatory agents or non-steroidal anti-inflammatory agents (NSAIDS). Steroids, particularly the adrenal corticosteroids and their synthetic analogues, are well known in the art. Examples of corticosteroids useful in the present invention include, without limitation, hydroxyltriamcinolone, alpha-methyl dexamethasone, beta-methyl betamethasone, beclomethasone dipropionate, betamethasone benzoate, betamethasone dipropionate, betamethasone valerate, clobetasol valerate, desonide, desoxymethasone, dexamethasone, diflorasone diacetate, diflucortolone valerate, fluadrenolone, fluclorolone acetonide, flumethasone pivalate, fluosinolone acetonide, fluocinonide, flucortine butylester, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone acetonide, medrysone, amcinafel, amcinafide, betamethasone and the balance of its esters, chloroprednisone, clocortelone, clescinolone, dichlorisone, difluprednate, flucloronide, flunisolide, fluorometha-lone, fluperolone, fluprednisolone, hydrocortisone, meprednisone, paramethasone, prednisolone, prednisone, beclomethasone dipropionate. (NSAIDS) that may be used in the present invention, include but are not limited to, salicylic acid, acetyl salicylic acid, methyl salicylate, glycol salicylate, salicylmides, benzyl-2,5-diacetoxybenzoic acid, ibuprofen, fulindac, naproxen, ketoprofen, etofenamate, phenylbutazone, and indomethacin. Additional anti-inflammatory agents are described, for example, in U.S. Pat. No. 4,537,776, the entire contents of which is incorporated by reference herein.

In some embodiments, the additional therapeutic agent may be an analgesic. Analgesics useful in the compositions and methods of the present invention include, without limitation, morphine, codeine, heroine, methadone and related compounds, thebaine, orpiavine, and their derivatives, buprenorphine, the piperidines, morphinans, benzomorphans, tetrahydroisoquinolines, thiambutanes, benzylamines, tilidine, viminol, nefopam, capsaicin (8-methyl-N-vanillyl-6E-nonenamide), "synthetic" capsaicin (N-vanillylnonamide), and related compounds.

In some embodiments, the additional therapeutic agent may be an anti-viral agent that includes, but is not limited to, Abacavir, Acyclovir, Adefovir, Amprenavir, Atazanavir, Cidofovir, Darunavir, Delavirdine, Didanosine, Docosanol, Efavirenz, Elvitegravir, Emtricitabine, Enfuvirtide, Etravirine, Famciclovir, and Foscarnet. For all additional therapeutic agent compositions and methods, targeting to various parts of the GI tract may be employed as described herein.

In some embodiments, the present formulations are administered to a subject to avoid treatment with an additional therapeutic agent. For example, in the context of preventing *C. difficile* infection (CDI) and/or a *C. difficile*-associated disease, the present formulations may be provided to a subject to avoid the necessity of receiving, for example, vancomycin.

Methods of Treatment

In various aspects, the present invention provides methods for protecting a subject's gastrointestinal microbiome, comprising administering an effective amount of a pharmaceutical composition comprising a beta-lactamase, for example, any of the formulations described herein, to a subject who is undergoing treatment or has recently undergone treatment with an oral antibiotic. The beta-lactamase is capable of deactivating (by way of non-limitation, hydrolyzing) the oral antibiotic. In various embodiments, the oral antibiotic is one or more of a ceftriaxone, cefotaxime, cefazolin, cefoperazone, cefuroxime, and piperacillin.

In various embodiments, the subjects include, but are not limited to, subjects that are at a particular risk for a microbiome-mediated disorder, such as those undergoing treatment or has recently undergone treatment with an oral antibiotic. For example, the subject may be taking an oral antibiotic during the past 30 or so days and/or have an immune system that is weak (e.g. from a chronic illness) and/or are women and/or are elderly (e.g. over about 65 years old) and/or are elderly woman and/or undergo treatment with for heartburn or stomach acid disorders (e.g. with agents such as PREVACID, TAGAMET, PRILOSEC, or NEXIUM and related drugs) and/or have recently been in the hospital, including in an intensive care unit, or live in a nursing home. Accordingly, in some embodiments, the methods and uses of the present invention treat or prevent a nosocomial infection and/or a secondary emergent infection and/or a hospital acquired infection (HAI).

In some embodiments, the methods and uses of the present invention include those in which an initial and/or adjunctive therapy is administered to a subject. Initial and/or adjunctive therapy indicates therapy that is used to treat for example, a microbiome-mediated disorder or disease upon detection of such disorder or disease. In some embodiments, the initial and/or adjunctive therapy is one or more of metronidazole, vancomycin, fidaxomicin, rifaximin, charcoal-based binder/adsorbent, fecal bacteriotherapy, probiotic therapy, and antibody therapy, as described herein. In various embodiments, the methods and uses of the present invention include use of the pharmaceutical compositions and formulations including beta-lactamase (and/or additional therapeutic agent) as an adjuvant to any of these initial and/or adjunctive therapies (including co-administration or sequential administration). In various embodiments, the methods and uses of the present invention include use of the pharmaceutical compositions and formulations including beta-lactamase (and/or additional therapeutic agent) in a subject undergoing initial and/or adjunctive therapies.

In some embodiments, the methods and uses of the present invention include those in which an oral antibiotic and a beta-lactamase inhibitor are administered to a subject. In various embodiments, the subject may be receiving a co-formulation of an oral antibiotic with one or more beta-lactamase inhibitors (e.g. Augmentin is a mixture of amoxicillin and clavulanic acid). Such co-formulations include, but are not limited to, amoxicillin-clavulanic acid (Augmentin, ticarcillin-clavulanic acid (Timentin), ampicillin-sulbactam (Sultamicillin, e.g. Unasyn), piperacillin-tazobactam (Zosyn), and cefoperazone-sulbactam. In various embodiments, methods of the present invention comprise further administering a beta-lactamase inhibitor that releases in the GI tract proximal to the beta-lactamase. In an embodiment, the beta-lactamase inhibitor may be released at various parts of the GI tract where the oral antibiotic may be active. For example, the beta-lactamase inhibitor may be released at the stomach, duodenum, jejunum and ileum. Exemplary beta-lactamase inhibitors include, for example, tazobactam, sulbactam, clavulanic acid, avibactam, monobactam derivatives, ATMO derivatives, penems (e.g., BRL42715 and derivatives thereof, Syn1012, oxapenems, trinems, 1-β-methylcarbapenems), penicillin and cephalosporin sulfone derivatives (e.g., C-2/C-3-substituted penicillin and cephalosporin sulfones, C-6-substituted penicillin sulfones), non-3-lactam inhibitors (e.g., boronic acid transition state analogs, phophonates, NXL104, hydroxmates) and metallo-R-lactamase inhibitors such as thiol derivatives, pyridine dicarboxylates, trifluoromethyl ketones and alcohols, carbapenem analogs, tricyclic natural products, succinate derivatives, and C-6-mercaptomethyl penicillinates.

In various embodiments, the methods of the invention comprise treating or preventing a microbiome-mediated disorder. Illustrative microbiome-mediated disorder includes, but is not limited to, for example, those found in Table 3 of WO2014/121298, the entire contents of which are incorporated herein by reference. For example, the microbiome-mediated disorder may be selected from an antibiotic-induced adverse effect, a *C. difficile* infection (CDI), a *C. difficile*-associated disease, ulcerative colitis, Crohn's disease, and irritable bowel syndrome. In various embodiments, the microbiome-mediated disorder is an antibiotic-induced adverse effect, a *C. difficile* infection (CDI), or a *C. difficile*-associated disease. In an embodiment, the present invention provides methods for treating an antibiotic-induced adverse effect in the GI tract, comprising administering an effective amount of a pharmaceutical composition or formulation including beta-lactamase (and/or additional therapeutic agent) described herein to a subject who is undergoing treatment or has recently undergone treatment with an oral antibiotic. In another embodiment, the present invention provides methods for preventing an antibiotic-induced adverse effect in the GI tract, comprising administering an effective amount of a pharmaceutical composition or formulation including beta-lactamase (and/or additional therapeutic agent) described herein to a subject who is undergoing treatment or has recently undergone treatment with an oral antibiotic.

In an embodiment, the present invention provides methods for treating *C. difficile* infection (CDI) and/or a *C. difficile*-associated disease, comprising administering an effective amount of a pharmaceutical composition or formulation including beta-lactamase (and/or additional therapeutic agent) described herein to a subject who is undergoing treatment or has recently undergone treatment with an oral antibiotic. In another embodiment, the present invention provides methods for preventing *C. difficile* infection (CDI) and/or a *C. difficile*-associated disease, comprising administering an effective amount of a pharmaceutical composition or formulation including beta-lactamase (and/or additional therapeutic agent) described herein to a subject who is undergoing treatment or has recently undergone treatment with an oral antibiotic.

In various embodiments, the present invention relates to methods of preventing and/or reducing the likelihood that a subject becomes afflicted with an antibiotic-associated adverse effect (e.g. *Clostridium* difficie infection, antibiotic associated diarrhea) by administering an effective amount of a beta-lactamase formulation as described herein, such as, without limitation, those described elsewhere herein and presented in TABLEs A, B, or C and the Examples. In some embodiments, the formulation, optionally, in the form of a capsule (e.g., a hard gelatin or HPMC capsule) comprises a plurality of enteric-coated beta-lactamase-containing pellets. In some embodiments, the formulation, optionally, in the form of a capsule (e.g., a hard gelatin or HPMC capsule) comprises a plurality of beta-lactamase-containing pellets coated with an osmotic rupture coating.

In various embodiments, the antibiotic-induced adverse effect and/or CDI or *C. difficile*-associated disease is one or more of: antibiotic-associated diarrhea, *C. difficile* diarrhea (CDD), *C. difficile* intestinal inflammatory disease, colitis, pseudomembranous colitis, fever, abdominal pain, dehydration and disturbances in electrolytes, megacolon, peritonitis, and perforation and/or rupture of the colon. Additional diseases, disorders and conditions which are suitable for treatment with the compositions and methods of the invention include those listed in Table 3 of WO2014/121298, the entire contents of which are incorporated herein by reference.

In various embodiments, the present uses and methods pertain to co-treatment (simultaneously or sequentially) with the pharmaceutical composition or formulation including beta-lactamase (and/or additional therapeutic agent) described herein and/or any initial and/or adjunctive therapy, or treatment with a co-formulation of the pharmaceutical composition or formulation including beta-lactamase (and/ or any additional therapeutic agent) described herein and/or any initial and/or adjunctive therapy for treatment of the various diseases described herein.

In various embodiments, the microbiome-mediated disorder is treated or prevented in the context of initial onset or relapse/recurrence (e.g. due to continued or restarted antibiotic therapy). For example, in a subject that has previously suffered from a microbiome-mediated disorder (e.g., CDI), the present pharmaceutical composition or formulation including beta-lactamase (and/or additional therapeutic agent) may be administered upon the first symptoms of recurrence in the subject. By way of non-limiting example, symptoms of recurrence include, in a mild case, about 5 to about 10 watery bowel movements per day, no significant fever, and only mild abdominal cramps while blood tests may show a mild rise in the white blood cell count up to about 15,000 (normal levels are up to about 10,000), and, in a severe case, more than about 10 watery stools per day, nausea, vomiting, high fever (e.g. about 102-104° F.), rectal bleeding, severe abdominal pain (e.g. with tenderness), abdominal distention, and a high white blood count (e.g. of about 15,000 to about 40,000).

Regardless of initial onset or relapse/recurrence, the microbiome-mediated disorder may be diagnosed via any of the symptoms described herein (e.g. watery diarrhea about 3 or more times a day for about 2 days or more, mild to bad cramping and pain in the belly, fever, blood or pus in the stool, nausea, dehydration, loss of appetite, loss of weight, etc.). Regardless of initial onset or relapse/recurrence, the microbiome-mediated disorder may also be diagnosed via enzyme immunoassays (e.g. to detect the *C. difficile* toxin A or B antigen and/or glutamine dehydrogenase (GDH), which is produced by *C. difficile* organisms), polymerase chain reactions (e.g., to detect the *C. difficile* toxin A or B gene or a portion thereof (e.g. tcdA or tcdB), including the ILLU-MIGENE LAMP assay), a cell cytotoxicity assay. For example, any of the following tests may be used: Meridian ImmunoCard Toxins A/B; Wampole Toxin A/B Quik Chek; Wampole C. diff Quik Chek Complete; Remel Xpect *Clostridium difficile* Toxin A/B; Meridian Premier Toxins A/B; Wampole *C. difficile* Tox A/B II; Remel Prospect Toxin A/B EIA; Biomerieux Vidas *C. difficile* Toxin A&B; BD Geneohm C. diff; Prodesse Progastro CD; and Cepheld Xpert C. diff. In various embodiments, the clinical sample is a subject's stool sample.

Also a flexible sigmoidoscopy "scope" test and/or an abdominal X-ray and/or a computerized tomography (CT) scan, which provides images of your colon, may be used in assessing a subject (e.g. looking for characteristic creamy white or yellow plaques adherent to the wall of the colon). Further, biopsies (e.g. of any region of the GI tract) may be used to assess a potential microbiome-mediated disorder (e.g., CDI and/or *C. difficile* associated disease) in subject.

In various embodiments, the methods and uses of the present invention relate to pharmaceutical compositions and formulations including beta-lactamase (and/or additional therapeutic agent) which release the beta-lactamase (and/or additional therapeutic agent) in a location in the GI tract in which it deactivates excess oral antibiotic residue. In an embodiment, the methods and uses of the present invention relate to pharmaceutical compositions and formulations including beta-lactamase (and/or additional therapeutic agent) which deactivate excess oral antibiotic residue before it enters the GI tract, including the small and/or large intestine. In an embodiment, the methods and uses of the present invention relate to pharmaceutical compositions and formulations including beta-lactamase (and/or additional therapeutic agent) which deactivate excess oral antibiotic residue before it enters the large intestine. In an embodiment, the methods and uses of the present invention relate to pharmaceutical compositions and formulations including beta-lactamase (and/or additional therapeutic agent) which deactivate excess oral antibiotic residue in the GI tract. In various embodiments, the pharmaceutical compositions and formulations including beta-lactamase (and/or additional therapeutic agent) as described herein releases the beta-lactamase (and/or additional therapeutic agent) in a location in the GI tract that is distal to the release of the oral antibiotic. In various embodiments, the beta-lactamase (and/or additional therapeutic agent) is released in a location in the GI tract where it prevents a microbicidal activity of the residual or excess oral antibiotic (e.g. active antibiotic that is not absorbed from the GI tract after an oral dose or is returned in active form to the intestinal tract from the systemic circulation) on GI tract microbiota.

In some embodiments, methods and uses of the present invention relate to pharmaceutical compositions and formulation including beta-lactamase (and/or additional therapeutic agent) which maintain a normal intestinal microbiota and/or prevent the overgrowth of one or more pathogenic microorganisms in the GI tract of a subject. In various embodiments, the present invention provides for pharmaceutical compositions and methods that mitigate or prevent the overgrowth of various coliforms in a subject's gut (including coliforms that are virulent and/or antibiotic resistant). In various aspects, the methods, pharmaceutical compositions and formulations described herein prevent or diminish secondary infections with resistant organisms and may, in some embodiments, diminish beta-lactam resistance development. Further, the methods, pharmaceutical compositions and formulations described herein may allow for use of beta-lactam antibiotics which are currently avoided due to resistance concerns and/or reduce the need for co-administration or co-formulation with one or more beta-lactamase inhibitors (e.g. Augmentin, Sultamicillin).

In various embodiments, the beta-lactamases and/or pharmaceutical compositions (and/or additional therapeutic agents) do not substantially interfere with blood or plasma levels of an oral antibiotic. For example, the beta-lactamases and/or pharmaceutical compositions (and/or additional therapeutic agents) of the present invention allow for a subject to receive an oral antibiotic that might be required for an infection and do not interfere with the systemic activity of the oral antibiotic or the time above minimum inhibitory concentrations of the antibiotic in the plasma. In an embodiment, the beta-lactamases and/or pharmaceutical compositions (and/or additional therapeutic agents) does not substantially interfere with blood or plasma levels of the oral antibiotic. Rather, the beta-lactamases and/or pharmaceutical compositions (and/or additional therapeutic agents) inactivate residual or excess oral antibiotic (e.g. active antibiotic that is not absorbed from the GI tract after an oral dose or is returned in active form to the intestinal tract from the systemic circulation) that may populate parts of the GI tract and in doing so, prevent the disruption of the microbiota that is linked to the various disease states described herein.

In various embodiments, the pharmaceutical compositions and formulations including beta-lactamase and/or additional therapeutic agent are not systemically absorbed. In some embodiments, the compositions and formulations including beta-lactamase (and/or additional therapeutic agent) do not interfere with the antibiotic absorption from the gut and/or or antibiotic enterohepatic recirculation enough to be clinically important.

In various embodiments, the pharmaceutical compositions and formulations including beta-lactamase and/or additional therapeutic agent are used as an adjuvant for the treatment of *H. pylori* infection, e.g. in the gastric mucosa. For instance, the present pharmaceutical compositions and formulations may be used as adjuvant to amoxicillin treatments (e.g. as an adjuvant to "triple therapy" (e.g. proton pump inhibitors such as omeprazole, pantoprazole, or rabeprazole and the antibiotics clarithromycin and amoxicillin, or metronidazole)). By way of example, the amoxicillin would be administered such that it is delivered to the stomach where it has a therapeutic effect and then it is deactivated upon exiting the stomach by the pharmaceutical compositions and formulations (e.g. duodenally-released). Accordingly, provided herein are methods of treating or preventing *H. pylori* infection in a subject's stomach by administering a pharmaceutical compositions and formulations including beta-lactamase and/or additional therapeutic agent described herein. Further, the present methods are useful in treating or preventing an *H. pylori* infection-related disease (by way of non-limiting example: ulcers (e.g. duodenal ulcers, peptic ulcer disease), cancers (e.g. stomach cancer, gastric MALT lymphoma), and dyspepsia). In some of these embodiments, there is no requirement to preserve a systemic level of oral antibiotic.

In some embodiments, the terms "patient" and "subject" are used interchangeably. In some embodiments, the subject and/or animal is a mammal, e.g., a human, mouse, rat, guinea pig, dog, cat, horse, cow, pig, rabbit, sheep, or non-human primate, such as a monkey, chimpanzee, or baboon. In other embodiments, the subject and/or animal is a non-mammal, such, for example, a zebrafish. In some embodiments, the subject and/or animal may comprise fluorescently-tagged cells (with e.g. GFP). In some embodiments, the subject and/or animal is a transgenic animal comprising a fluorescent cell.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a subject. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In one embodiment, the human is a child. In one embodiment, the human is a female.

In other embodiments, the subject is a non-human animal, and therefore the invention pertains to veterinary use. In a specific embodiment, the non-human animal is a household pet. In another specific embodiment, the non-human animal is a livestock animal.

Kits

The invention provides kits that can simplify the administration of any agent described herein. An exemplary kit of the invention comprises any composition described herein in unit dosage form. In one embodiment, the unit dosage form is a container, such as a pre-filled syringe, which can be sterile, containing any agent described herein and a pharmaceutically acceptable carrier, diluent, excipient, or vehicle. The kit can further comprise a label or printed instructions instructing the use of any agent described herein. The kit may also include a lid speculum, topical anesthetic, and a cleaning agent for the administration location. The kit can also further comprise one or more additional therapeutic agents described herein. In one embodiment, the kit comprises a container containing an effective amount of a composition of the invention and an effective amount of another composition, such those described herein.

In some embodiments, the additional therapeutic agent is an adjunctive therapy that is used in, for example, the treatment of CDI as described herein. In some embodiments, the additional therapeutic agent is metronidazole (e.g. FLAGYL), fidaxomicin (e.g. DIFICID), or vancomycin (e.g. Vancocin), rifaximin, fecal bacteriotherapy, charcoal-based binders/adsorbents (e.g. DAV132), probiotic therapy (see, e.g., *Intnat'l J Inf Dis,* 16 (11): e786, the contents of which are hereby incorporated by reference, illustrative probiotics include *Saccharomyces boulardii; Lactobacillus rhamnosus* GG; *Lactobacillus plantarum* 299v; *Clostridium butyricum* M588; *Clostridium difficile* VP20621 (non-toxigenic *C. difficile* strain); combination of *Lactobacillus casei, Lactobacillus acidophilus* (Bio-K+CL1285); combination of *Lactobacillus casei, Lactobacillus bulgaricus, Streptococcus thermophilus* (Actimel); combination of *Lactobacillus acidophilus, Bifidobacterium bifidum* (Florajen3); combination of *Lactobacillus acidophilus, Lactobacillus bulgaricus delbrueckii* subsp. *bulgaricus, Lactobacillus bulgaricus casei, Lactobacillus bulgaricus plantarum, Bifidobacterium longum, Bifidobacterium infantis, Bifidobacterium breve, Streptococcus salivarius* subsp. *thermophilus* (VSL #3)) and antibody or other biologic therapy (e.g. monoclonal antibodies against *C. difficile* toxins A and B as described in *N Engl J Med.* 2010; 362(3):197, the content of which are hereby incorporated by reference in their entirety; neutralizing binding proteins, for example, arranged as multimers, which are directed to one or more of SEQ ID NOs. recited in United States Patent Publication No. 2013/0058962 (e.g. one or more of SEQ ID Nos.: 59, 60, 95, 67, 68, and 87), the contents of which are hereby incorporated by reference); or any neutralizing binding protein directed against *C. difficile* binary toxin. In some embodiments, any of the penicillins and cephalosporins described herein may be the additional therapeutic agent.

EXAMPLES

Example 1. SYN-004 Microbiome Protection from Oral Amoxicillin Microbiome Damage SYN-004 was formulated as an enteric-coated pellet that releases at pHs of 5.5 and higher. Therefore, SYN-004 is protected from low pH, similar to what is found in the stomach, and released at pHs greater than 5.5, similar to the pH in the duodenum (pH 5.9-6.6). Release of SYN-004 is expected to continue throughout the small intestine, i.e., the jejunum (pH 6.6-7.4), the ileum (pH 7.3-7.8), and/or cecum (pH 5.6-5.9).

The formulation used for this study is as follows:

TABLE 1

Composition of P3A Delayed-Release Capsules, 75 mg and 25 mg, and Placebo Capsule

| | 75 mg Capsule | | 25 mg Capsule | | Placebo Capsule | |
|---|---|---|---|---|---|---|
| Component | mg | % Total | mg | % Total | mg | % Total |
| Sucrose sphere | 110.8 | 23.3 | 36.9 | 23.3 | 139.8 | 29.5 |
| Hydroxypropylcellulose | 166.3 | 35.0 | 55.4 | 35.0 | 209.6 | 44.2 |
| EUDRAGIT L 30 D-55 | 98.9 | 20.8 | 33.0 | 20.8 | 98.7 | 20.8 |
| P3A | 75.0 | 15.8 | 25.0 | 15.8 | — | — |
| Buffer salts | 7.5 | 1.6 | 2.5 | 1.6 | 9.4 | 2.0 |
| Glyceryl monostearate | 4.9 | 1.0 | 1.6 | 1.0 | 4.9 | 1.0 |
| Polysorbate-80 | 2.0 | 0.4 | 0.7 | 0.4 | 2.0 | 0.4 |
| Triethyl citrate | 9.9 | 2.1 | 3.3 | 2.1 | 9.9 | 2.1 |
| Subtotal | 475.3 | 100.0 | 158.4 | 100.0 | 474.3 | 100.0 |
| Hard gelatin capsule #0 or Hydroxypropyl methylcellulose (HPMC) capsule | 96.0 | | 96.0 | | 96.0 | |
| Total | 571.3 | | 254.4 | | 570.3 | | and as described in PCT/US15/54606, the entire contents of which are incorporated by reference.

In vitro dissolution studies revealed that the current formulation of SYN-004 is released in a pH-dependent manner and requires 1-3 hours for complete release, while transit time through the small intestine is approximately 3 hrs+1 hr SEM after entering the duodenum. See, e.g. US Patent Publication No. 2016/0101058, the entire contents of which are hereby incorporated by reference. These data suggest that SYN-004 will be released in a sustained manner throughout the proximal and distal small intestine. Orally-delivered antibiotics such as amoxicillin are absorbed in the proximal small intestine such as the duodenum and the jejunum, but not in the ileum (Barr, et al., 1994).

A study was performed using normal piglets to determine if SYN-004, when delivered orally with oral amoxicillin, interfered with amoxicillin absorption into the blood. If SYN-004 did not interfere with amoxicillin absorption, then fecal DNA collected at various time points throughout the study will be sequenced and analyzed to determine if SYN-004 functioned to protect the microbiome (TABLE 2).

TABLE 2

Piglet study design

| Group (N = 5) | Antibiotic | Antibiotic Delivery | SYN-004 |
|---|---|---|---|
| 1<br>Pig 1, 2, 3, 4, 5 | Amoxicillin suspension (40 mg/kg/day) | Oral, BID, each dose 20 mg/kg 7 am, 5 pm | None |
| 2<br>Pig 6, 7, 8, 9, 10 | Amoxicillin suspension (40 mg/kg/day) | Oral, BID, each dose 20 mg/kg 7 am, 5 pm | 1 size 0 capsule (75 mg), QID 7am, 12 pm, 5 pm, 10 pm |

A total of ten, two-month old Yorkshire piglets, approximately 20 kg each, were used for this study. All 10 animals were treated with oral amoxicillin twice a day for a total of 7 days, and one cohort of 5 animals was also treated with oral SYN-004 four times a day for a total of 9 days. The SYN-004 treatment was started the day before amoxicillin treatment and continued for a day after amoxicillin was stopped (FIG. 1).

Two pre-treatment fecal samples were obtained, the first 4 days after the animals arrived at the animal treatment facility (Day −7), and the second 7 days after arrival (Day −4). An additional 3 fecal samples were collected at Day 4, Day 8, and Day 9. The fecal samples were collected using the OMNlgene GUT sample collection kits (OMR-200, DNA Genotek, Ontario, Canada) and stored at room temperature away from light until all samples were collected.

On Study Day 0, Group 2 (Pigs 6-10) received one size 0 capsule of SYN-004, containing 75 mg of SYN-004, orally, four times a day at 7 am, 12 pm, 5 pm, and 10 pm for a total of 9 days. Pigs were fed 3 times a day, after SYN-004 dosing at 7 am, after SYN-004 dosing at 12 pm, and after SYN-004 dosing at 5 pm. Beginning on Study Day 1, Groups 1 and 2 (Pigs 1-10) received oral amoxicillin (fruit flavored oral suspension, Sandoz, NDC: 0781-6157-46, Lot #EY9130; 20 mg/kg) twice a day at 7 am and at 5 pm, for a total of 7 days. Animals received the amoxicillin first, followed by the SYN-004, then feeding.

On Day 2, after 4 amoxicillin doses, animals were bled and serum collected. Blood was collected aseptically from the vena cava from anesthetized animals. Three blood draws were performed, at 1 hr, 3 hrs, and 8 hrs after amoxicillin administration. A Telazol cocktail was administered intramuscularly at a minimal dose (1 mL or less per 50 lbs) to achieve light anesthesia/sedations. At each timepoint, approximately 9 mL of blood was collected into a serum separator vacutainer tube. After coagulation, samples were centrifuged and the serum was transferred to a cryovial and stored at −80° C. until shipment to the evaluation laboratory (Sannova Analytical, Inc., Somerset, N.J.).

Amoxicillin levels in the pig serum were quantified using a validated liquid chromatography method with MS/MS detection. A standard curve was prepared in negative control pig serum and had 8 points ranging from 100.724 ng/mL to 10072.381 ng/mL of amoxicillin. The limit of detection of the assay was 100 ng/mL. The amoxicillin levels in the animals that received amoxicillin alone (Pigs 1-5) showed peak levels at 3 hours ranging from 1032 to 1687 ng/mL that decreased to 191 to 353 ng/mL by 8 hrs (TABLE 3). Amoxicillin was not detected in the serum of any animal at any time point when the animals received SYN-004+amoxicillin (Pigs 6-10; TABLE 3). These data demonstrate that the SYN-004 interfered with amoxicillin absorption suggesting that the SYN-004 was released prior to amoxicillin absorption and degraded the amoxicillin in the GI tract. Therefore, fecal DNA was not analyzed. Additional modified-release formulations of SYN-004 were generated and evaluated.

TABLE 3

Amoxicillin levels in pig serum

| | Amoxicillin (ng/mL) | | |
|---|---|---|---|
| Pig | 1 hour | 3 hours | 8 hours |
| 1 | 512.4 | 1032.2 | 225.6 |
| 2 | 661.2 | 1105.0 | 296.4 |
| 3 | 591.8 | 1022.1 | 190.7 |
| 4 | 998.0 | 1687.2 | 239.2 |
| 5 | 658.3 | 1137.7 | 252.5 |
| 6 | BLQ | BLQ | BLQ |
| 7 | BLQ | BLQ | BLQ |
| 8 | BLQ | BLQ | BLQ |
| 9 | BLQ | BLQ | BLQ |
| 10 | BLQ | BLQ | BLQ |

BLQ: Below the limit of quantification, 100 ng/mL

Example 2. SYN-004 Multi-Particulates, Additional SYN-004 Formulations and Their In Vitro Characterization Three additional modified-release formulations of SYN-004 were generated and tested. The starting material for the formulations was SYN-004-coated sucrose pellets that lacked the outer, enteric-coating. P3A (SYN-004) layered pellets were produced by spray application of P3A drug substance using hydroxypropylcellulose (HPC) or hydroxypropylmethyl cellulose (HPMC) as a binder excipient, water as a solvent, and sucrose spheres as starting material. The spray application was performed using a fluid bed system over six work shifts, in order to achieve a final active pharmaceutical agent (API) percentage of at least 15%. After the sixth work shift of spray application of the P3A/HPC mixture, the P3A layered pellets were dried overnight at room temperature on trays, then sifted through a 1.4 mm sieve prior to bulk packaging in polyethylene (PE) bags and PE containers. The drug-layered pellets were stored at 5±3° C. for further processing. For example, in some embodiments, the P3A layered pellets were coated with different coatings to achieve specific enzyme release profiles.

Figure 2:
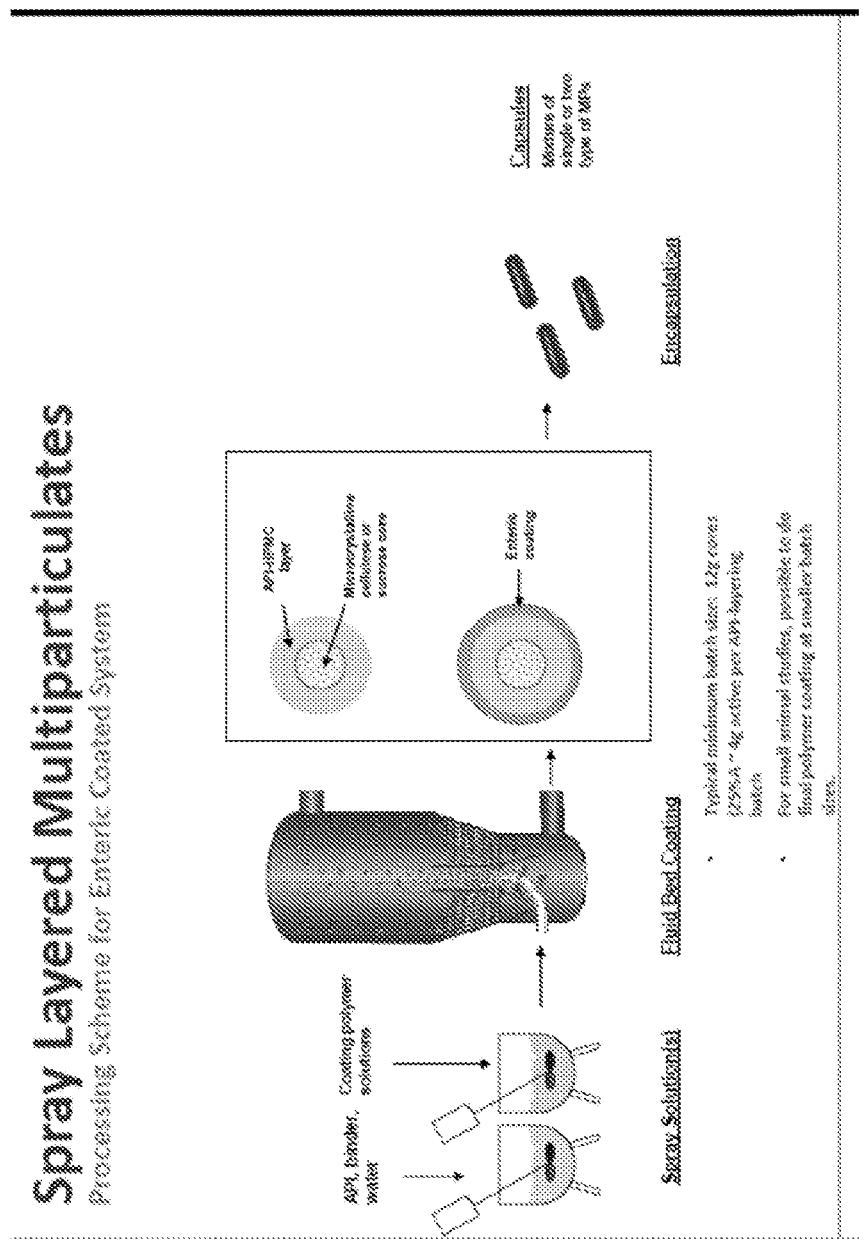
FIG. 2 shows the processing scheme for spray layered multiparticulates as described in Example 2.

The three new formulations utilized different coatings to obtain modified enzyme release profiles (FIG. 2). The different coatings included an enteric coating that released at pHs of >6.2 or an enteric coating that released at pHs of >6.7. The third type of coating was an osmotic-rupture coating that released the enzyme within a specified timeframe, between 2-4 hours after ingestion. The three formulations were characterized in vitro for physical appearance, composition, and enzyme dissolution profiles. The three formulations with the most promising profiles were selected for evaluation with oral amoxicillin in a pig model.

Enteric-Coating SYN-004 Formulation with Release at pHs >6.2

The SYN-004-coated sucrose pellet starting material was coated with a mixture of EUDRAGIT® L100, EUDRAGIT® S100, and triethyl citrate at a ratio of 72.7/18.2/9.1. The parameters of the spray coating (FIG. 2) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The EUDRAGIT® L100, EUDRAGIT® S100, and triethyl citrate at a ratio of 72.7/18.2/9.1 was dissolved in isopropanol and water at a 95/5 ratio. First the isopropanol and water were mixed and then the EUDRAGITs® were added, after which the triethyl citrate was added. The mixture was stirred until dissolved for at least 30 minutes following the addition of the triethyl citrate. The operating parameters of the fluid bed dryer were a gas flow rate of 35 CFM, inlet temperature of 28° C., inlet dew point of 8.6° C., atomizer pressure of 2.7 bar, a spray rate of 2.3 g/min, and a bed temperature of 25° C. The fluid bed process performance was a total solution sprayed of 612 g, a run time of 4 hrs and 25 minutes, a bed dump of 105.1 g, a final coat weight estimate of 35% and a coating efficiency of 97.2%. Samples were dried at 40° C. for 2 hours. Samples were collected at intermediate coating weights of 25% and 30% for characterization along with the coat weight of 35%.

Figure 3:
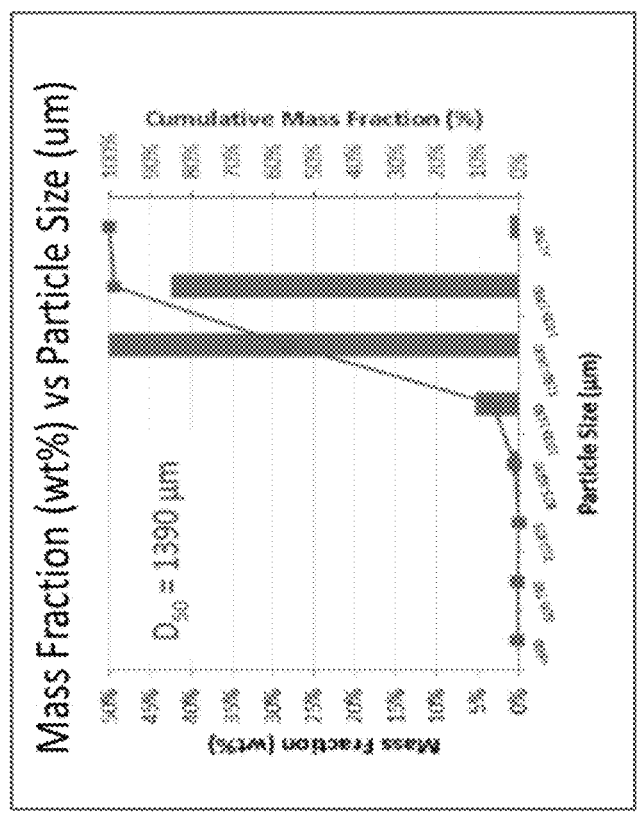
FIG. 3 depicts characterization of the enteric-coated SYN-004 particles that release at pH 6.2. Particles coated with EUDRAGIT® L100, EUDRAGIT® S100, and triethyl citrate at a ratio of 72.7/18.2/9.1 were characterized based on the average coat thickness versus estimated coat weights (panel A) and the mass fraction versus the particle size (panel B).
Figure 3:
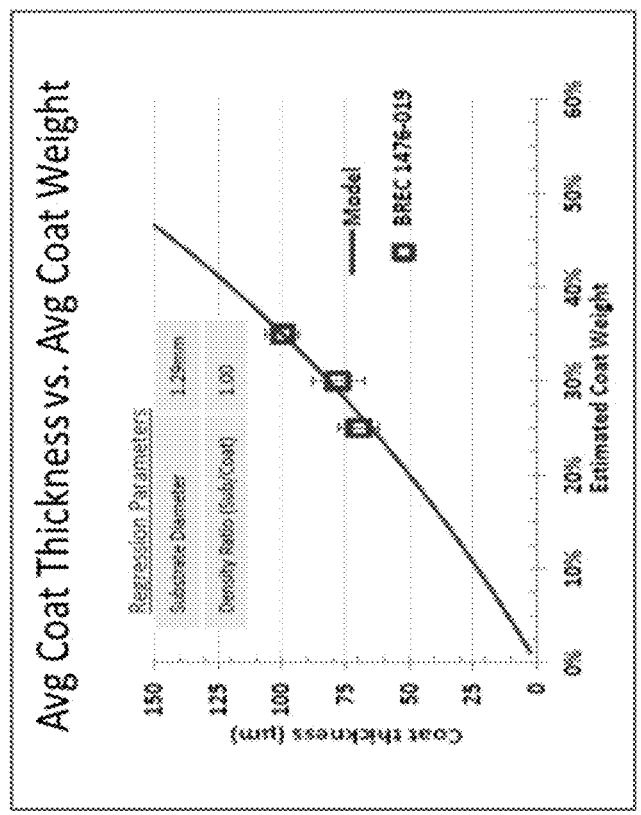
Figure 4:
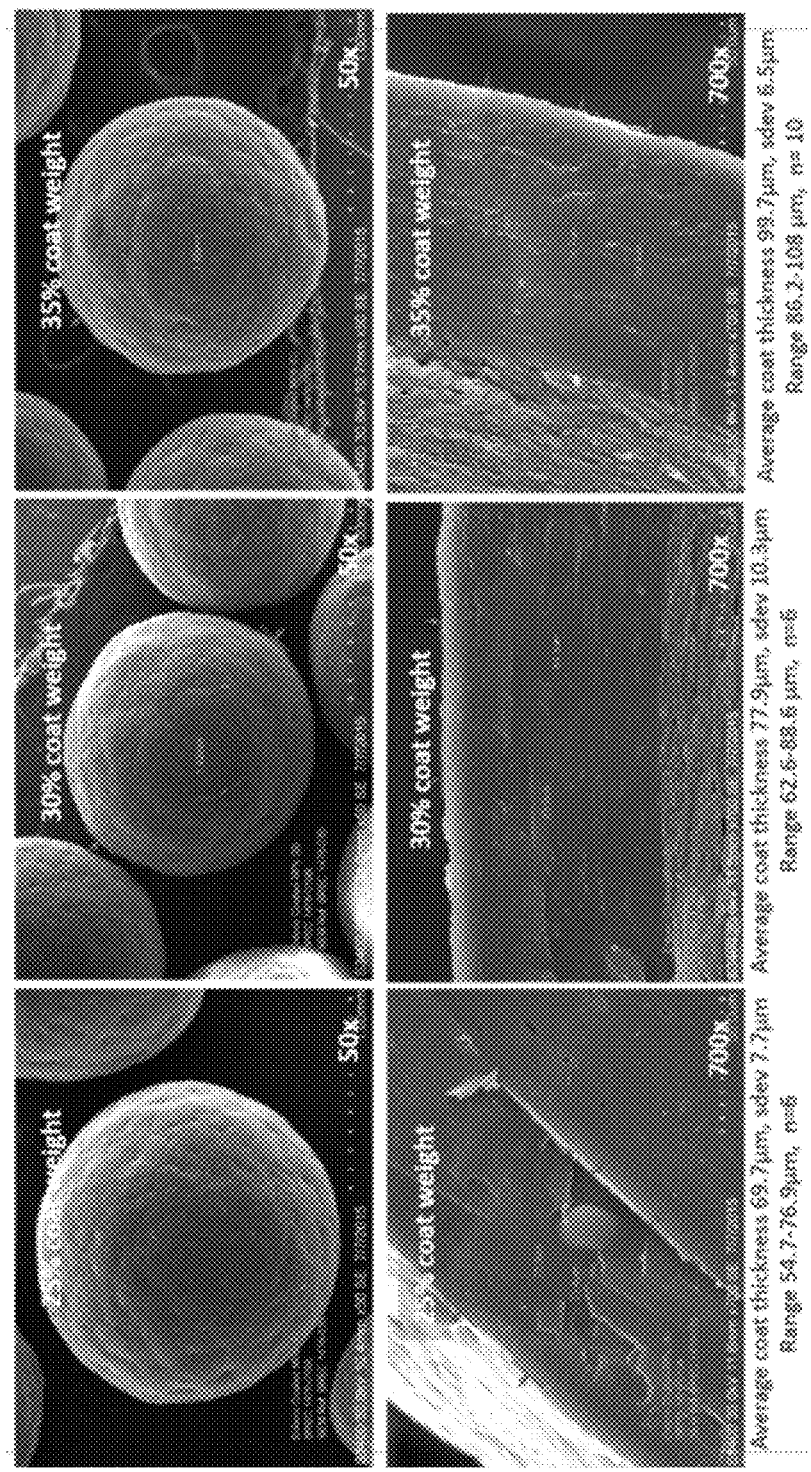
FIG. 4 shows scanning electron microscope images of the enteric-coated SYN-004 particles that release at pH 6.2. Particles coated with EUDRAGIT® L100, EUDRAGIT® S100, and triethyl citrate at a ratio of 72.7/18.2/9.1 and at different coat weights, i.e., 25%, 30%, and 35%, were subjected to scanning electron microscopy. The top panels display the 50× magnification for particle size characterization, and the lower panels display the 700× magnification of particle cross sections (n=6) for each coating % to allow determination of the coating thicknesses.
Figure 5:
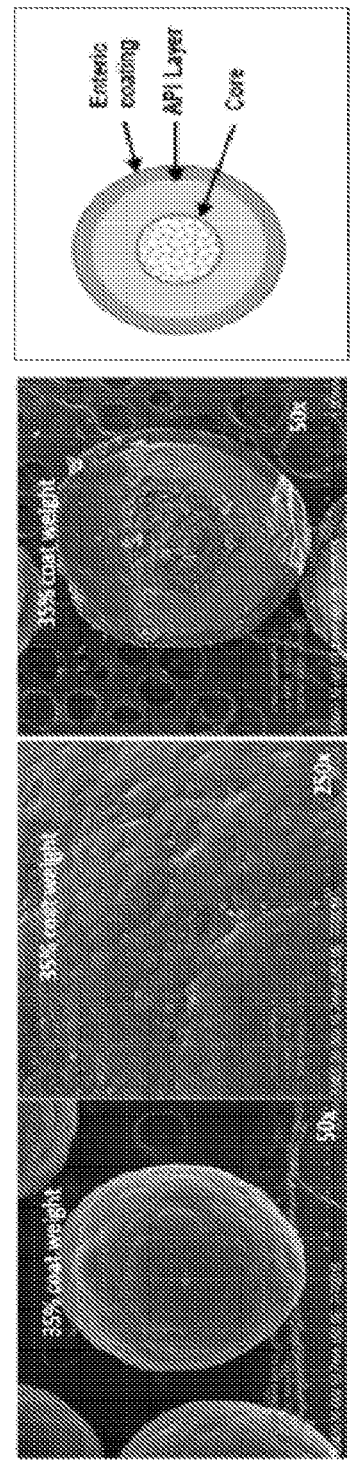
FIG. 5 shows scanning electron microscope images of the enteric-coated SYN-004 particles that release at pH 6.2. Particles coated with EUDRAGIT® L100, EUDRAGIT® S100, and triethyl citrate at a ratio of 72.7/18.2/9.1 at a 35% coat weight were subjected to scanning electron microscopy. The panels, from left to right, display the 50× magnification for particle size characterization, 250× magnification for surface uniformity analyses, 50× magnification of a particle cross section, and a schematic diagram of a particle displaying the three layers.
Figure 8:
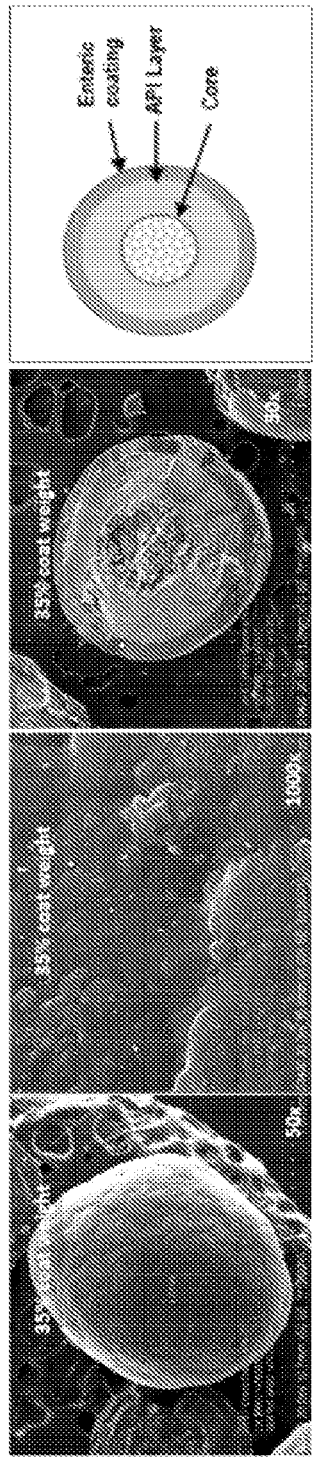
FIG. 8 shows scanning electron microscope images enteric-coated SYN-004 particles that release at pH 6.7. Particles coated with EUDRAGIT® L100, EUDRAGIT® S100, and triethyl citrate at a ratio of 30/60.9/9.1 at a 35% coat weight were subjected to scanning electron microscopy. The panels, from left to right, display the 50× magnification for particle size characterization, 1000× magnification for surface uniformity analyses, 50× magnification of a particle cross section, and a schematic diagram of a particle displaying the three layers.
Figure 9:
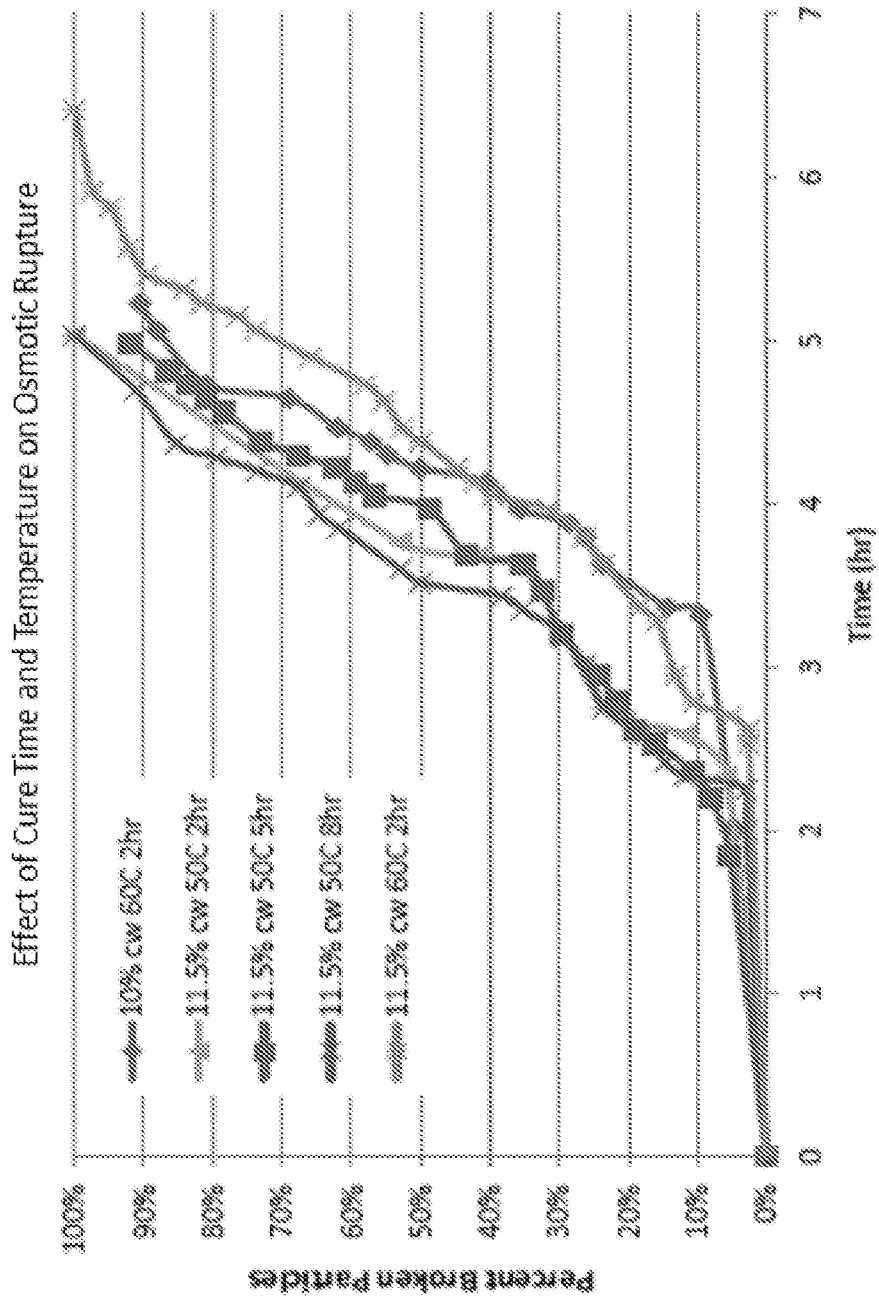
FIG. 9 depicts the osmotic rupture of coated particles. Particles with 10% or 11.5% osmotic coat weights with cure temperatures of 50° C. or 60° C., and cure times of 2, 5, and 8 hours were compared. The indicated pellets were added to a 50 mM $KH_2PO_4$ pH 6.2 buffer at room temperature without stirring and images of the pellets were taken every 5 minutes over 7 hours to evaluate particle disruption. Particle disruption included visible coating changes and significant deformation of the particles. The samples included: 10% coating, cure at 60° C. for 2 hour (diamonds); 11.5% coating, cure at 50° C. for 2 hour (triangles); 11.5% coating, cure at 50° C. for 5 hour (squares); 11.5% coating, cure at 50° C. for 8 hours (Xs); and 11.5% coating, cure at 60° C. for 2 hours (asterisks).

The coated particles were characterized based on coat thickness versus coat weight and mass fraction (weight %) versus particle size (FIG. 3, panels A and B). The collected particles were confirmed to have estimated coat weights of 25% with an average coat thickness of approximately 70 um, 30% with an average 80 um coat thickness, and 35% with an average 100 um coat thickness. The final product particles (35% coating efficiency) were characterized based on the mass fraction versus particle size and it was found that the midpoint of the particle sizes ($D_{50}$) was 1390 um. The coated particles were also characterized by scanning electron microscopy (FIGS. 8 and 9). The particles appeared smooth and uniformly coated with sized of approximately 1.4 mm. Cross sections of the particles (n=6 for each coating %) allowed calculation of the coating thicknesses. The calculated coating thicknesses were 69.7 um for the 25%, 77.9 um for the 30% and 99.7 um for the 35%, similar to what was observed in the coat thickness versus coat weight evaluation (FIG. 3). Additional scanning electron microscopy characterization of the 35% particles displayed a uniform surface and a 50× magnified view of a cross sectioned particle clearly displayed the sucrose core, the SYN-004 layer over the core, and the outer EUDRAGIT® coating (FIG. 5). Based on these data, the 35% pH >6.2 particles were chosen as the prototype for further testing.

Enteric-Coating SYN-004 Formulation with Release at pHs >6.7

The SYN-004-coated sucrose pellet starting material was coated with a mixture of EUDRAGIT® L100, EUDRAGIT® S100, and triethyl citrate at a ratio of 30/60.9/9.1. The parameters of the spray coating (FIG. 2) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The EUDRAGIT® L100, EUDRAGIT® S100, and triethyl citrate at a ratio of 72.7/18.2/9.1 was dissolved in isopropanol and water at a 95/5 ratio. First the isopropanol and water were mixed and then the EUDRAGITs® were added, after which the triethyl citrate was added. The mixture was stirred until dissolved for at least 30 minutes following the addition of the triethyl citrate. The operating parameters of the fluid bed dryer were a gas flow rate of 35 CFM, inlet temperature of 29° C., inlet dew point of 7.5° C., atomizer pressure of 2.5 bar, a spray rate of 2.4 g/min, and a bed temperature of 25° C. The fluid bed process performance was a total solution sprayed of 628.7 g, a run time of 4 hrs and 24 minutes, a bed dump of 105.1 g, a final coat weight estimate of 35% and a coating efficiency of 99.6%. Samples were dried at 35° C. for 2 hours. Samples were collected at intermediate coating weights of 25% and 30% for characterization along with the 35%.

Figure 6:
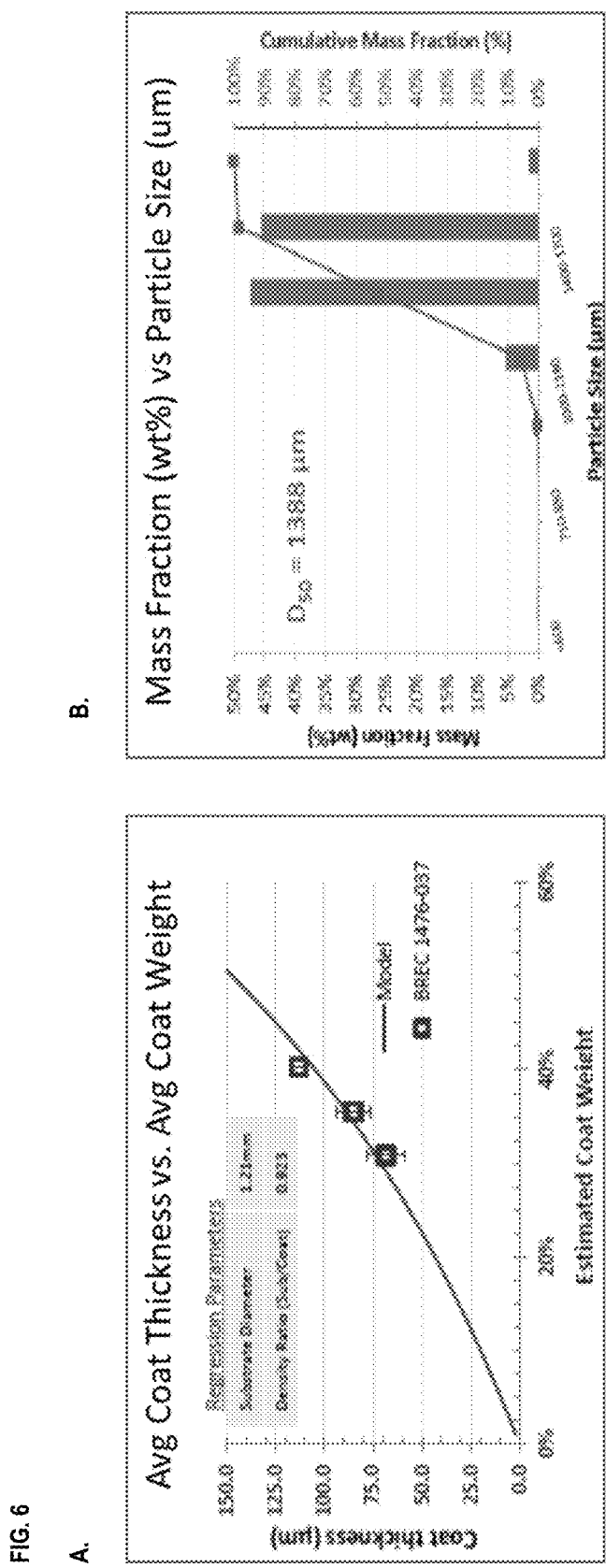
FIG. 6 depicts characterization of the enteric-coated SYN-004 particles that release at pH 6.7. Particles coated with EUDRAGIT® L100, EUDRAGIT® S100, and triethyl citrate at a ratio of 30/60.9/9.1 were characterized based on the average coat thickness versus estimated coat weights (panel A) and the mass fraction versus the particle size (panel B).
Figure 7:
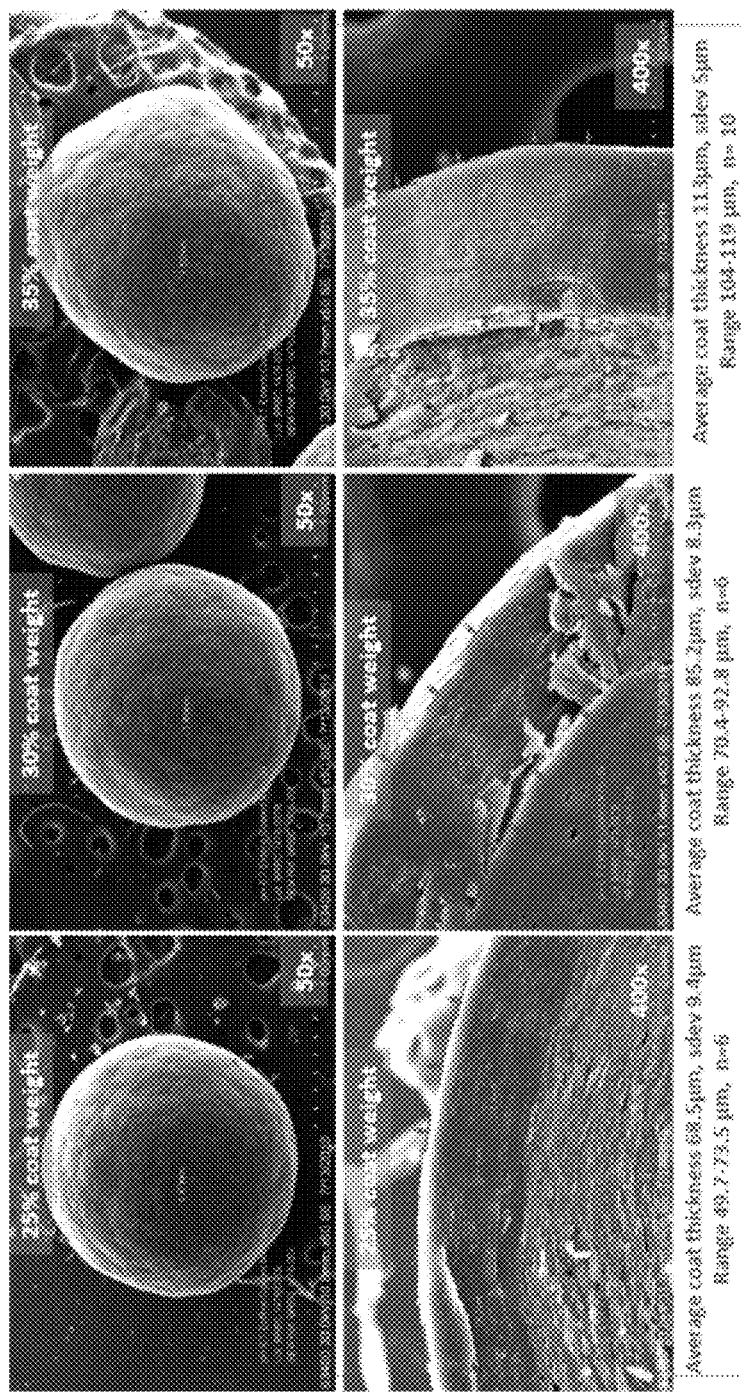
FIG. 7 shows scanning electron microscope images of enteric-coated SYN-004 particles that release at pH 6.7. Particles coated with EUDRAGIT® L100, EUDRAGIT® S100, and triethyl citrate at a ratio of 30/60.9/9.1 and at different coat weights, i.e., 25%, 30%, and 35%, were subjected to scanning electron microscopy. The top panels display the 50× magnification for particle size characterization, and the lower panels display the 400× magnification of particle cross sections (n=6) for each coating % to allow determination of the coating thicknesses.
Figure 10:
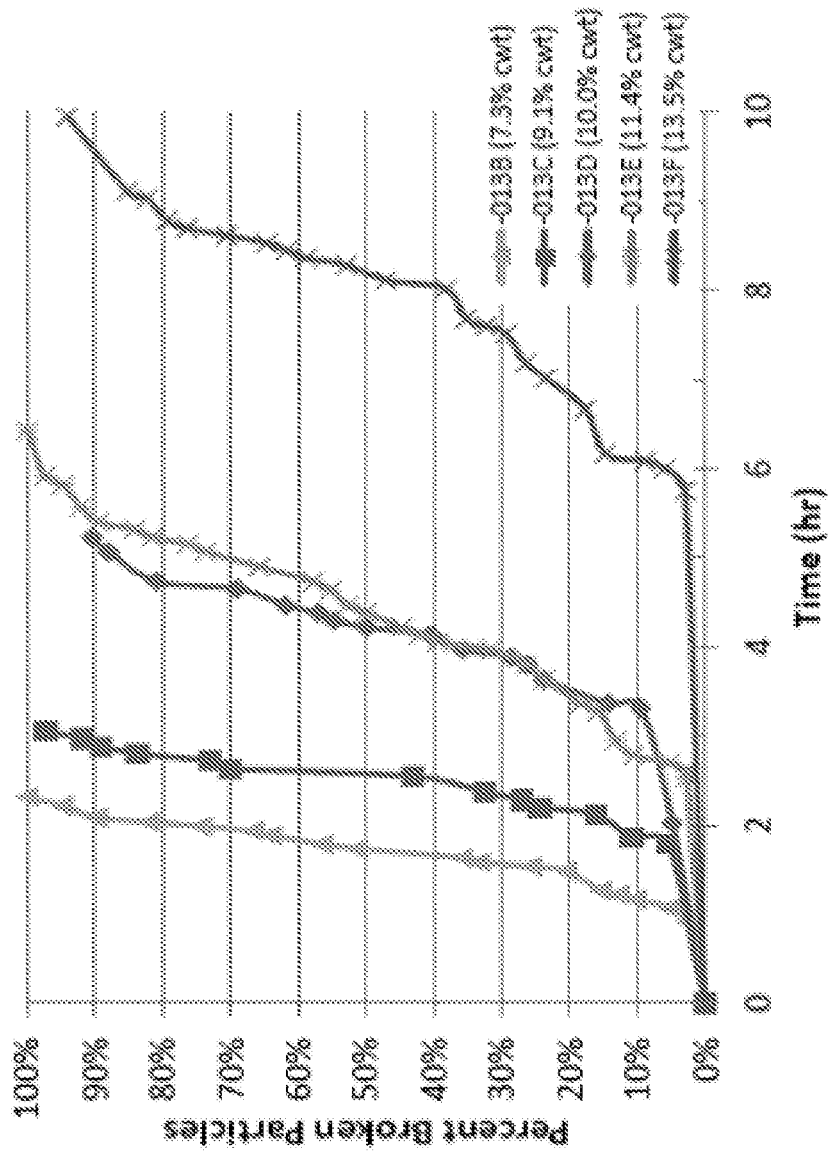
FIG. 10 depicts the osmotic rupture of coated particles. Particles with 7.3%, 9.1%, 10%, 11.4%, or 13.5% osmotic coat weights were compared. The indicated pellets were added to a 50 mM $KH_2PO_4$ pH 6.2 buffer at room temperature without stirring and images of the pellets were taken every 5 minutes over 10 hours to evaluate particle disruption. Particle disruption included visible coating changes and significant deformation of the particles. The samples included: 7.3% coating (triangles); 9.1% coating (squares); 10% coating (diamonds); 11.4% coating (asterisks); and 13.5% coating (Xs).

The coated particles were characterized based on coat thickness versus coat weight and mass fraction (weight %) versus particle size (FIG. 6, panels A and B). Coating was more efficient than expected and the estimated coat weights were 30% (referred to as the expected 25%), 35% (referred to as the expected 30%), and 40% (referred to as the expected 35%), with coat thicknesses of approximately 65 um, 85 um, and 110 um, respectively. The final product particles (40% coating efficiency) were characterized based on the mass fraction versus particle size and it was found that the midpoint of the particle sizes ($D_{50}$) was 1388 um. The coated particles were also characterized by scanning electron microscopy (FIGS. 7 and 8). The particles appeared smooth and uniformly coated with sizes of approximately 1.5 mm. Cross sections of the particles (n=6 or n=10 for each coating %) allowed calculation of the coating thicknesses. The calculated coating thicknesses were 68.5 um for the 25%, 85.2 um for the 30% and 113 um for the 35%, similar to what was observed in the coat thickness versus coat weight evaluation (FIG. 10). Additional scanning electron microscopy characterization of the 35% particles displayed a uniform surface and a 50× magnified view of a cross sectioned particle clearly displayed the sucrose core, the SYN-004 layer over the core, and the outer EUDRAGIT® coating (FIG. 8).

Based on these data, the 35% pH >6.7 particles were chosen as the prototype for further testing.

Osmotic-Rupture Coating SYN-004 Formulation with Timed Release

The SYN-004-coated sucrose pellet starting material was coated with a mixture of 71.4% pulverized croscarmellos sodium (AcDiSol, FMC Biopolymer), 28.6% hydroxyproplycellulose (HPC) in 100 proof ethyl alcohol. This layer was referred to as the sweller layer. The HPC was added to ⅔ of the ethyl alcohol and the AcDiSol was added to ⅓ of the ethyl alcohol. The solution was high shear mixed for 3 minutes at 4000 rpm. The parameters of the spray coating (FIG. 2) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The operating parameters of the fluid bed dryer were a gas flow rate of 35 CFM, inlet temperature of 32° C., inlet dew point of 6.1° C., atomizer pressure of 2.5 bar, a spray rate of 3.4 g/min, and a bed temperature of 28° C. The fluid bed process performance was a total solution sprayed of 385 g, a run time of 1 hr and 53 minutes, a bed dump of 119.1 g, a final coat weight estimate of 37% and a coating efficiency of 82%. No intermediate samples were collected.

The next step was to add the osmotic rupture coating to the SYN-004 particles coated with the sweller layer. The osmotic rupture coating composition was 75% Aquacoat ECD (ethylcellulose dispersion, FMC Biopolymer), and 25% triethyl citrate (TEC) in water. The TEC was added to the Aquacoat ECD and the residual TEC was washed with water and added to solution. The suspension was stirred throughout the run. The parameters of the spray coating (FIG. 2) was using a Niro-Aeromatic Lab Fluid Bed Dryer, Model MP-1 with a bowl size of 3.5 inches, air distribution with a Mod B Plate, a Schlick 970 (tall) nozzle with a 1.2 mm liquid tip size, and a column gap of 10 mm. The operating parameters of the fluid bed dryer were a gas flow rate of 35 CFM, inlet temperature of 51° C., inlet dew point of 8.3° C., atomizer pressure of 2.5 bar, a spray rate of 2.0 g/min, and a bed temperature of 35° C. The fluid bed process performance was a total solution sprayed of 146 g, a run time of 1 hr and 11 minutes, a bed dump of 124, a final coat weight estimate of 13.5% and a coating efficiency of 66%. Intermediate samples were collected at 7.3%, 9.1%, 10%, and 11.5%.

Figure 11:
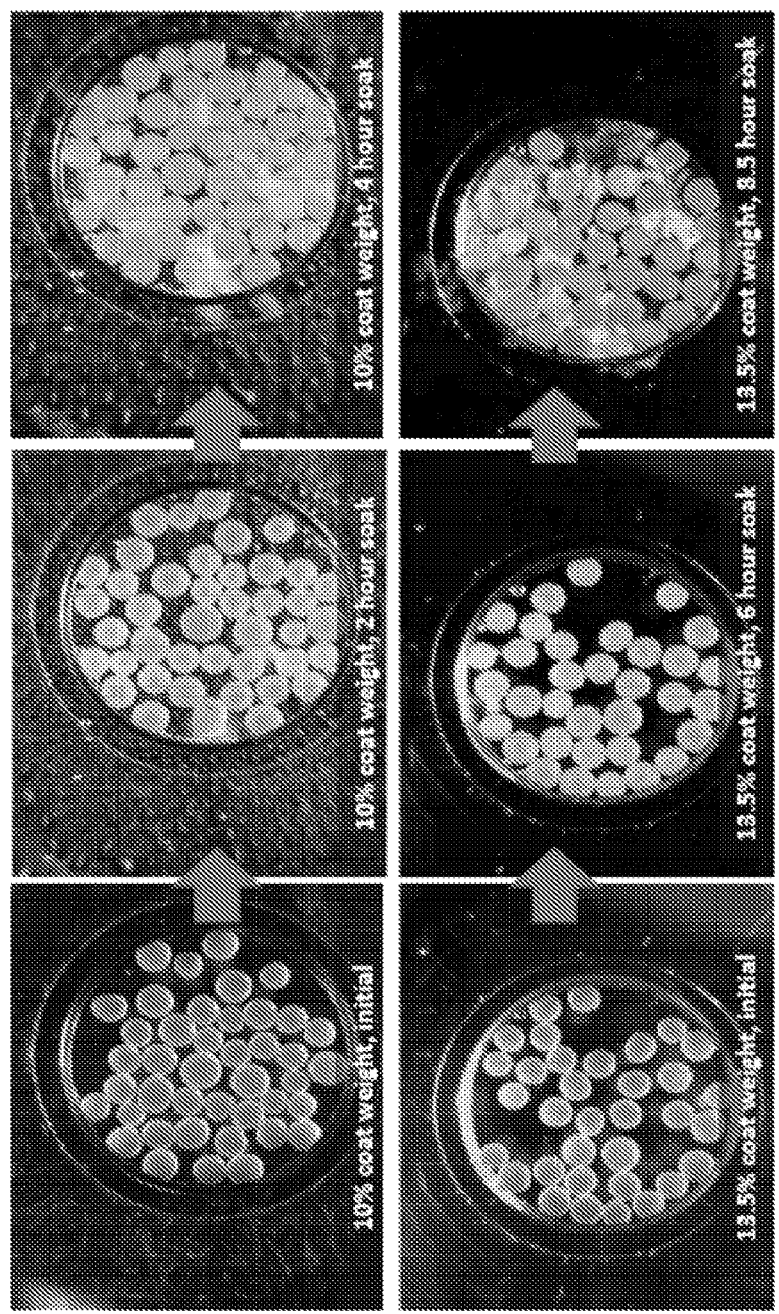
FIG. 11 shows the osmotic rupture of coated particles. Photos of particles with 10% or 13.5% osmotic coat weights are displayed. The indicated pellets were added to a 50 mM $KH_2PO_4$ pH 6.2 buffer at room temperature without stirring. The top panels display the 10% coat weight particles at 0, 2, and 4 hours of soaking. The bottom panels display the 13.5% coat weight particles at 0, 6, and 8.5 hours of soaking.

Following coating, the particles were cured. Multiple curing temperatures and times were evaluated for osmotic rupture (burst time) and beta-lactamase enzyme activity. The initial analyses compared particles with 10% or 11.5% osmotic coat weights with cure temperatures of 50° C. or 60° C., and cure times of 2, 5, and 8 hours (FIG. 9). Pellets were added to a 50 mM $KH_2PO_4$ pH 6.2 buffer at room temperature without stirring, images of the pellets were taken every 5 minutes to evaluate particle disruption as visual disruption of the coating, significant deformation of the particles and the presence of external AcDiSol. The data demonstrated that the 10% and 11.5% coat weights were not of sufficient thickness to reach the desired 4 hours particle burst delay, as the particles started to appear broken between 2 and 3 hours. In addition, the cure time and temperature of 60° C. for 2 hours appeared best. Based on these data, the 10% SYN-004 pellets were recoated to 11.4% and 13.5% with a cure temperature of 60° C. for 2 hours and retested as described (FIG. 10). Pellets with the 13.5% coating remained intact for over 5 hours with 50% rupture occurring at 8 hours, while the 10% and 11.4% began to break at 2.5 or 3 hours with 50% rupture occurring at 4 hours. The appearance of the 10% and 13.5% particles after soaking for 0 to 8.5 hours is displayed in FIG. 11.

Figure 12:
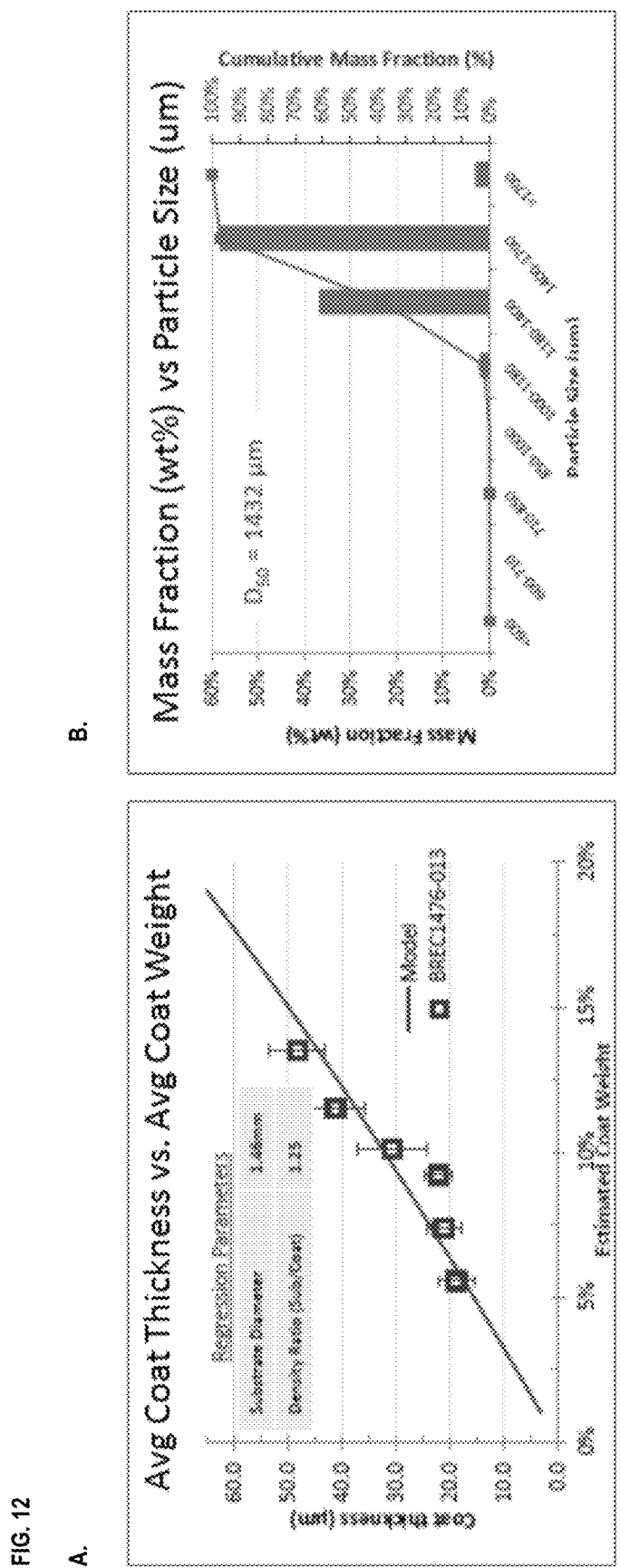
FIG. 12 depicts characterization of the osmotic rupture SYN-004 particles. The particles were characterized based on the average coat thickness versus estimated coat weights (panel A) and the mass fraction versus the particle size (panel B).
Figure 13:
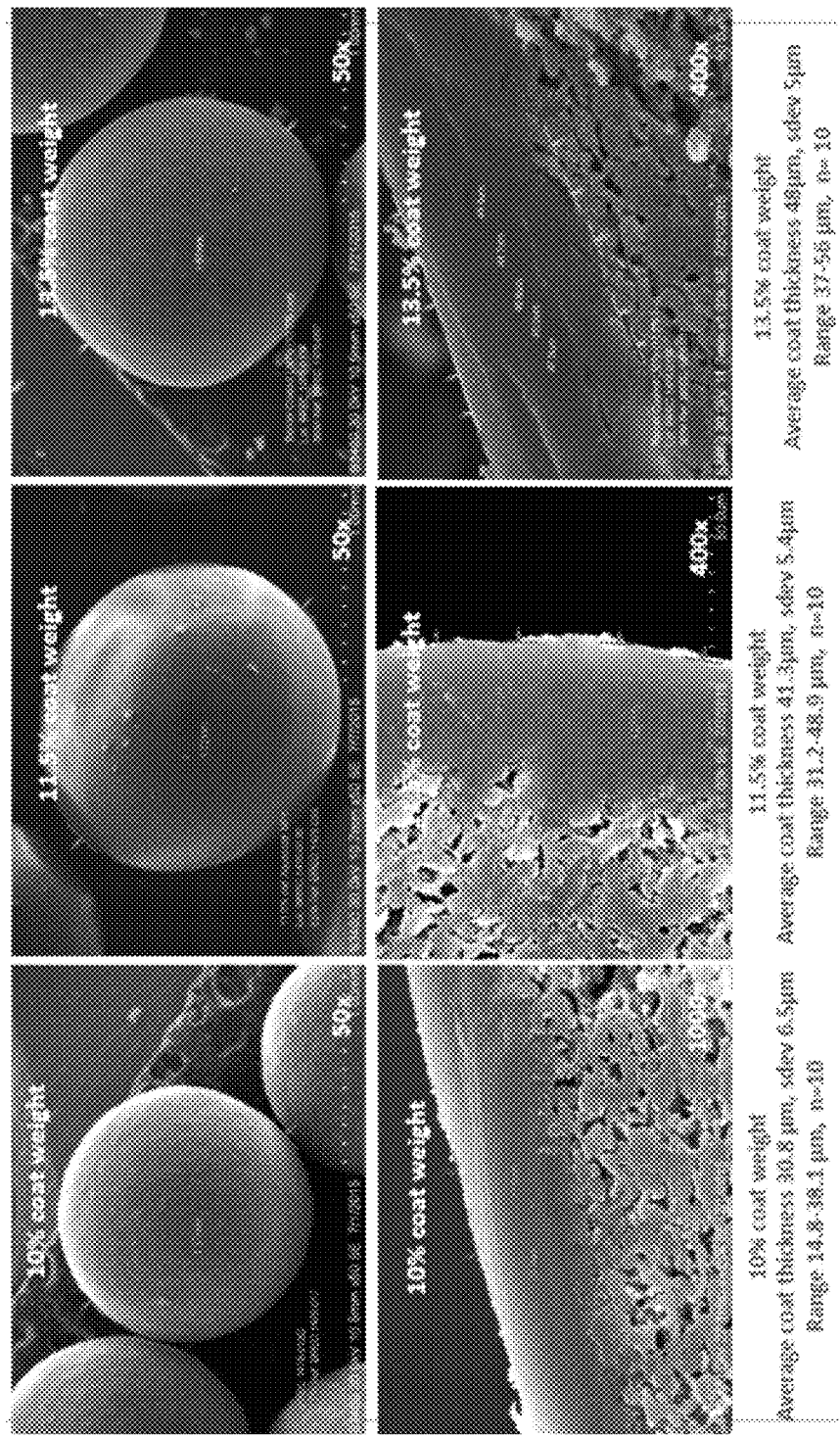
FIG. 13 shows scanning electron microscope images of the osmotic rupture SYN-004 particles. The osmotic rupture particles of different coat weights, 10%, 11.5%, and 13.5% were subjected to scanning electron microscopy. The top panels display the 50× magnification for particle size characterization, and the lower panels display the 1000× or 400× magnification of particle cross sections (n=10) for each coating % to allow determination of the coating thicknesses.
Figure 14:
FIG. 14 shows scanning electron microscope images of the osmotic rupture SYN-004 particles. The 13.5% coating weight osmotic rupture particles were subjected to scanning electron microscopy. The panels, from left to right, display the 50× magnification for particle size characterization, 250× magnification for surface uniformity analyses, 50× magnification of a particle cross section, and a schematic diagram of a particle displaying the three layers.

The coated particles were characterized based on coat thickness versus coat weight and mass fraction (weight %) versus particle size (FIG. 12). Coating was as expected with coat weights ranging from 7% to 13%, and thicknesses of 20 um to 50 um. The final product particles (13.5% coating weight) were characterized based on the mass fraction versus particle size and it was found that the midpoint of the particle sizes ($D_{50}$) was 1432 um. The coated particles were also characterized by scanning electron microscopy (FIGS. 13 and 14). The particles appeared smooth and uniformly coated with sizes of approximately 1.5 mm. Cross sections of the particles (n=10 for each coating %) allowed calculation of the coating thicknesses. The calculated coating thicknesses were 30.8 um for the 10% coat weight, 41.3 um for the 11.5% coat weight, and 48 um for the 13.5% coat weight. Additional scanning electron microscopy characterization of the 13.5% coat weight particles displayed a uniform surface and a 50× magnified view of a cross sectioned particle displayed the sucrose core, the SYN-004, and coating layers (FIG. 14).

Figure 15:
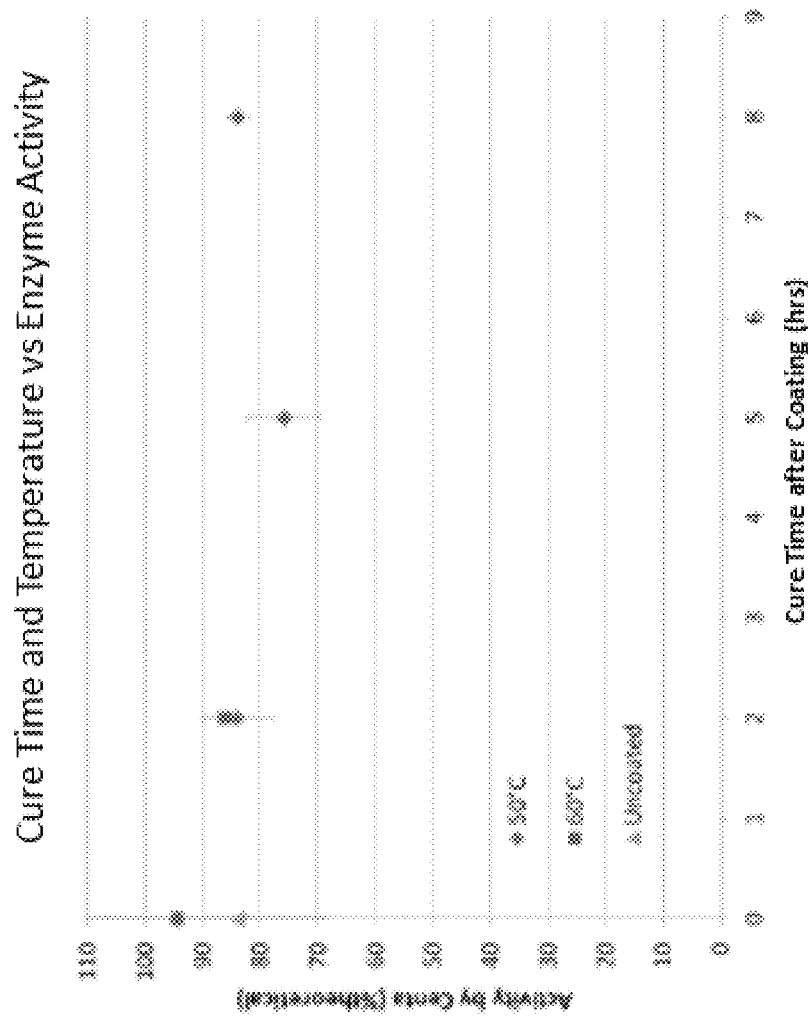
FIG. 15 shows evaluations of cure time and temperature on enzyme activity for osmotic rupture SYN-004 particles. The SYN-004 coated sucrose pellets were coated with a sweller layer and then coated with the osmotic rupture layer. The osmotic layer required a curing step. Cure temperatures of 50° C. or 60° C., and cure times of 0, 2, 5, and 8 hours were evaluated. Pellets were added to a pH 6.8 potassium phosphate buffer and stirred overnight to ensure removal of the entire coating. Aliquots of the buffer were analyzed for SYN-004 biological activity using the CENTA chromogenic microtiter plate assay. Activity is displayed as % of theoretical activity based on the amount of SYN-004 protein present in each formulation. Uncoated (SYN-004 pellet starting material) is displayed as the triangle. 50° C. curing temperature is displayed as the diamond, and 60° C. is displayed as the square.

To verify that the conditions chosen to cure the osmotic coating did not affect SYN-004 biological activity, an additional study was performed. Osmotic rupture, 13.5% coat weight SYN-004 pellets, under different curing conditions were evaluated for retention of biological activity (FIG. 15). Osmotic rupture pellets were added to a pH 6.8 potassium phosphate buffer and stirred overnight to ensure removal of the entire coating. Aliquots of the buffer were analyzed for SYN-004 biological activity using the CENTA chromogenic microtiter plate assay. The data demonstrate that cure times ranging from 8 hours at 50° C. or 2 hours at 60° C. did not affect SYN-004 biological activity. The SYN-004 starting material, the uncoated pellets, displayed 84.0%+15.2% activity, the uncured particles, 94.5+12.2% activity, 50° C. for 2 hrs, 84.0±6.2% activity, 50° C. for 5 hr, 75.8+6.4%, 50° C. for 8 hr, 83.9+1.9% activity, and 60° C. for 2 hrs, 86.1+1.4% activity.

Based on these data, the 13.5%, cured at 60° C. for 2 hours, osmotic rupture particles were chosen as the prototype for further testing.

Figure 16:
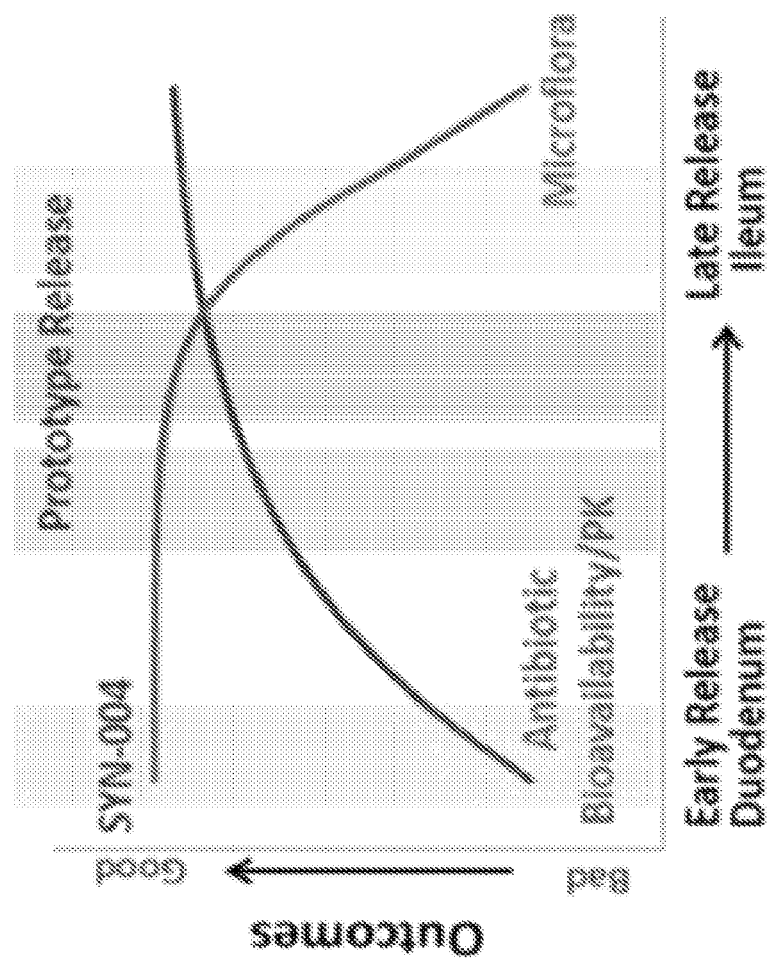
FIG. 16 provides a schematic representation of the criteria for choosing a modified-release formulation of SYN-004 for oral delivery with oral antibiotics. The desired outcome is to not interfere with antibiotic absorption from the intestinal track to maximize antibiotic bioavailability, and to degrade antibiotic that is in the intestinal tract prior to causing damage to the microflora.
Figure 17:
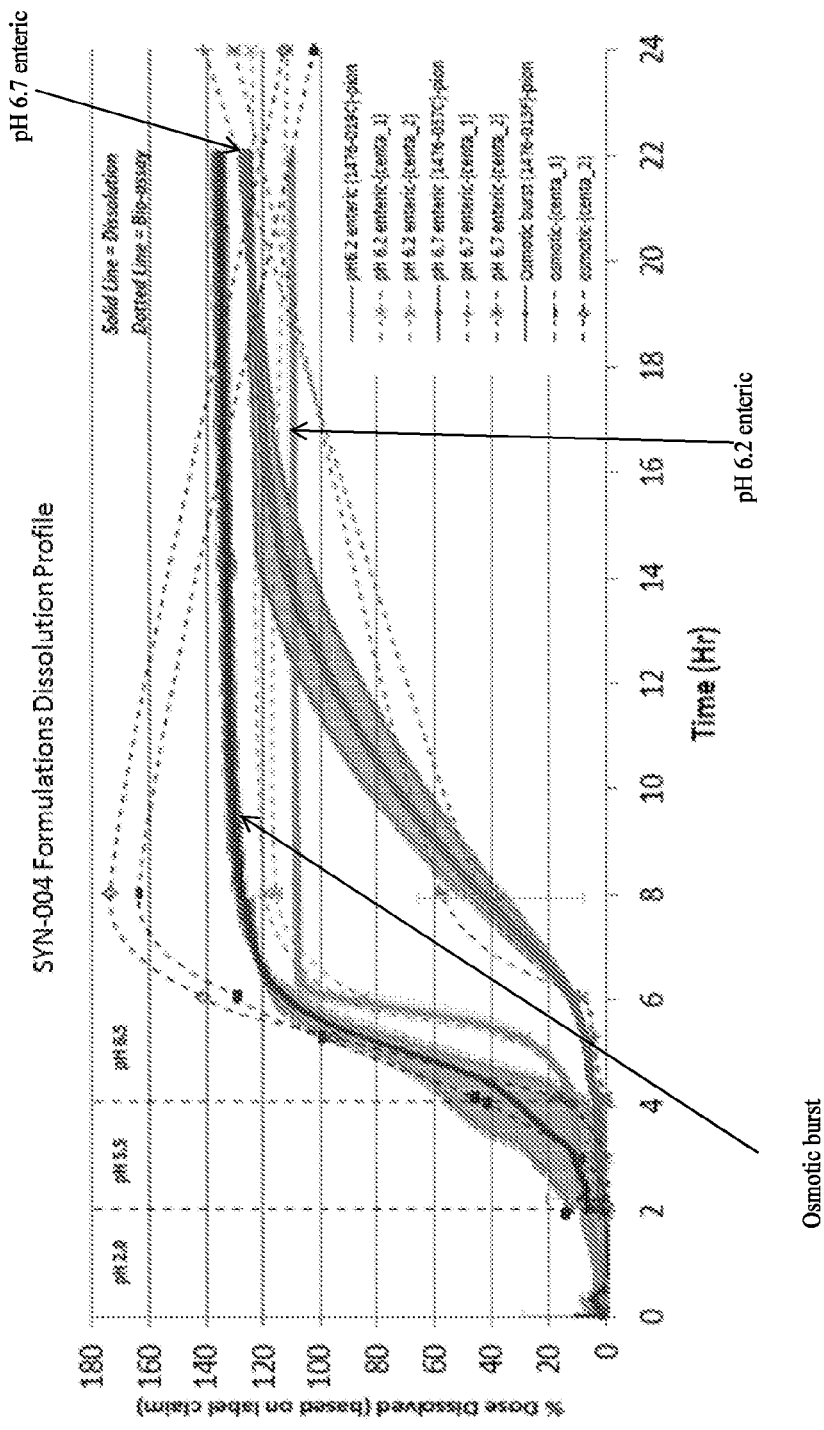
FIG. 17 depicts the SYN-004 pellet dissolution profile. The three SYN-004 formulations (7.5 mg active) were incubated in 0.01N HCl (pH 2.0) for 2 hours, pH 5.5 for 2 hours, and pH 6.5 up to 24 hours. Samples were tested for protein concentration by measuring absorbance at 280 nm (solid lines) and SYN-004 biological activity using the CENT chromogenic assay (dotted lines). The formulations were enteric pH 6.2, enteric pH 6.7, and osmotic as described in Example 2
Figure 18:
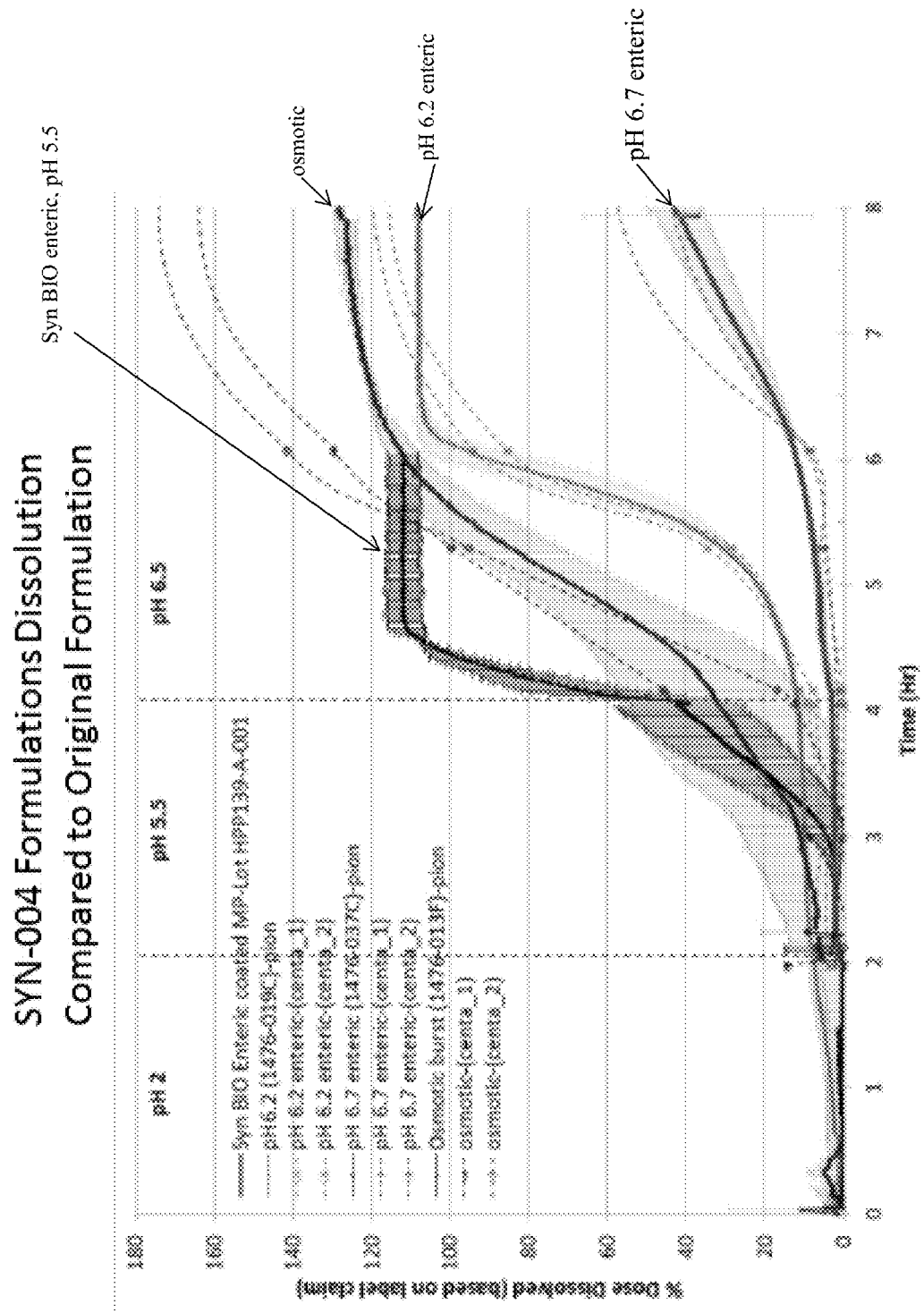
FIG. 18 depicts the SYN-004 pellet dissolution profile compared to original SYN-004 formulation. The original (enteric, pH 5.5) and the three SYN-004 formulations (7.5 mg active) were incubated in 0.01N HCl (pH 2.0) for 2 hours, pH 5.5 for 2 hours, and pH 6.5 up to 24 hours. Samples were tested for protein concentration by measuring absorbance at 280 nm (solid lines) and SYN-004 biological activity using the CENT chromogenic assay (dotted lines). The formulations were SYN-004 original (SynBio enteric, pH 5.5), enteric pH 6.2, enteric pH 6.7, and osmotic, as described in Example 2.

The criteria for identifying a promising modified-release formulation of SYN-004 for oral use with oral antibiotics was to identify SYN-004 formulation or formulations that have the desired enzyme release profile to maximize antibiotic bioavailability while minimizing the antibiotic's effect on the intestinal microflora (FIG. 16). The three SYN-004 formulations generated as described in Example 2 were further characterized. The three formulations chosen were: 1) enteric-coated pH 6.2 release, 2) enteric-coated pH 6.7 release, and 3) an osmotic rupture formulation. The characteristics of these formulations are displayed in TABLE 4.

TABLE 4

| Formulation Prototypes | Release pH | Coating %/thickness | Release characteristics | | | | | Biological Activity |
|---|---|---|---|---|---|---|---|---|
| | | | 2 hr | 4 hr | Lag Time | Duration (hr) | Total (hr) | Compared to SYN-004 |
| SYN-004 (Control) | 5.5 | ~55 um | 0-1% | 20-50% | NA | 1.3 | 2.25 | 100% |
| Enteric 6.2 | 6.2 | 35%/100 um | 0-10% | 5-15% | NA | 2.0 | 4 + 2 | 135% |
| Enteric 6.7 | 6.7 | 35%/113 um | 0-1% | 0-5% | NA | 8-10 | 4 + 8-10 | 120% |
| Osmotic | NA | 13.5%/48 um | 0-5% | 5-50% | 3 hr | 3 | 6 | 105% |

Figure 21:
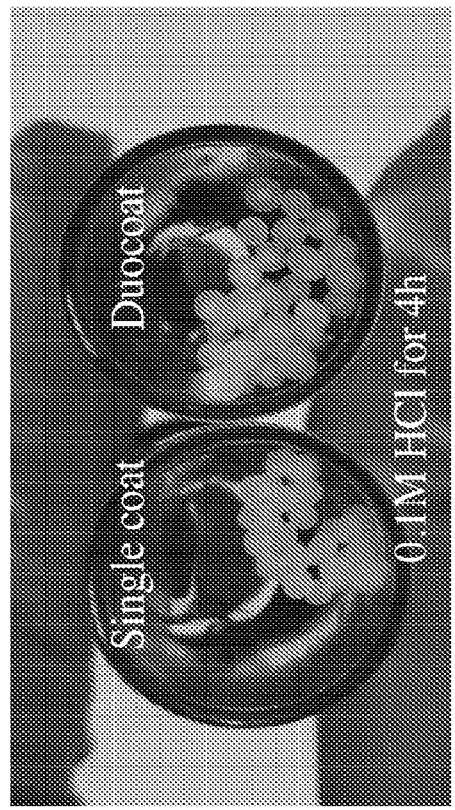
FIG. 21 shows FS 30 D coated pellets (Formulation 1 on the left and 2 on the right) in 0.1M HCl for 4 hours.
Figure 22:
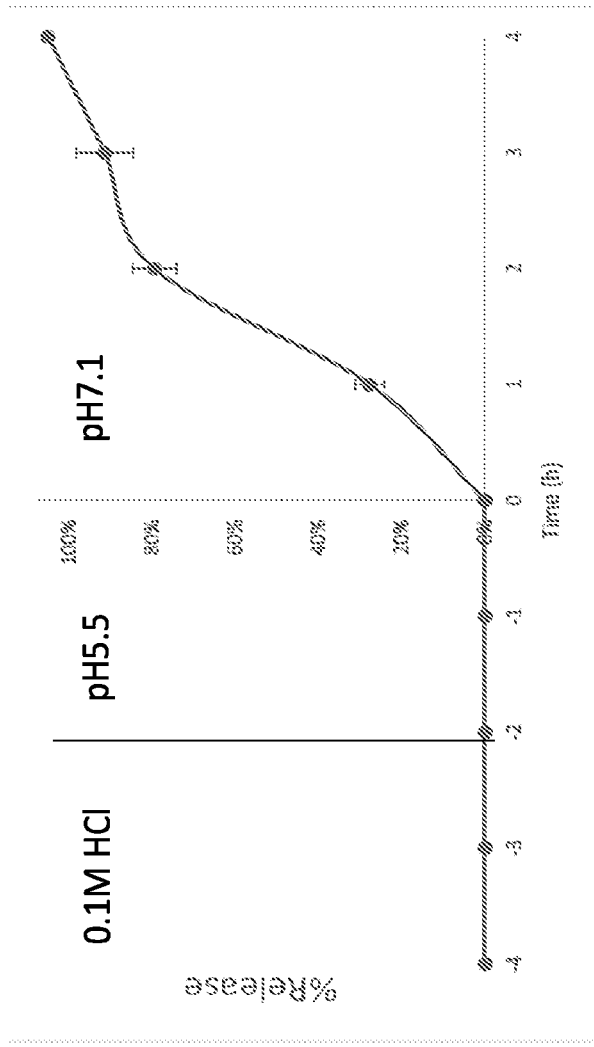
FIG. 22 shows a dissolution profile of Formulation 10: FS 30 D coated gelatin capsule (FS 30 D pellets).

The three formulations were evaluated in vitro to characterize their dissolution profiles and to verify that the SYN-004 enzyme retained biological activity in each formulation (FIGS. 21 and 22). For each formulation, a total of 7.5 mg of SYN-004 active agent was incubated in 25 ml of a pH 2.0 solution (0.01N HCl) for 2 hours to mimic the conditions of the stomach following ingestion. The pH was then increased to 5.5 (total volume 75 ml in potassium phosphate) for an additional 2 hours. The pH was then adjusted to 6.5 using 10N KOH. All incubations were performed at 37.5° C. with agitation of 250 rpm. For each sample, 20 ul was collected into a 2 ml volumetric post auto sampler at the indicated time points. Samples were evaluated for protein concentration using absorbance at 280 nm and for SYN-004 biological activity using the CENTA chromogenic assay. The Enteric pH 6.2 formulation showed minimal release in acidic environments with a duration of release of approximately 2 hours. The Enteric pH 6.7 formulation showed minimal release in acidic environments followed by a duration of release of approximately 8-10 hours. The Osmotic Rupture formulation providing pH-independent release, displayed a 3 hour lag followed by a duration of release of 3 hours. The original SYN-004 formulation (Enteric, pH 5.5) showed minimal release in acidic environments followed by a duration of release of 1.3 hours. The data demonstrate that all formulations maintain SYN-004 biological activity for the duration of the three-stage dissolution test for 24 hours. The formulations have the desired release characteristics for testing in an animal model with an oral antibiotics such as amoxicillin.

Example 3: Preparation of Capsules Filled with SYN-004 Formulations for In Vivo Evaluations The three SYN-004 formulation pellets, as described in Example 2, and the original SYN-004 formulation pellets (Enteric 5.5) as described in Example 1, were used to fill size 0 gelatin capsules to achieve a dose of 50 mg of SYN-004 active agent (TABLE 5). The list of components and the amounts in these capsules are provided in TABLE 6 below. A volumetric fill was used with a 100% weight sort and a +3% target rejection limit. There was less than a 3% RDS fill variation. The average mass of the empty gelatin capsules was 93 mg.

5.5 for an additional 2 hours. The pH was then adjusted to 6.5 using 10N KOH. All incubations were performed at 37.5° C. with agitation of 250 rpm. For each sample, 20 ul was collected into a 2 ml volumetric post auto sampler at the indicated time points. Samples were evaluated for protein concentration using absorbance at 280 nm. The data demonstrate that no damage to the pellets occurred during capsule filling. A slower than expected release rate was observed for the Enteric pH 6.2 and the Enteric pH 6.7 formulations.

Following encapsulation, the formulations retained the desired release characteristics for testing in an animal model with an oral antibiotics such as amoxicillin.

Example 4. Evaluation of the Modified-Release Formulations of SYN-004 in Normal Piglets A study was performed using normal piglets to compare the three, modified-release formulations of SYN-004 as described in Example 2, and the original SYN-004 formu-

TABLE 5

| Formulation Prototypes (50 mg active) | Capsule Color | Target Fill Weight (mg) | Average Fill Weight (mg) | % Target | % RSD | % Capsules Rejected (±3% Limits) |
|---|---|---|---|---|---|---|
| SYN-004 (Control) | clear | 298 | 297 | 99.9% | 1.0% | 0.0% |
| Enteric 6.2 | green | 360 | 359 | 99.9% | 1.4% | 0.9% |
| Enteric 6.7 | orange | 401 | 402 | 100.2% | 1.2% | 2.3% |
| Osmotic | white | 447 | 447 | 100% | 1.1% | 3.2% |

TABLE 6

Composition of osmotic rupture, enteric pH 6.2, and enteric pH 6.7 SYN-004 50 mg active capsules

| Component | Osmotic Rupture | | Enteric pH 6.2 | | Enteric pH 6.7 | |
|---|---|---|---|---|---|---|
| | mg | % Total | mg | % Total | mg | % Total |
| Sucrose sphere | 73.7 | 16.5 | 73.7 | 20.5 | 73.7 | 18.4 |
| Hydroxypropylcellulose | 140.0 | 31.3 | 110.5 | 30.7 | 110.5 | 27.5 |
| SYN-004 | 50.0 | 11.2 | 50.0 | 13.9 | 50.0 | 12.5 |
| EUDRAGIT L100 | — | — | 87.5 | 24.3 | 49.1 | 12.2 |
| EUDRAGIT S100 | — | — | 21.9 | 6.1 | 98.2 | 24.5 |
| AcDiSol | 110.0 | 24.8 | — | — | — | — |
| Aquacoat ECD | 29.3 | 6.6 | — | — | — | — |
| Buffer salts | 5.0 | 1.1 | 5.0 | 1.4 | 5.0 | 1.3 |
| Talc | 38.2 | 8.6 | — | — | — | — |
| Triethyl citrate | — | — | 10.9 | 3.0 | 14.7 | 3.7 |
| Subtotal | 446 | 100.0 | 360 | 100.0 | 401 | 100.0 |
| Hard gelatin capsule #0 | 93.0 | | 93.0 | | 93.0 | |
| Total | 539 | | 445 | | 494 | |

Figure 19:
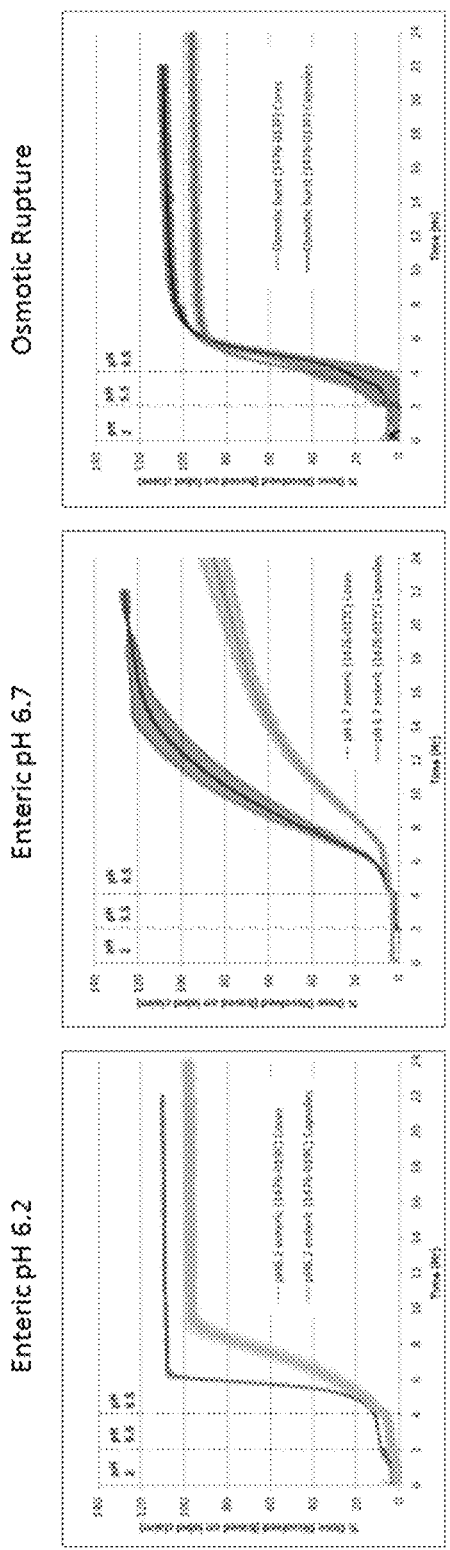
FIG. 19 depicts the capsule versus pellet dissolution profiles for the three SYN-004 formulations. Capsules or pellets (cores) of the three SYN-004 formulations were incubated in 0.01N HCl (pH 2.0) for 2 hours, pH 5.5 for 2 hours, and pH 6.5 for up to 24 hours. Samples were tested for protein concentration by measuring absorbance at 280 nm. The formulations were Enteric pH 6.2, left panel, Enteric pH 6.7, middle panel, and Osmotic, right panel.
Figure 20:
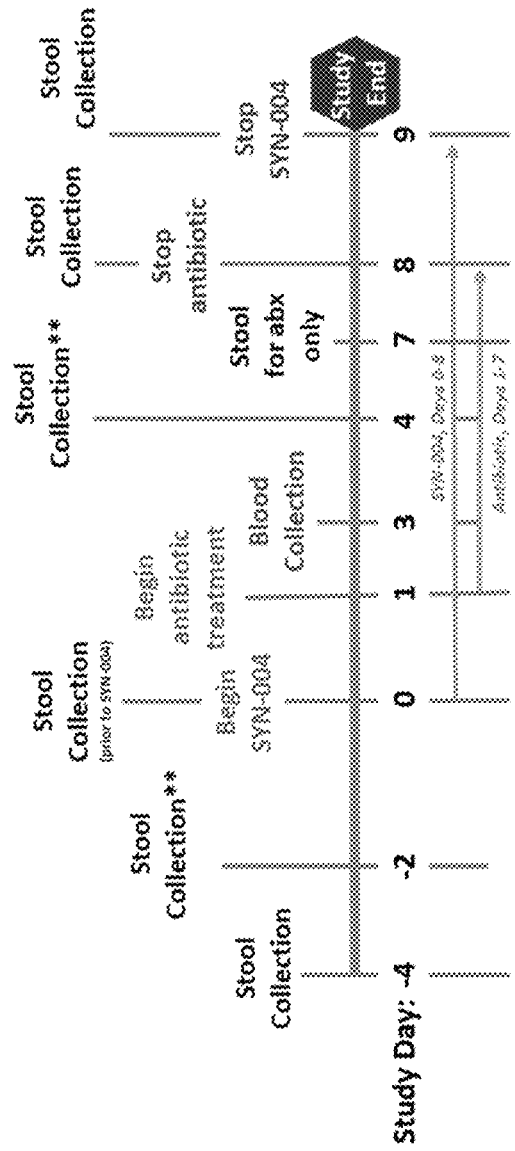
FIG. 20 shows a timeline of piglet dosing. Animals received SYN-004 for 9 days starting on Day 0. Animals received oral amoxicillin for 7 days starting on Day 1. Stool was collected at 5 times, Day −7, Day −4, Day 4, Day 8, and Day 9. Blood was collected at 3 times during Day 2.

The dissolution of the SYN-004 pellets from the capsules was evaluated and compared to the data obtained from dissolution of the SYN-004 pellets prior to encapsulation (FIG. 19). The dissolution study was performed as described previously, however, instead of using 7.5 mg of pellets, one capsule containing 50 mg of active SYN-004 was used. Briefly, one capsule of each formulation, except SYN-004 original (Enteric pH 5.5) was incubated in a pH 2.0 solution (0.01N HCl) for 2 hours to mimic the conditions of the stomach following ingestion. The pH was then increased to lation (Enteric pH 5.5) as described in Example 1, delivered orally with oral amoxicillin, to evaluate the effect on amoxicillin serum levels and protection of the microbiome from amoxicillin-induced dysbiosis (FIG. 20).

A total of 25, two month old Yorkshire piglets, approximately 20 kg each, were used for this study. All 25 animals were treated with oral amoxicillin twice a day for a total of 7 days, in addition, Groups 2-5 received SYN-004 four times a data starting the day before amoxicillin treatment for a total of 9 days (TABLE 7).

TABLE 7

Piglet Study Design

| Group (N = 5) | SYN-004 | SYN-004 Delivery | Antibiotic Delivery |
|---|---|---|---|
| 1 | None | None | Amoxicillin suspension (40 mg/kg/day) Oral, each dose 20 mg/kg BID 7 am, 5 pm |
| 2 | SYN-004 (original formula) Clear capsules | 1 capsule (50 mg active) QID 7 am, 12 pm, 5 pm and 10 pm | |
| 3 | SYN-004 Formulation #2 Green Capsules | | |
| 4 | SYN-004 Formulation #3 Orange Capsules | | |
| 5 | SYN-004 Formulation #4 White Capsules | | |

Three pre-treatment fecal samples were obtained, at Day −4, Day −2, and Day 0 (prior to SYN-004 treatment. The fecal samples were collected using the OMNIgene GUT sample collection kits (OMR-200, DNA Genotek, Ontario, Canada) and stored at room temperature away from light until all samples were collected. DNA isolated from the fecal samples was subjected to deep sequencing of the intestinal microbiome and analyses. Additional fecal samples were collected at Day −2, and Day 4. These samples were collected into 50 ml conical tubes and quickly frozen and stored at −80° C. These samples were submitted for amoxicillin quantification.

On Study Day 0, Groups 2-5 (Pigs 6-25) received one size 0 capsule of one of each of the four SYN-004 formulations, containing 50 mg of SYN-004, orally, four times a day at 7 am, 12 pm, 5 pm, and 10 pm for a total of 9 days. Pigs were fed 3 times a day, after SYN-004 dosing at 7 am, after SYN-004 dosing at 12 pm, and after SYN-004 dosing at 5 pm. Beginning on Study Day 1, all groups, 1-5 (Pigs 1-25), received oral amoxicillin (fruit flavored oral suspension, Sandoz, NDC: 0781-6157-46, Lot #FB0703; 20 mg/kg) twice a day at 7 am and at 5 pm, for a total of 7 days. Animals received the amoxicillin first, followed by the SYN-004, then feeding.

On Day 3, after 5 amoxicillin doses, animals were bled and serum collected. Blood was collected aseptically from the vena cava from anesthetized animals. Three blood draws were performed, at 1 hr, 3 hrs, and 6 hrs after amoxicillin administration. A Telazol cocktail was administered intramuscularly at a minimal dose (1 mL or less per 50 lbs) to achieve light anesthesia/sedations. At each timepoint, approximately 9 mL of blood was collected into a serum separator vacutainer tube. After coagulation, samples were centrifuged and the serum was transferred to a cryovial and stored at −80° C. until shipment to the evaluation laboratory (Sannova Analytical, Inc., Somerset, N.J.).

Amoxicillin levels in the pig serum were quantified using a validated liquid chromatography method with MS/MS detection. A standard curve was prepared in negative control pig serum and had 8 points ranging from 100.724 ng/mL to 10072.381 ng/mL of amoxicillin. The limit of detection of the assay was 100 ng/mL. The amoxicillin levels in the animals that received amoxicillin alone showed peak levels at 3 hours ranging from 1162 to 2318 ng/mL that decreased to 667 to 1161 ng/mL by 6 hrs (TABLE 8). Amoxicillin was not detected in the serum of any animal at any time point when the animals received SYN-004+amoxicillin (TABLE 8). These data verify that the SYN-004 original formulation (enteric pH 5.5; TABLE 1) interfered with amoxicillin absorption and that each of the three new modified-release formulations also interfered with amoxicillin absorption. Additional modified-release formulations of SYN-004 were generated and evaluated.

TABLE 8

Amoxicillin levels in pig serum

| | | Amoxicillin (ng/mL) | | |
|---|---|---|---|---|
| Group | Pig | 1 hour | 3 hours | 6 hours |
| 1 | 1 | 965.5 | 2013.1 | 754.0 |
| | 2 | 1660.6 | 1424.0 | 667.7 |
| | 3 | 2317.8 | 1878.5 | 1161.4 |
| | 4 | 1169.3 | 1162.0 | 925.2 |
| | 5 | 1257.2 | 1548.9 | 1089.9 |
| 2 | 6 | BLQ | BLQ | BLQ |
| | 7 | BLQ | BLQ | BLQ |
| | 8 | BLQ | BLQ | BLQ |
| | 9 | BLQ | BLQ | BLQ |
| | 10 | BLQ | BLQ | BLQ |
| 3 | 11 | BLQ | BLQ | BLQ |
| | 12 | BLQ | BLQ | BLQ |
| | 13 | BLQ | BLQ | BLQ |
| | 14 | BLQ | BLQ | BLQ |
| | 15 | BLQ | BLQ | BLQ |
| 4 | 16 | BLQ | BLQ | BLQ |
| | 17 | BLQ | BLQ | BLQ |
| | 18 | BLQ | BLQ | BLQ |
| | 19 | BLQ | BLQ | BLQ |
| | 20 | BLQ | BLQ | BLQ |
| 5 | 21 | BLQ | BLQ | BLQ |
| | 22 | BLQ | BLQ | BLQ |
| | 23 | BLQ | BLQ | BLQ |
| | 24 | BLQ | BLQ | BLQ |
| | 25 | BLQ | BLQ | BLQ |

BLQ: Below the limit of quantification, 100 ng/mL

Example 5: Additional Modified-Release Formulations

Additional modified-release formulations of SYN-004 were generated and tested. The starting material for the formulations was SYN-004-coated sucrose pellets that lacked the outer, enteric-coating. The SYN-004-coated sucrose pellets were similar to those described in Example 2. The new formulations utilized one of two different enteric coatings that dissolved at pHs >7.0 on the SYN-004-coated sucrose pellets (EUDRAGIT® FS 30 D or EUDRAGIT® S100). In addition, some formulations contained a Duocoat inner layer on top of the SYN-004 coated sucrose pellets and below the outer EUDRAGIT® FS 30 D or S100 enteric-coatings. Duocoat may allow more rapid dissolution of the SYN-004 enzyme following dissolution of the other EUDRAGIT® coatings at pH 7.0 (Liu, et al.). Notably, another layer of enteric-coating was included on the capsules. Two different types of capsules were used, a gelatin capsule or a delayed release capsule. The formulations were characterized in vitro and five formulations with the most promising profiles were selected for further evaluation.

Non-coated drug layered sugar cores (SYN-004) of size greater than 0.8 mm were coated using a fluid bed Mini-Coater/Drier (Caleva), equipped with a top-spray nozzle and an anti-static unit. The coating conditions used are listed in TABLE 9.

TABLE 9

Parameters used for film coating of drug layered sugar cores (SYN-004)

| Batch size | ~5 g | | |
|---|---|---|---|
| Coating solution | EUDIRAGIT FS 30 D | EUDRAGIT S100 | Duocoat inner layer |
| Fan speed (m/s) | 7.0 | 7.5 | 7.0 |
| Temperature (° C.) | 40 | 35 | 40 |
| Agitator (Hz) | 10.7 | 13.7 | 10.7 |
| Nozzle air pressure bar | 0.65 | 0.5 | 0.6 |
| Pump (%) | 12 | 30 | 12 |
| Drying Time (mm) | | 5 mins | |
| Curing Time at 40° C. (h) | 1 | 1 | 1 |

To improve the resistance of formulations during transition through the upper GI tract, the coated pellets were filled into capsules and the capsules were film coated with the enteric polymer, EUDRAGIT® FS 30 D. Gelatin and delayed release (DR) capsules of size 4 were filled manually with 15 or 10 mg equivalent of enzyme per capsule. After filling, capsules were band-sealed using an ethanolic solution of HPMC and post drying of the banding region. Then the capsules were film coated. Capsule film coating was performed on the same coater and the coating conditions used are listed in TABLE 10.

TABLE 10

Coating parameters used for capsules

| Batch size | ~40 capsules |
|---|---|
| Coating solution | EUDRAGIT FS 30 D |
| Fan speed (m/s) | 9.0 |
| Temperature (° C.) | 40 |
| Agitator (Hz) | 13.0 |
| Nozzle air pressure (bar) | 0.5 |
| Pump (%) | 18 |
| Drying Time (min) | 3-5 mins depending on coating time |
| Curing Time at 40° C. (h) | 1 |

The coating solutions were prepared as follows. The EUDRAGIT® FS 30 D aqueous dispersion was prepared following the manufacturer's instructions but without an anti-tacking agent. The EUDRAGIT® FS 30 D coating solution was composed of 49.89 g $H_2O$, 0.65 g of Triethyl citrate, and 43.01 g of the FS 30 D polymer. The EUDRAGIT® S100 organic dispersion was dissolved in 2-propanol:water (20:1; 85.71 g 2-propanol and 4.29 g $H_2O$) followed by the addition of triethyl citrate (10% w/w, 0.625 g) and 6.25 g of the S100 polymer. An anti-tacking agent was not used. The Duocoat inner layer solution was prepared by dissolving $K_2HPO_4$ and HPMC 603 in water and pH was adjusted to 10.5. The list of all coatings performed can be found in TABLE 11 below.

TABLE 11

Weight gains of coating applied as part of the characterization performed on pellets and size 4 gelatin/DR capsules.

| Trial Formulations | | % dry polymer weight gain | | | |
|---|---|---|---|---|---|
| Formulation code | Components | EUDRAGIT FS 30 D | EUDRAGIT S100 | Duocoat FS 30 D | Duocoat S100 |
| 1 | | 20% | — | — | — |
| 2 | | — | — | 20% | — |
| 3 | | — | — | 25% | — |
| 4 | | — | 30% | — | — |
| 5 | | — | 40% | — | — |
| 6 | | — | — | — | 20% |
| 7 | | — | — | — | 30% |
| 8 | | — | — | — | 40% |
| 10 | Gelatin Capsule Pellets | 5.5 mg/cm² 20% | — | — | — |
| 11 | DRcap Pellets | 5.5 mg/cm² 20% | — | — | — |

In vitro dissolution testing on coated sugar cores and capsules

The in vitro release kinetics of the coated cores was evaluated using 15 mL of dissolution medium and the equivalent in cores to 15 mg of enzyme per vial. Three different media were used to simulate pH conditions likely to be found in different parts of the GI tract; a hydrochloric acid solution (0.1M) with a pH of 1.1 was used to simulate the pH of the gastric fluids under fasted conditions and phosphate buffers with pH values of 5.5 and 7.1 mimicked the conditions in the proximal and distal regions of the intestines, respectively. The pH 5.5 buffer was composed of 0.1M HCL and 0.3M $K_2HPO_4$ 1:1 mixture with a pH adjustment to pH 5.5. The pH 7.1 buffer was 0.1M HCl and 0.3M $K_2HPO_4$ 1:1 mixture with a pH adjustment to pH 7.1. The percentage of beta-lactamase released at each time point was determined by 0.2 pm filtration followed by $A_{280}$-$A_{320}$ in UV (10 mm cuvette). The FS 30 D-coated pellets (Formulation 1, TABLE 11) were exposed to 0.1M HCl for 15 hours and no release was detected by UV and the dissolution media was clear; When exposed to pH5.5, no release was detected for 4 hours and 2% of beta-lactamase released after 20 hours. The coated pellets were exposed to pH7.1 and the result is shown in TABLE 12.

TABLE 12

Dissolution profile of EUDRAGIT FS 30 D coated pellets (Formulation 1) in pH 7.1 media (n = 1)

| Time | 20 min | 40 min | 1 h | 1.5 h | 2 h | 3 h | 4 h |
|---|---|---|---|---|---|---|---|
| % Release | 1% | 9% | 20% | 30% | 45% | 94% | 102% |

These results showed that EUDRAGIT® FS 30 D coated pellets at a coating thickness of 20% dry polymer weight gain are resistant to both acidic and mild acidic in vitro conditions.

The next formulations tested were composed of layered pellets were coated with an inner layer of hypromellose (HPMC 603) containing $KH_2PO_4$, at 5% of polymer weight gain and an outer layer of (EUDRAGIT® FS 30 D) at 20% and 25% of dry polymer weight gain (Formulation 2 and 3, respectively, TABLE 11). Formulation 2 was exposed to 0.1M HCl and no release was detected for 4 hours, but 2% of beta-lactamase released after 15 hours. When Formulation 2 was exposed to pH 5.5 the pellets were leaky with beta-lactamase released at all time points and over 50% released after 15 hours at pH 5.5 (TABLE 13). When tested at pH 7.1, Formulation 2 showed release at 20 minutes and complete release by 4 hours (TABLE 14).

TABLE 13

Dissolution profile of Duocoat pellets (Formulation 2) in pH5.5 media (n = 1)

| Time | 1 h | 2 h | 3 h | 4 h | 15 h |
|---|---|---|---|---|---|
| % Release | 0.9% | 1.1% | 2.2% | 3.6% | 52% |

TABLE 14

Dissolution profile of Duocoat pellets (Formulation 2) in pH 7.1 media (n = 1)

| Time | 20 min | 40 min | 1 h | 1.5 h | 2 h | 3 h | 4 h |
|---|---|---|---|---|---|---|---|
| % Release | 3% | 21% | 32% | 56% | 78% | 99% | 105% |

Testing of Formulation 3 at pH 5.5 media showed that this thicker coating (25%, TABLE 11) did prevent early release and displayed a similar release profile for the first 3 hours as Formulation 2 (TABLE 13). In all dissolution studies, pellets with 20% of FS 30 D (both single coat and Duocoat) were seen to swell intensively overtime regardless of pH (FIG. 21). This swelling may be may be responsible for the ingress of small amounts of buffer into the inner layer causing this to start dissolving and accelerating the dissolution of the outer layer even at lower pH values.

Formulation 4 (TABLE 11) pellets were coated with organic solutions of EUDRAGIT® S100 at 30% of dry polymer weight gain. The in vitro release results showed that the coated pellets started releasing the enzyme after 2 hours at pH5.5. Therefore, coating thickness was increased to 40% of dry polymer weight gain (Formulation 5). The coated pellets were exposed to 0.1M HCl and pH 5.5 media, no release was detected for both media for the first 2 hours. The coated pellets were exposed to pH7.1 (TABLE 15). Over 10% of the beta-lactamase was released by 20 minutes at pH 7.1 with complete release occurring by 1.5 hours. These data demonstrate that the S100 coated pellets are leakier than FS 30 D pellets. However, the 40% S100 coating was acid resistant and resistant to pH 5.5 for at least 2 hours. Once the pellets reach pH 7.1 in the lower GI tract, the beta-lactamase would release fully after approximately 1.5 hours.

TABLE 15

Dissolution profile of 40% dry polymer weight gain of EUDRAGIT S100 coated pellets (Formulation 5) in pH7.1 media (n = 2)

| Time | 20 min | 40 min | 1 h | 1.5 h |
|---|---|---|---|---|
| % Release | 11% | 40% | 72% | 99% |

Formulation 6 pellets, coated with inner layer (Hypromellose containing $KH_2PO_4$) at 5% of polymer weight gain and outer layer (EUDRAGIT® S100) at 20% of dry polymer weight gain (TABLE 11) were evaluated and demonstrated dissolution immediately. Formulations 7 and 8 (TABLE 11), where the outer layer was coated to 30% and 40% polymer weight gain, were then evaluated. After 2 hours of exposure, Formulation 7 had approximately 2% release in pH5.5 and 1% in 0.1M HCl, which suggested that 30% coating thickness was not sufficient to prevent early release. With higher thickness of coating, Formulation 8 started to release only after 3 hours in pH 5.5, which suggested that higher thickness offered better protection. However, comparing with Formulation 5 (40% of S100 single coating, see TABLE 11), Duocoat did not offer faster release in pH 7.1 media (TABLE 16). Therefore, Duocoat S100 coating on pellets was not chosen for formulations.

TABLE 16

Dissolution profile of 40% dry polymer weight gain of EUDRAGIT S100 Duocoat pellets (Formulation 8) in pH7.1 media (n = 2)

| Time | 20 min | 40 min | 1 h | 1.5 h |
|---|---|---|---|---|
| % Release | 4% | 20% | 52% | 84% |

To prepare Formulation 10 (TABLE 11), coated pellets (Formulation 1: 20% of FS 30 D) were filled into size 4 gelatin capsules. Capsules were filled with the equivalent to 15 mg of beta-lactamase per capsule. The capsules were coated with EUDRAGIT® FS 30 D at 5.5 mg/cm² and tested for their in vitro dissolution kinetics; the results are shown in FIG. 22. No release was found for the first 2 hours in acid and the following 2 hours in pH5.5; after transferring the capsule into pH7.1, full release was achieved within 4 hours. This formulation has also been exposed to pH5.5 media for more than 60 hours and no release was detected.

Figure 23:
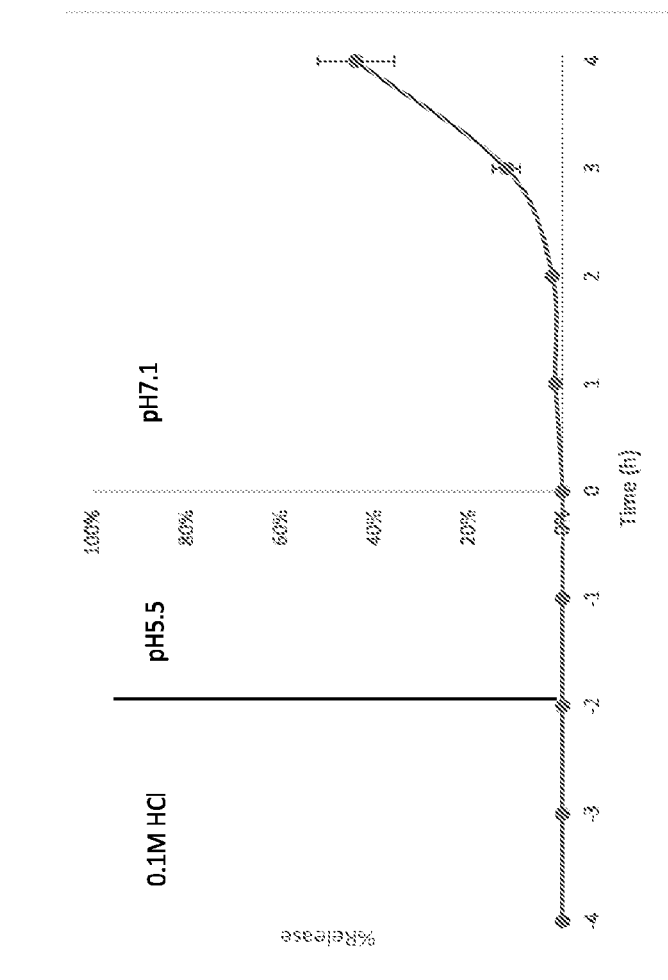
FIG. 23 shows a dissolution profile of Formulation 11: FS 30 D DR capsule (FS 30 D pellets).

To prepare Formulation 11 (TABLE 11), size 4 DR capsules were filled with equivalent to 15 mg beta-lactamase of coated sugar cores (Formulation 1: 20% FS 30 D) and were coated with EUDRAGIT® FS 30 D at a polymer weigh gain of 5.5 mg/cm². The in vitro dissolution results shown in FIG. 23 confirmed that no release could be detected after 2 hours of exposure to pH 1.6 followed by 2 hours in pH 5.5. After transferring the capsules into a phosphate buffer at pH 7.1, a lag time of 2 hours was observed due to slow release of the capsule shell. A slow release of enzyme was noted over 4 hours with only about 40% of enzyme released after 4 hours.

Figure 24:
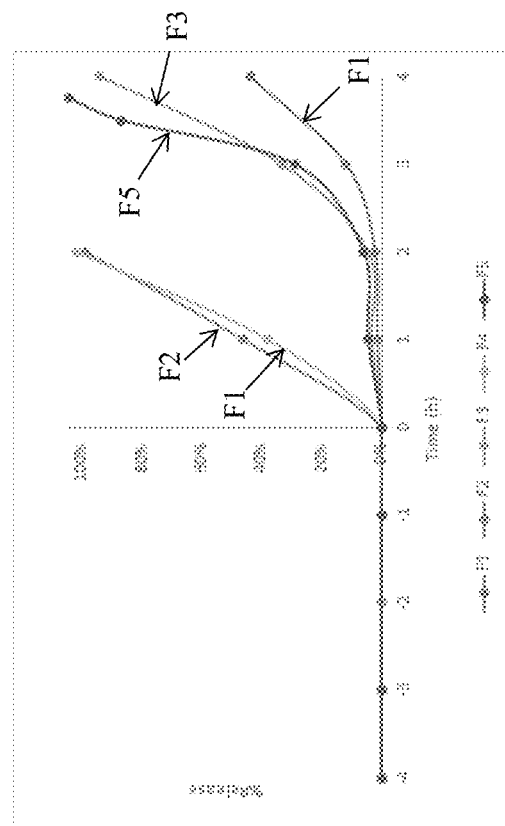
FIG. 24 shows a dissolution profile of the final five formulations.

The five formulations that displayed the most promising dissolution profiles are displayed in FIG. 31. The composition of these formulations are displayed in TABLE 18. These 5 formulations were tested in dissolution studies. For these studies, each size 4 capsule was filled with equivalent of 10 mg of enzyme. The in vitro dissolution results obtained with these formulations are depicted in FIG. 24. All five formulations were able to prevent the enzyme from releasing in the first 2 hours in acid and the following 2 hours in pH 5.5 media. F2 and F4 had the same coating on gelatin capsules therefore both of them started releasing rapidly once exposed to pH7.1. There was not much difference between both formulations regarding the profile in pH7.1, which suggested that with the same coating level of FS 30 D and S100 on pellets, FS 30 D could offer a better protection than S100. All three DR capsule formulations (F1, F3 and F5) had an expected lag time of approximately 2 hours.

TABLE 18

Compositions of P3A (SYN-004) Delayed-Release Pellets in Enteric-Coated Capsules

| Component | F1 | F2 | F3 | F4 | F5 |
|---|---|---|---|---|---|
| Layered pellets | | | | | |
| Sucrose sphere | | | 19.50 mg | | |
| Hydroxy-propylcellulose | | | 29.30 mg | | |
| P3A | | | 13.20 mg | | |
| Buffer Salts | | | 1.3 mg | | |
| Subtotal | | | 63.3 mg | | |

TABLE 18-continued

Compositions of P3A (SYN-004) Delayed-Release
Pellets in Enteric-Coated Capsules

| Component | F1 | F2 | F3 | F4 | F5 |
|---|---|---|---|---|---|
| Pellets coating | 13.3 mg | 13.3 mg | 27.9 mg | 27.9 mg | 18.6 mg |
| Subtotal | 76.6 mg | 76.6 mg | 91.2 mg | 91.2 mg | 81.9 mg |
| Size 4 Gelatin capsule | — | 42.0 mg | — | 42.0 mg | — |
| Size 4 DRcap | 43.1 mg | — | 43.1 mg | — | 43.1 mg |
| Capsule coating | | | 13.6 mg | | |
| Subtotal | 56.7 mg | 55.6 mg | 56.7 mg | 55.6 mg | 56.7 mg |
| Total | 133.3 mg | 132.2 mg | 147.9 mg | 146.8 mg | 138.6 mg |

Example 6. Evaluation of Formulation 2 in Dogs Treated with Oral Amoxicillin

Formulation 2 (FIG. 31) was chosen for evaluation in dogs. A two arm pharmacokinetics (PK) study was performed in three non-naïve male beagle dogs (age 2 years, approximately 12 kg). Animals were fasted overnight prior to the day of dosing in each arm. In Arm 1, the dogs were administered one dose of an amoxicillin suspension (amoxicillin powder, Sandoz, Lot FW1707, reconstituted in apple juice to 400 mg/5 mL) via oral gavage at 80 mg/kg. Animals were returned to their cages post-dose and fed 1.5 hrs after amoxicillin dosing. In Arm 2, dogs were administered an amoxicillin suspension (80 mg/kg, prepared as in Arm 1) via oral gavage. Immediately after the oral amoxicillin was dosed, the animals received one size 4 capsule of Formulation 2 (FIG. 31) containing 10 mg of SYN-004. The capsules were not chewed and were swallowed whole. Capsules were dosed by hand by placing the capsule in the back of the dog's mouth and followed by 6 mL of Mott's 100% apple juice in a syringe. Animals were returned to their cages post-dose and fed 1.5 hrs after amoxicillin dosing. There was a seven day washout period between the two arms. In both arms of the study, blood (approximately 2 mL) was collected for serum PK analysis at pre-dose, and 30 minutes, 1, 2, 3, 4, 6, 8, and 10 hrs post-dose. Serum was collected and immediately frozen at −80° C. Feed was ad-libitum throughout both arms, except during dosing, which was done fasted as described. Clinical observations did not disclose treatment related abnormalities. Animals were returned to the colony following the last blood collection.

Figure 25:
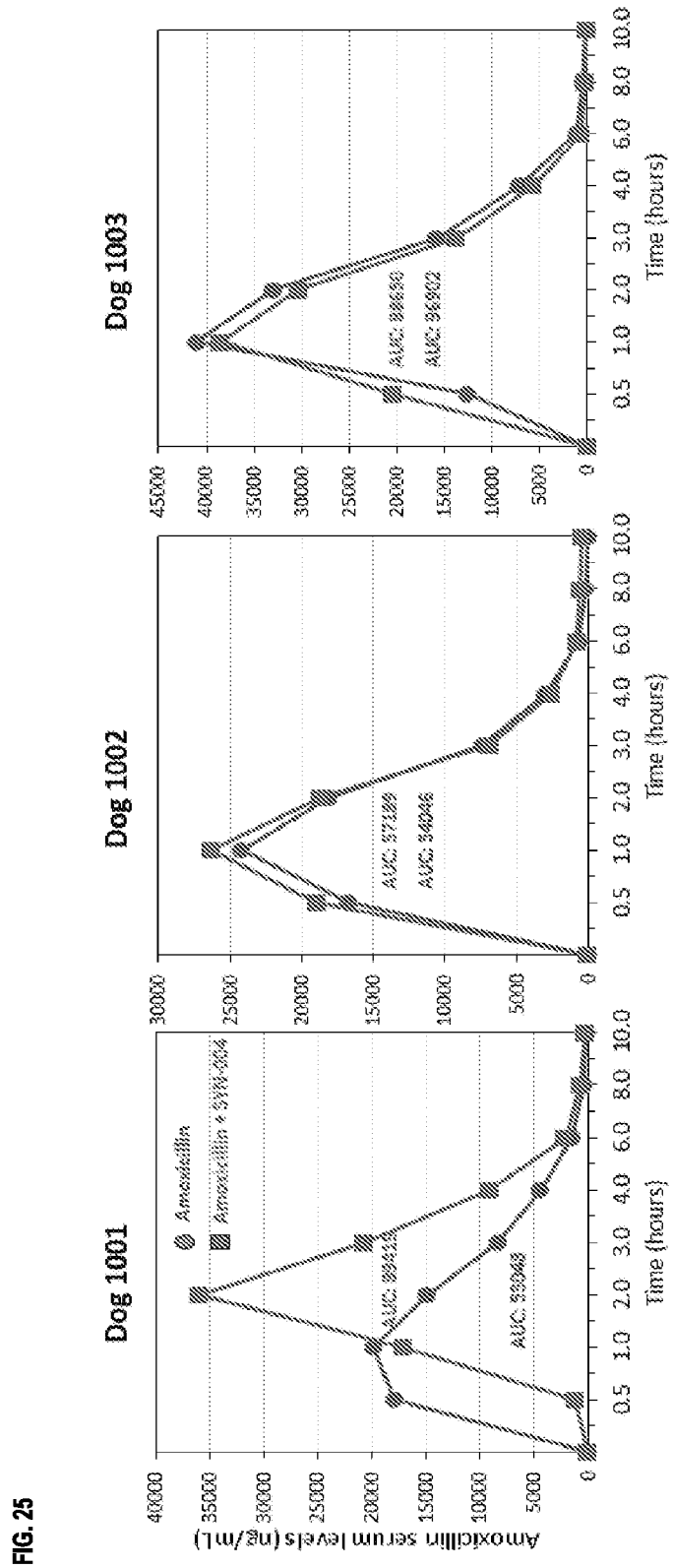
FIG. 25 shows the amoxicillin serum levels in dogs with amoxicillin alone (study Arm 1) and with amoxicillin+SYN-004 (study Arm 2). Each of the three panels represents the three animals in the study. Each panel contains two graphs, serum amoxicillin levels in Arm 1 and Arm 2. The area under the curve (AUC) was calculated for each curve and the calculated area is displayed inside each curve on the graphs.

Serum was analyzed for amoxicillin levels using a validated liquid chromatography (LC) method with tandem mass spectrometry detection (LC/MS/MS). Briefly, the serum samples were extracted using the protein precipitation extraction method and analyzed using reverse phase LC. Amoxicillin and amoxicillin-$d_4$ (internal standard) were detected using tandem MS. The study was performed using Applied Biosystems Triple Quad API 500 LC/MS/MS system with Turbo ion spray interfaces. The data were acquired and analyzed by Applied Biosystems "Analyst" software, version 1.5. The lower limit of quantitation (LLOQ) for amoxicillin was 101.723 ng/mL. The upper limit of quantitation (ULOQ) for amoxicillin was 20344.678 ng/mL. A calibration curve consisting of two control blanks, two zero standards and ten non-zero standards, prepared in naïve dog serum, covering a range of 101.723 to 20344.678 ng/mL, were run with each sample batch. Amoxicillin levels were similar for each animal in Arm 1 and Arm 2 of the study (TABLE 19). The amoxicillin serum levels in Arm 1 and Arm 2 for each dog were plotted separately and the area under the curves was calculated (FIG. 25). The area under the curve for each animal was similar in Arm 1 and Arm 2 of the study. These data demonstrate that the delayed release SYN-004 formulation 2 (FIG. 31) did not interfere with amoxicillin systemic absorption and indicate that this SYN-004 formulation 2 was not released prematurely prior to amoxicillin absorption in the upper small intestine in the dog. Therefore, the strategy to reduce the potential for premature release, release in the small intestine prior to absorption of orally-delivered amoxicillin, by using FS 30 D-coated SYN-004 layered sucrose pellets incorporated inside FS 30 D-coated capsule, or the "nested" strategy, was successful as indicated by the similar amoxicillin blood levels in each dog with and without SYN-004.

TABLE 19

Amoxicillin levels in dog serum

| | | Time Points (hr) | | | |
|---|---|---|---|---|---|
| Animal | Arm | 0.00 | 0.50 | 1.00 | 2.00 |
| 1001 | 1 | BLQ | 17908.396 | 19859.916 | 14863.466 |
| | 2 | BLQ | 1210.311 | 17169.626 | 35935.251 |
| 1002 | 1 | BLQ | 16720.439 | 24195.148 | 18108.596 |
| | 2 | BLQ | 18996.600 | 26311.547 | 18700.192 |
| 1003 | 1 | BLQ | 12592.818 | 41086.716 | 32941.651 |
| | 2 | BLQ | 20368.905 | 38503.086 | 30317.167 |

| | | Time Points (hr) | | | | |
|---|---|---|---|---|---|---|
| Animal | Arm | 3.00 | 4.00 | 6.00 | 8.00 | 10.00 |
| 1001 | 1 | 8344.240 | 4381.382 | 1471.826 | 384.786 | 183.251 |
| | 2 | 20692.988 | 9124.105 | 21200.876 | 732.639 | 257.544 |
| 1002 | 1 | 7397.008 | 2965.079 | 666.218 | 217.194 | BLQ |
| | 2 | 6908.640 | 2532.246 | 847.638 | 568.531 | 466.367 |
| 1003 | 1 | 15781.778 | 7146.601 | 1191.117 | 456.767 | 199.116 |
| | 2 | 13705.840 | 5648.301 | 693.048 | 331.914 | 134.994 |

Concentration unit: ng/mL
BLQ: Below lower limit of quantitation

Figure 26:
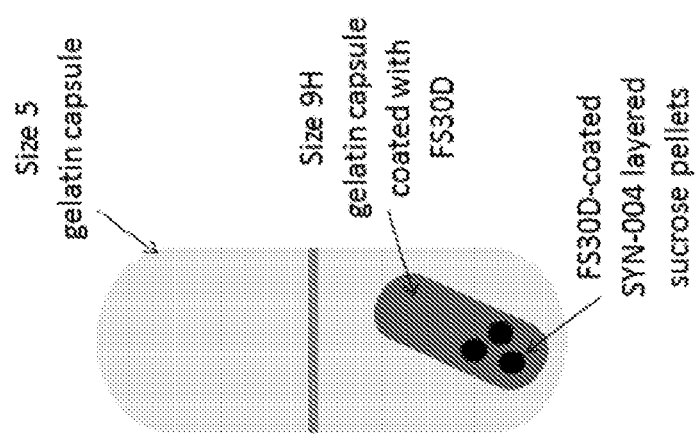
FIG. 26 shows an example of the modified nested strategy for the SYN-004 formulation. FS 30 D-coated SYN-004 layered sucrose pellets were put into small gelatin capsules that were coated with FS 30 D, and the small capsule was put into a larger gelatin capsule for ease of delivery.

Example 7. Evaluation of a Derivative of the SYN-004 Nested Formulation in Normal Piglets Formulation 2 (FIG. 31) capsules consisting of FS 30 D-coated SYN-004 pellets within FS 30 D-coated capsules were prepared for testing in normal piglets. For this formulation, size 9H gelatin capsules (small capsules, 2.7 mm diameter, 5 mm length) were filled with 3 pellets of FS 30 D-coated SYN-004 sucrose cores, then coated with FS 30 D. The coated 9H capsule containing the SYN-004 pellets was then inserted into a size 5 gelatin capsule for ease of delivery to the pigs (FIG. 26). Each FS 30 D-coated pellet of SYN-004 contained 165 mg of SYN-004. Therefore, the total SYN-004 dose was 0.5 mg/size 5 gelatin capsule. The anticipated advantage of this nested strategy using the small 9H capsules is that the gelatin capsule will dissolve in the stomach, releasing the small FS 30 D-coated 9H capsule that is protected from stomach acid and is small enough to pass through the gastric pylorus without the need for stomach emptying.

Figure 27:
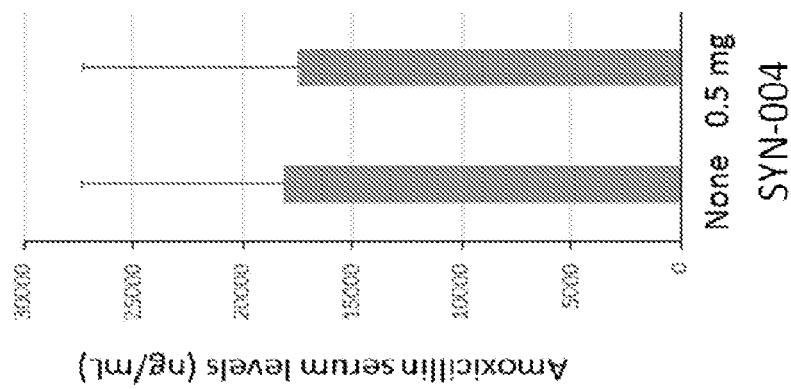
FIG. 27 shows the amoxicillin serum levels in pigs treated with amoxicillin alone (None) or amoxicillin+SYN-004 (0.5 mg). Data are plotted as mean and standard deviation.

A study was performed using normal piglets to test this modified nested formulation of SYN-004. Two cohorts of pigs each, two month old Yorkshire piglets, approximately 20 kg each, were used for this study. Pigs received oral amoxicillin (40 mg/kg) alone or with one capsule of the SYN-004 modified nested formulation. Pigs were bled three hours later, serum collected, and shipped to the analytical lab for measurement of amoxicillin levels in the pig serum using a validated liquid chromatography method with MS/MS detection as described in Example 4. Amoxicillin levels were similar in animals treated with amoxicillin alone and with amoxicillin plus the SYN-004 (FIG. 27; TABLE 20). These data demonstrate that the modified nested formulation of SYN-004 did not interfere with the intestinal absorption of orally-delivered amoxicillin in the piglets because the amoxicillin serum levels in animals with or without SYN-004 were not significantly different. The results indicate that the modified nested formulation of SYN-004 prevented premature release of SYN-004.

TABLE 20

Amoxicillin levels in pig serum

| Cohort | Treatment | Animal | Amoxicillin Serum Levels (ng/mL) | | |
|---|---|---|---|---|---|
| 1 | Amoxicillin | 1 | 29647 | Mean | Standard |
|   |             | 2 | 6498  | 181933 | Deviation |
|   |             | 3 | 25130 |       | 9199 |
|   |             | 4 | 14936 |       |      |
|   |             | 5 | 14757 |       |      |
| 2 | Amoxicillin + SYN-004 | 6 | 3292  | 17494 | 9786 |
|   |             | 7 | 29060 |       |      |
|   |             | 8 | 14509 |       |      |
|   |             | 9 | 16922 |       |      |
|   |             | 10 | 23688 |       |      |

Figure 28:
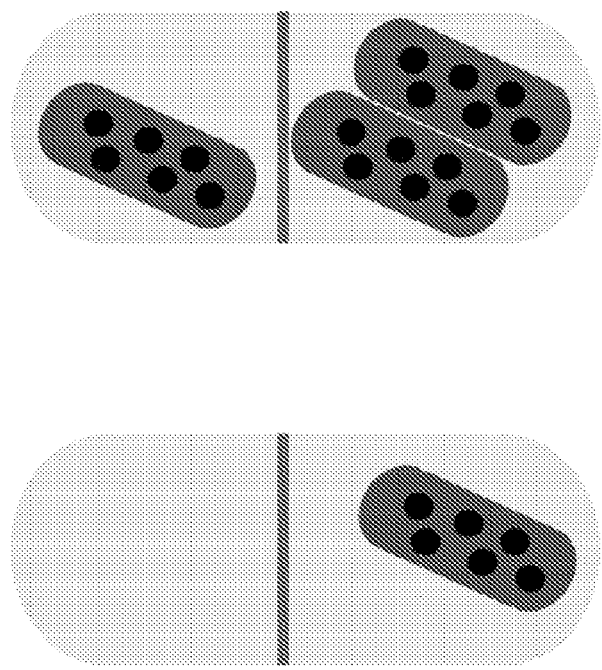
FIG. 28 shows an example of the modified nested strategy for SYN-004 formulations with different SYN-004 doses. Coated SYN-004 layered sucrose pellets were put into small gelatin capsules that were coated and the small capsule or capsules were put into a larger gelatin capsule for ease of delivery.

Example 8. Evaluation of a Derivative of the SYN-004 Nested Formulation in Normal Piglets Treated with Augmentin Formulation 2 (FIG. 31) capsules consisting of FS 30 D-coated SYN-004 pellets within FS 30 D-coated capsules were prepared for testing in normal piglets in a similar way as described in Example 7. Size 9H gelatin capsules were filled with six pellets of FS 30 D-coated SYN-004 sucrose cores and then coated with FS 30 D. Capsules with two doses of SYN-004 were prepared, a 1.0 mg dose and a 3.0 mg dose (FIG. 28). For the 1.0 mg dose, one coated 9H capsule containing six SYN-004 pellets was inserted into a size 5 gelatin capsule. For the 3.0 mg dose, three coated 9H capsules each containing six SYN-004 pellets was inserted into a size 5 gelatin capsule.

Figure 29:
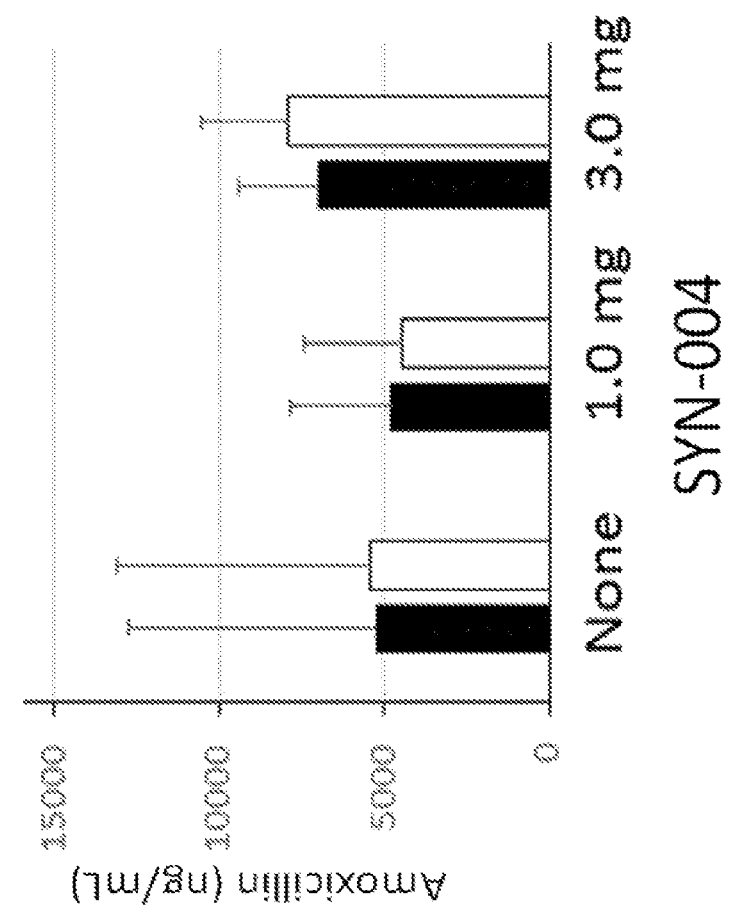
FIG. 29 shows the amoxicillin serum levels in pigs treated with Augmentin alone (None), or Augmentin+SYN-004 (1.0 mg) or Augmentin+SYN-004 (3.0 mg). The black bars represent the 1.5 hour bleed time and the white bars represent the 3.0 hour bleed time. Data are plotted as mean and standard deviation.
Figure 30:
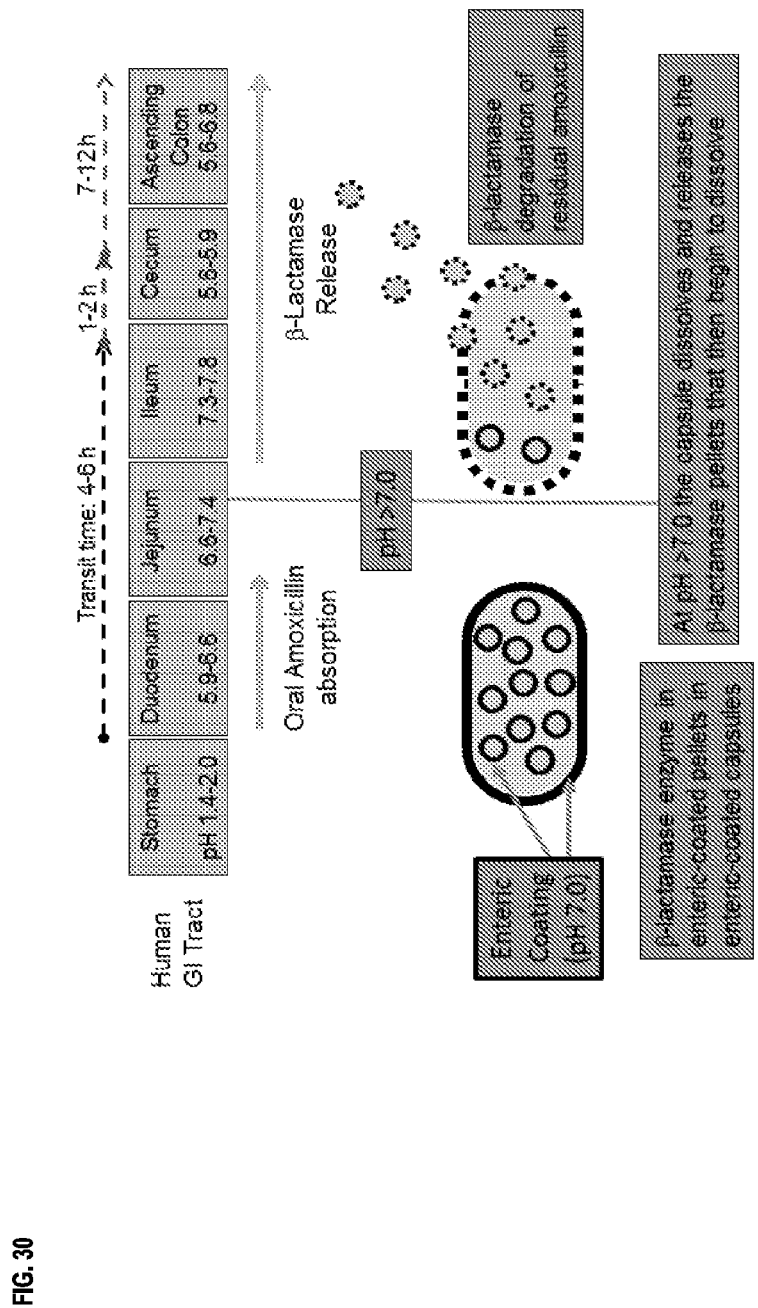
FIG. 30 shows various formulation approaches of the invention to segregate antibiotic absorption from beta lactamase release.

The higher dose formulations of SYN-004 were tested in normal piglets with oral amoxicillin/clavulanate (Augmentin; antibiotic/inhibitor combination). Three cohorts of 5 pigs each, two month old Yorkshire piglets, approximately 20 kg each, were used for this study. Pigs received oral Augmentin (40 mg/kg amoxicillin+clavulanate) alone or with one capsule of the 1.0 mg or the 3.0 mg dose of the SYN-004 modified nested formulation. Pigs were bled 1.5 and 3 hours later, serum collected, and shipped to the analytical lab for measurement of amoxicillin levels in the pig serum using a validated liquid chromatography method with MS/MS detection as described in Example 4. Amoxicillin levels were similar in animals treated with amoxicillin alone and with amoxicillin plus the SYN-004 (FIG. 29; TABLE 21). These data demonstrate that the modified nested formulation of SYN-004 at doses of 1.0 mg and 3.0 mg did not interfere with intestinal absorption of orally-delivered Augmentin in the piglets because the amoxicillin serum levels in animals with or without SYN-004 were not significantly different.

TABLE 21

Amoxicillin levels in pig serum from pigs treated with Augmentin

| | | Amoxicillin Serum Levels (ng/mL) | | | |
|---|---|---|---|---|---|
| | | 1.5 Hours | | 3.0 Hours | |
| Cohort | Treatment | Mean | Standard Deviation | Mean | Standard Deviation |
| 1 | Augmentin | 5281 | 7467 | 5467 | 7626 |
| 2 | Augmentin + 1.0 mg SYN-004 | 4818 | 3046 | 4440 | 2977 |
| 3 | Augmentin + 3.0 mg SYN-004 | 7069 | 2346 | 7943 | 2596 |

Example 9. Evaluation of SYN-004 Formulation 2 and Derivatives in a Dog Microbiome Protection Study Formulation 2 capsules were prepared in three ways with all derivatives composed of pellets made from sucrose cores covered with SYN-004 and coated with EUDRAGIT® FS 30 D or L30-D55. One derivative most similar to Formulation 2 contained the FS 30 D pellets in size 9H capsules that were coated with FS 30 D, all put into a size 5 uncoated gelatin capsule (for ease of delivery). It is anticipated that the gelatin capsule will dissolve in the stomach, releasing the small FS 30 D-coated 9H capsules that are small enough to pass through the gastric pylorus without the need for stomach emptying. Another derivative contained the FS 30 D pellets filled directly into uncoated gelatin capsules to ensure that the SYN-004 pellets will be released in the dog GI tract. The final derivative contained L30-D55-coated SYN-004 pellets filled into FS 30 D coated 9H capsules which were then put into a size 4 uncoated gelatin capsule. All formulations contained approximately 10 mg of SYN-004. The three formulations are described in TABLE 22.

TABLE 22

SYN-004 Formulations for Dog Microbiome Protection Study

| Formulation | Pellets | Capsule | Package |
|---|---|---|---|
| 1 | EUDRAGIT FS 30 D coated (20% polymer weight gain) SYN-004 cores | EUDRAGIT FS 30 D coated (6.3 mg/cm$^2$ polymer weight gain) Size 9 gelatine capsule | 12 pellets per size 9 capsule 5 size 9 capsules per dose (size 0 gelatin white capsule) Dosage: 9.4 mg SYN-004 |

TABLE 22-continued

SYN-004 Formulations for Dog Microbiome Protection Study

| Formulation | Pellets | Capsule | Package |
|---|---|---|---|
| 2 | EUDRAGIT FS 30 D coated (20% polymer weight gain) SYN-004 cores | Size 5 gelatine capsule | Pellets in size 5 transparent capsules Dosage: 10 mg SYN-004 |
| 3 | EUDRAGIT L30-D55 coated SYN-004 cores | EUDRAGIT FS 30 D coated (6.3 mg/cm$^2$ polymer weight gain) Size 9 h gelatine capsule | 8 pellets per size 9 h capsule 8 size 9 h capsules per dose (size 0 gelatin yellow capsule) Dosage: 10 mg SYN-004 |

The in vitro dissolution of the 3 derivatives of Formulation 2 will be evaluated as described in Example 5 and FIG. 24. The 3 derivatives of Formulation 2 will then be evaluated in dogs. For the dog study, naïve beagles (n=20) that have never been exposed to antibiotics will receive amoxicillin (40-80 mg/kg, TID, PO) with or without the SYN-004 formulations, 5 animals per cohort. Pretreatment serum samples will be obtained from all dogs prior to study initiation. SYN-004 will be delivered after dosing with amoxicillin (10 mg, TID, PO). The animals will be dosed with amoxicillin and SYN-004 for 5 days, with the last dose on the morning of day 6 (total of 16 doses of amoxicillin+/−SYN-004). Dogs will be bled after the first dose and on day 6, at seven timepoints, 0.5, 1, 2, 3, 4, 6, and 8 hrs. Blood will be processed to serum. Fecal samples will be collected prior to treatment and at day 6. Serum will be used to quantify the amoxicillin levels and fecal samples will be processed to DNA and subjected to whole genome shotgun sequencing analyses to assess the fecal microbiome. The expected results of this study are that all SYN-004 derivatives, or at least one derivative, will not change systemic amoxicillin levels and will protect the microbiome from the damage caused by amoxicillin exposure.

Example 10. Evaluation of SYN-004 Formulations in a Pig Microbiome Protection Study Formulations of SYN-004 based on those that did not interfere with amoxicillin absorption in the pigs (see examples 7 and 8) will be prepared and tested in pigs. The formulations are anticipated to contain pellets made from sucrose cores covered with SYN-004 and coated with EUDRAGIT® FS 30 D or L30-D55. The pellets are contained in size 9 or size 9H gelatin capsules coated with FS 30 D. Depending on the SYN-004 dose used, the coated size 9 or 9H capsules will be put into a size 5 or larger uncoated gelatin capsule (for ease of delivery). The SYN-004 formulations will contain between 0.5 mg up to 10 mg of SYN-004.

The in vitro dissolution of the SYN-004 formulations will be evaluated as described in Example 5 and FIG. 24. The SYN-004 formulations will then be evaluated in pigs. For the pig study, normal piglets will receive oral amoxicillin or oral amoxicillin/clavulanate (Augmentin; antibiotic/inhibitor combination). Each SYN-004 formulation will be tested in a cohort of pigs (n=5), and one cohort (n=5) will receive amoxicillin or Augmentin alone. Pigs will receive antibiotic+/−SYN-004 three times a day at 8 hour intervals for a total of 16 doses of antibiotic+/−SYN-004. Pigs will be fed 1.5 hours after each antibiotic+/−SYN-004 administration. Pretreatment serum samples will be obtained from all dogs prior to study initiation. Pigs will be bled after the first dose of antibiotic+/−SYN-004, and after the last dose of antibiotic+/−SYN-004. For each bleeding, animal will be bled 1.5, 3.0, and 4.5 hours after antibiotic+/−SYN-004 administration. Blood will be processed to serum and amoxicillin levels in the serum will be quantified using a validated liquid chromatography method with MS/MS detection as described in Example 4. Feces will be collected prior to antibiotic+/−SYN-004 administration and after the last dose of antibiotic+/−SYN-004. Feces will be processed to DNA and subjected to whole genome shotgun sequencing analyses to assess the fecal microbiome. The expected results of this study are that all SYN-004 derivatives, or at least one derivative, will not change systemic amoxicillin levels and will protect the microbiome from the damage caused by amoxicillin exposure.

Example 11. GI Tract Localization of Beta-Lactamase Release

These studies are designed to identify preferred sites of beta-lactamase delivery to the GI tract to achieve efficient antibiotic absorption and microbiome protection.

Beta-lactamase SYN-004 a/k/a P3A (resuspended in PBS or other buffer, or any of the formulations of SYN-004) is delivered directly to various regions of the intestinal tract of dogs via intubation or a fistula in the intestine. Animals receive oral antibiotic, such as amoxicillin, or amoxicillin/clavulanic acid (Augmentin), and P3A via direct delivery to the small intestine including the duodenum, jejunum, ileum, and/or cecum. Plasma levels of the antibiotic are measured and the diversity of the microbiome is assessed by 16S sequence analysis of microbes in the stool, as an assessment of antibiotic degradation, and microbiome protection. Cohorts include antibiotic alone, antibiotic/inhibitor alone, antibiotic/inhibitor+P3A, and antibiotic+P3A, delivered to the indicated areas of the small intestine.

To perform this study, fistulas are implanted in groups of dogs (n=3-5 per cohort) at the indicated locations in the small intestine including, the duodenum, jejunum, ileum, cecum, and ascending colon (TABLE 20). The dogs receive a dosage of oral antibiotic, such as amoxicillin or an antibiotic/inhibitor combination, such as amoxicillin/clavulanic acid (Augmentin) as a single dose. P3A is delivered as an oral pill (using the current SYN-004 formulation) or dissolved in PBS buffer via direct infusion into the fistula and delivered within 30 minutes after the oral antibiotic. Plasma samples are drawn from the dogs at various time points to measure antibiotic levels in the blood as a measure of antibiotic absorption. Fecal samples are collected from the animals to measure the level of excreted antibiotics and to assess the intestinal microbiome using 16S sequence analyses, as an additional assessment of antibiotic degradation.

TABLE 23

Treatment of fistulated dogs with oral antibiotic/inhibitor or oral antibiotic and SYN-004

| Cohort | Oral Antibiotic | P3A |
|---|---|---|
| 1 | None | None |
| 2 | Antibiotic | None |
| 3 | Antibiotic/inhibitor | None |
| 4 | None | P3A-current oral formulation |
| 5 | Antibiotic and/or antibiotic/inhibitor combo | P3A-current oral formulation |
| 6 | Antibiotic and/or antibiotic/inhibitor combo | P3A-via fistula to duodenum |
| 7 | Antibiotic and/or antibiotic/inhibitor combo | P3A-via fistula to jejunum |
| 8 | Antibiotic and/or antibiotic/inhibitor combo | P3A-via fistula to ileum |
| 9 | Antibiotic and/or antibiotic/inhibitor combo | P3A-via fistula to cecum |
| 10 | Antibiotic and/or antibiotic/inhibitor combo | P3A-via fistula to ascending colon |

The results allow the demonstration that delivery of P3A to the small intestine results in protection of the microbiome and does not affect antibiotic plasma levels. The study allows the identification of preferred sites of beta-lactamase delivery to the small intestine or colon to achieve microbiome protection. Related studies with different antibiotics and/or antibiotic/inhibitor combinations may be undertaken to specify key locations in the intestinal tract.

Example 12. Evaluation of P3A as a Prophylactic to Prevent C. difficile Disease (CDI) Following Oral Antibiotic Treatment in Hamsters These studies evaluate the efficacy of SYN-004 (current enteric formulation or modified-release formulations of P3A, e.g. as described herein) in the prevention of CDI in the hamster disease model.

SYN-004 or modified-release formulations of P3A are tested in rodent models of CDI. Rodent models include the Syrian Golden hamster (Mesocricetus auratus) C. difficile model (Sambol and Tang, 2001; J. Infect. Disease 183: 1760). The hamster model has been referred to as "the gold standard" small animal model for the evaluation of the efficacy of a variety of prophylactic and therapeutic interventions against CDI. CDI is induced in the hamsters using the following protocol. Male Golden Syrian hamsters, purchased from Harlan (Indianapolis, Ind.) are pretreated 5 days or 24 hours prior to infection with a single subcutaneous injection of clindamycin at 10 or 30 mg/kg to deplete the animal's microbiome and predispose them to C. difficile infection. As ampicillin is also a risk for C. difficile infection (Freeman and Wilcox, 1999; Microbes Infect. 1:377), oral Augmentin, sultamicillin, ampicillin and/or amoxicillin is used in place of clindamycin to predispose the animals to C. difficile infection. Plasma is collected at various times prior to and after antibiotic delivery to measure antibiotic blood levels. On the day of infection, animals are inoculated by oral gavage with $10^6$ C. difficile (ATCC 43255) vegetative cells per hamster. The C. difficile inoculum is prepared by growing the bacteria in Difco reinforced clostridial medium with 1% Oxyrase for 24 hrs under anaerobic conditions. The optical density at 600 nm is adjusted to 1.5 and then diluted 1:10. The hamsters are given 0.75 ml of this suspension orally via gavage. An aliquot of the inoculum is then serially diluted, plated on brucella agar supplemented with hemin and vitamin $K_1$ (Remel, Lenexa, Kans.), and incubated anaerobically for 48 hrs in an airtight container (Pack-Anaero MGC) to determine the infection titer. Animals are observed twice daily during the first 24 hrs post-infection and then every 2 hrs for the following 24 hrs during the acute phase of the disease, followed by twice daily for the remainder of the study. Signs of CDI include signs of mortality and morbidity, presence of diarrhea as indicated by a wet tail, and overall appearance including activity, general response to handling, touch, or ruffled fur. Body weights are monitored every 2 to 3 days.

To evaluate the prophylactic potential of SYN-004 or modified-release formulations of P3A, it is administered orally beginning at the time of oral antibiotic administration, 1 day prior to C. difficile infection, and continued for the duration of the studies, up to 28 days. Disease is compared in animals that receive clindamycin (as the positive control) or oral antibiotic/inhibitor combinations or oral antibiotics (Oral Antibiotic). The efficacy of the P3A treatment groups are compared to control animals that receive no treatment, animals that receive the standard of care, vancomycin (20 mg/kg orally daily beginning 24 hrs after infection and continued for 5 days.. Plasma is monitored for antibiotic levels and stool DNA is subjected to sequencing to monitor the diversity of the microbiome. Efficacy evaluations include mortality and evaluation of C. difficile bacteria titers and/or C. difficile toxins A and B in cecal contents, at the time of death or at the end of the study following euthanasia. The results may show that treatment with the oral antibiotics and all or one of the P3A formulations, did not affect blood levels of the antibiotic and protected the animals from CDI, indicating that the P3A degraded the antibiotic excreted into the intestine following antibiotic absorption without affecting the initial antibiotic absorption. See TABLE 24 for the experimental design.

TABLE 24

C. difficile efficacy hamster study treatment groups

| Cohort (n = 6-10) | Antibiotic | C. diff inoculation | Treatment |
|---|---|---|---|
| 1 | none | None | none |
| 2 | Clindamycin (30 mg/kg) | + | none |
| 3 | Oral Antibiotic Dose TBD | + | none |
| 4 | Oral Antibiotic Dose TBD | + | vancomycin |
| 5 | Oral Antibiotic Dose TBD | + | SYN-004 or P3A Formulation 1 |
| 6 | Oral Antibiotic Dose TBD | + | SYN-004 or P3A Formulation 2 |

Example 13. Evaluation of P3A as a Prophylactic to Prevent C. difficile Disease (CDI) Following Oral Antibiotic Treatment in Pigs These studies evaluate the efficacy of SYN-004 (enteric formulation or modified-release formulations of P3A, e.g. as described herein) in the prevention of CDI in humanized pigs.

SYN-004 or modified-release formulations of P3A are tested in a humanized pig model of CDI. The humanized pig model is a model of the human gastrointestinal tract where the gnotobiotic pigs are reconstituted with human fecal homogenates (Zhang et al., Gut Microbes 4:193). The humanized pigs are treated with antibiotics (clindamycin, Augmentin, sultamicillin, ampicillin or amoxicillin) to disrupt their intestinal microbiome and then exposed to *C. difficile* after which they develop CDI including *C. difficile* associated diarrhea (CDAD).

To test the prophylactic potential of SYN-004 or modified-release formulations of P3A, P3A is administered one day prior to antibiotic treatment (Day −1), and maintained for the duration of the antibiotic treatment. Clindamycin is delivered 1 to 5 days prior to *C. difficile* inoculation. Oral antibiotics such as Augmentin, sultamicillin, ampicillin or amoxicillin, are delivered beginning 1 to 5 days prior to *C. difficile* inoculation, and maintained for 5-7 days. The antibiotics are used to disrupt the intestinal microbiome to predispose the animals to *C. difficile* infection. Plasma levels of antibiotics are monitored prior to antibiotic treatment, and during treatment to assess antibiotic absorption. *C. difficile* vegetative cells or spores are administered, at doses ranging from $10^6$ to $10^8$, and animals are monitored for CDI symptoms including CDAD. Animals exposed to *C. difficile* are expected to develop disease symptoms within 48 hrs of bacterial inoculation (Steele et al., 2010; J. Infect. Dis 201:428). CDI is compared in animals that receive clindamycin or oral antibiotics, such as Augmentin, sultamicillin, ampicillin or amoxicillin (Oral Antibiotic). The efficacy of the P3A treatment groups are compared to control animals that receive no treatment, animals that receive the standard of care, vancomycin (20 mg/kg orally daily beginning 24 hrs after infection and continued for 5 days. The results may show that treatment with the oral antibiotics and one or more of the oral P3A formulations, did not affect blood levels of the antibiotic and protected the animals from CDI, indicating that the P3A degraded the antibiotic excreted into the intestine following antibiotic absorption without affecting the initial antibiotic absorption. See TABLE 25 for the experimental design.

TABLE 25

SYN-004 or modified-release formulations of P3A *C. difficile* efficacy humanized pig study treatment groups

| Cohort (n = 2-3) | Antibiotic | *C. diff* inoculation | Treatment |
|---|---|---|---|
| 1 | none | None | none |
| 2 | Clindamycin (30 mg/kg) | + | none |
| 3 | Oral Antibiotic Dose TBD | + | none |
| 4 | Oral Antibiotic Dose TBD | + | vancomycin |
| 5 | Oral Antibiotic Dose TBD | + | SYN-004 or P3A Formulation 1 |
| 6 | Oral Antibiotic Dose TBD | + | SYN-004 or P3A Formulation 2 |

Example 14. Evaluation of SYN-004 and Oral Antibiotics in an Artificial Small and Large Intestine System The artificial small and large intestine system, TIM and/or TIM2 (see, e.g. Yoo, J. Y., & Chen, X. D. (2006). GIT physicochemical modeling—A Critical Review, *International Journal of Food Engineering*, 2(4), the contents of which are hereby incorporated by reference), is used to evaluate the current, enteric-coated SYN-004 formulation and/or modified-release formulations of SYN-004, e.g. as described herein, to more specifically localize the site(s) of SYN-004 release and antibiotic release within the intestinal track.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties. The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

REFERENCES

The following are hereby incorporated by reference in their entireties:

Bevan, A, Brenner, C, Fuller, R S. (1998). Quantitative assessment of enzyme specificity in vivo: $P_2$ recognition by KEx2 protease defined in a genetic system. PNAS 95:10384-10389.

Davis, S S, Hardy, J G, Fara, J W. (2014). Transit of pharmaceutical dosage forms through the small intestine. Gut 27:886-892.

DiCarlo, J E, Norville, J E, Mali, P, Rios, X, Aach, J, Church, G M. (2013). Genome engineering in *Saccharomyces cerevisiae* using CRISPR-Cas systems. Nucl. Acids Res. 41: 4333.

Edwards-Ingram, L, Gitsham, P, Burton, N, Warhurst, G, Clarke, I, Hoyle, D, Oliver, S G, Stateva, L. (2007). Genotypic and physiological characterization of *Saccharomyces boulardii*, the probiotic strain of *Saccharomyces cerevisiae*. Appl. Environ. Microbiol. 73:2458.

Flagfeldt, D B, Siewers, V, Huang, L, Nielsen, J. (2009). Characterization of chromosomal integration sites for heterologous gene expression in *Saccharomyces cerevisiae*. Yeast 26:545.

Freeman, J, Wilcox, M H. (1999). Antibiotics and *Clostridium difficile*. Microbes Infect. 1:377-384.

Garrait, G, Jarrige, J F, Blanquet-Diot, S, Alric, M. (2009). Genetically engineered yeasts as a new delivery vehicle of active compounds to the digestive tract: In vivo validation of the concept in the rat. *Metabolic Engineering* 11:148-154.

Graff, S, Chaumeil, J-C, Boy, P, Lai-Kuen, R, Charrueau, C. (2008). Influence of pH conditions on the viability of *Saccharomyces boulardii* yeast. J. Gen. Appl. Microbiol. 54:221-227.

Hatoum R, Labrie, St, Fliss, I. (2012). Antimicrobial and probiotic properties of yeasts: from fundamental to novel applications. Frontiers in Microbiology 3: 421-421.

Hou, J, Tyo, K E J, Liu, Z, Petranovic, D, Nielsen, J. (2012). Metabolic engineering of recombinant protein secretion by *Saccharomyces cerevisiae*. FEMS Yeast Res. 12:491-510.

Kelesidis, T, Pothoulakis, C. (2012). Efficacy and safety of the probiotic *Saccharomyces boulardii* for the prevention and therapy of gastrointestinal disorders. Therapeutic Advances in Gastroenterology 5:111.

Klein, S M, Elmer, G W, McFarland, L V, Surawicz, C M, Levy, R H. (1993). Recovery and elimination of the biotherapeutic agent, *Saccharomyces boulardii*, in healthy human volunteers. Pharm Res. 10:1615-1619.

Liu, F, Moreno, P, Basit, A W. (2010). A novel double-coating approach for improved pH-triggered delivery to the ileo-colonic region of the gastrointestinal tract. European J. Pharm. Biopharma. 74:311-315.

McCoullough, M J, Clemons, K V, McCusker, J H, Stevens, D A. (1998). Species identification and virulence attributes of *Saccharomyces boulardii*. J. Clin. Microbiol. 36:2613.

Sambol, S P, Tang, J K. (2001). Infection of hamsters with epidemiologically important strains of *Clostridium difficile*. J. Infect. Diseases 183:1760.

Steele, J, Feng, H, Parry, N, Txipori, S. (2010). Piglet models for acute or chronic *Clostridium difficile* illness (CDI). J. Infect. Dis. 201:428.

Varum, F J O, Hatton, G B, Freire, A C, Basit, A W. (2013). A novel coating for ileo-colonic drug targeting: Proof of concept in humans using scintigraphy. European J. Pharm. Biopharma. 84:573-577.

Yigit, H, Queenan, A M, Anderson, G J, Domenech-Sanchez, A, Biddle, J W, Steward, C D, Alberti, S, Bush, K, Tenover, F C. (2001). Novel carbapenem-hydrolyzing beta-lactamase, KPC-1, from a carbapenem-resistant strain of *Klebsiella pneumoniae*. Antimicrobial Agents and Chemotherapy 45:1151-1161.

Zhang, Q, Widmer, G, Tzipori, S. (2013). A pig model of the human gastrointestinal tract. Gut Microbes 4:193.

Barr, W H, Zola, E M, Candler, E L, Hwang, S-M, Tendolkar, A V, Shamburek, R, Parker, B, Hilty, M D. (1994). Differential absorptions of amoxicillin from the human small and large intestine. Clin. Pharm. & Ther. 56:279-285.

Davis, S S, Hardy, J G, Fara, J W. (2014). Transit of pharmaceutical dosage forms through the small intestine. *Gut* 27:886-892.

Du, X., Li, C., Sun, H. K., Nightingale, C. H., Niclau, D. P. (2005). A sensitive assay of amoxicillin in mouse serum and broncho-alveolar lagage fluid by liquid-liquid extraction and reversed-phase HPLC. J. Pharm Biomed Anal 39:648-652.

Hasan, N. A., Young, B. A., Minard-Smith, A. T., Saeed, K., et al. (2014). Microbial community profiling of human saliva using shotgun metagenomic sequencing. *PLoS One* 2014, 9, e97699. 10.1371/journal.pone.0097699

Lax, S., Smith, D. P., Hampton-Marcell, J., Owens, S. M., et al (2014). Longitudinal analysis of microbial interaction between humans and the indoor environment. *Science* 2014, 345, 1048-1052. 10.1126/science.1254529

---

What is claimed is:

1. A method of protecting a subject's gastrointestinal (GI) microbiome from an oral antibiotic, comprising administering a formulation comprising a beta-lactamase capable of deactivating the oral antibiotic to a subject who is undergoing treatment or has recently undergone treatment with the oral antibiotic, wherein:
the formulation comprises an enterically coated capsule comprising an enterically coated pellet, the pellet comprising, relative to a pellet's weight:
about 20% to 25% sucrose sphere;
about 30% to 40% binder excipient;
about 12% to 18% beta-lactamase;
about 1% to 2% buffer salts;
about 0.5% to 3% plasticizer;
about 15% to 30% EUDRAGIT® (poly(methacrylic acid, methylmethacrylate) coating, and
optionally about 0.5% to about 1.5% $KH_2PO_4$ and about 2.5% to 5% hydroxypropyl methylcellulose (HPMC) 603; and
the capsule is coated with FS EUDRAGIT® FS 30 D.

2. The method of claim 1, wherein the EUDRAGIT® coating is selected from EUDRAGIT® FS 30 D or EUDRAGIT® S100.

3. The method of claim 1, wherein:
the binder excipient is hydroxypropylcellulose (HPC); and/or
the beta-lactamase is selected from P1A, P2A, P3A, or P4A; and/or
the plasticizer is triethyl citrate.

4. The method of claim 3, wherein the beta-lactamase is P3A.

5. The method of claim 1, wherein the capsule is coated with FS EUDRAGIT® FS 30 D at about 10% of the total capsule weight.

6. The method of claim 1, wherein the capsule has a body capacity of less than about 15 μL and is coated with FS EUDRAGIT® FS 30 D.

7. The method of claim 6, wherein one or more capsules having body capacities of less than about 15 μL are loaded into a larger capsule.

8. The method of claim 1, wherein the capsule further comprises a beta-lactamase inhibitor.

9. The method of claim 8, wherein the beta-lactamase inhibitor is clavulanic acid.

10. The method of claim 1, wherein the protection of the subject's microbiome comprises treatment or prevention of a microbiome-mediated disorder.

11. The method of claim 10, wherein the microbiome-mediated disorder is selected from antibiotic-induced adverse effect, C. difficile infection (CDI), C. difficile-associated disease, ulcerative colitis, Crohn's disease, and irritable bowel syndrome.

12. The method of claim 11, wherein the microbiome-mediated disorder is one or more of an antibiotic-induced adverse effect, C. difficile infection (CDI), and a C. difficile-associated disease.

13. The method of claim 12, wherein the antibiotic-induced adverse effect, CDI, and/or C. difficile-associated disease is one or more of: antibiotic-associated diarrhea, C. difficile diarrhea (CDD), C. difficile intestinal inflammatory disease, colitis, pseudomembranous colitis, fever, abdominal pain, dehydration and disturbances in electrolytes, megacolon, peritonitis, and perforation and/or rupture of the colon.

14. The method of claim 1, wherein the protection of the subject's microbiome comprises maintenance of a normal intestinal microbiota.

15. The method of claim 1, wherein the method treats and/or prevents the overgrowth of one or more pathogenic microorganisms in the GI tract of a subject.

16. The method of claim 1, wherein the method treats or prevents a nosocomial infection and/or a secondary emergent infection.

17. The method of claim 1, wherein the beta-lactamase does not substantially interfere with plasma levels of a systemically absorbed orally administered antibiotic.

18. The method of claim 1, wherein the beta-lactamase deactivates residual oral antibiotic residue excreted into the GI tract, wherein the residual oral antibiotic is not absorbed from the GI tract after an oral dose or is returned in active form to the intestinal tract from the systemic circulation.

19. The method of claim 1, wherein the beta-lactamase is formulated for release in a location in the GI tract in which it does not substantially interfere with the systemic activity of the orally administered antibiotic.

20. The method of claim 1, wherein the beta-lactamase is formulated for release in a location in the GI tract that is distal to the release of the orally administered antibiotic.

* * * * *